(12) United States Patent
Thompson et al.

(10) Patent No.: US 7,247,748 B2
(45) Date of Patent: Jul. 24, 2007

(54) AMIDE COMPOUNDS AND METHODS OF USING THE SAME

(75) Inventors: Scott K. Thompson, King of Prussia, PA (US); James S. Frazee, King of Prussia, PA (US); Lara S. Kallander, King of Prussia, PA (US); Chun Ma, Edgewater, NJ (US); Joseph P. Marino, King of Prussia, PA (US); Michael J. Neeb, King of Prussia, PA (US); Ning Wang, King of Prussia, PA (US)

(73) Assignee: SmithKline Corporation, Philadelphia, PA (US)

( * ) Notice: Subject to any disclaimer, the term of this patent is extended or adjusted under 35 U.S.C. 154(b) by 0 days.

(21) Appl. No.: 10/508,791

(22) PCT Filed: Mar. 26, 2003

(86) PCT No.: PCT/US03/09461

§ 371 (c)(1),
(2), (4) Date: Sep. 22, 2004

(87) PCT Pub. No.: WO2004/043939

PCT Pub. Date: May 27, 2004

(65) Prior Publication Data

US 2005/0107444 A1    May 19, 2005

Related U.S. Application Data

(60) Provisional application No. 60/368,427, filed on Mar. 27, 2002.

(51) Int. Cl.
| | | |
|---|---|---|
| C07C 233/05 | (2006.01) | |
| C07C 233/65 | (2006.01) | |
| A61K 31/165 | (2006.01) | |

(52) U.S. Cl. .................... 564/164; 514/210; 514/212; 514/237.5; 514/255; 514/330; 514/604; 514/605; 514/620; 540/484; 544/162; 544/386; 546/226; 548/566; 548/953; 564/92; 564/99; 564/165

(58) Field of Classification Search ................. 564/92, 564/99, 164, 165; 548/566, 953; 540/484; 546/226; 514/604, 605, 210, 212, 237.5, 514/620, 255, 330, 423; 544/162, 386
See application file for complete search history.

(56) References Cited

U.S. PATENT DOCUMENTS

| 4,139,623 A | 2/1979 | Jaeggi et al. ............... 424/251 |
|---|---|---|
| 2003/0153541 A1 | 8/2003 | Dudley et al. ............... 514/171 |
| 2003/0162758 A1 | 8/2003 | Schwartz et al. ........... 514/172 |
| 2003/0229062 A1 | 12/2003 | Schwartz et al. ........... 514/177 |
| 2004/0072868 A1 | 4/2004 | Collins et al. ............... 514/318 |
| 2004/0266663 A1 | 12/2004 | Schwartz et al. ............... 514/2 |
| 2005/0036992 A1 | 2/2005 | Saez et al. ................ 424/93.21 |
| 2005/0107444 A1 | 5/2005 | Thompson et al. .......... 514/345 |
| 2005/0113580 A1 | 5/2005 | Thompson et al. ....... 546/268.1 |
| 2005/0131014 A1 | 6/2005 | Collini et al. ................ 514/311 |
| 2005/0171084 A1 | 8/2005 | Cairns et al. ........... 514/210.21 |
| 2005/0282750 A1 | 12/2005 | Schwartz et al. .............. 514/12 |
| 2005/0282908 A1 | 12/2005 | Collins et al. .............. 514/620 |

FOREIGN PATENT DOCUMENTS

| EP | 0 394 440 | 10/1990 |
|---|---|---|
| WO | WO 00/54759 | 9/2000 |
| WO | WO 01/60818 | 8/2001 |
| WO | WO 02/24632 | 3/2002 |
| WO | WO 03/082192 | 10/2003 |
| WO | WO 03/082205 | 10/2003 |
| WO | WO 03/082802 | 10/2003 |
| WO | WO 04/ 058819 A2 | 7/2004 |
| WO | WO 04/110368 A2 | 12/2004 |
| WO | WO 04/110375 A2 | 12/2004 |
| WO | WO 05/009383 A2 | 2/2005 |
| WO | WO 05/013946 A2 | 2/2005 |
| WO | WO 05/055998 A1 | 6/2005 |
| WO | WO 06/000576 A2 | 1/2006 |
| WO | WO 06/000577 A2 | 1/2006 |
| WO | WO 06/004030 A1 | 1/2006 |

OTHER PUBLICATIONS

U.S. Appl. No. 60/499,659, Hoang et al., filed Sep. 3, 2003.

(Continued)

*Primary Examiner*—Shailendra Kumar
(74) *Attorney, Agent, or Firm*—Kathryn L. Sieburth; Mary E. McCarthy; Charles M. Kinzig

(57) ABSTRACT

Disclosed is a compound having the formula (I) pharmaceutically acceptable salts or solvates thereof and pharmaceutical compositions containing the same, wherein the structural variables are as defined herein. The compounds, salts and solvates of this invention are useful as LXR agonists

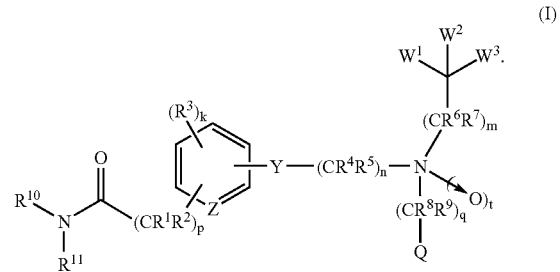

27 Claims, No Drawings

OTHER PUBLICATIONS

U.S. Appl. No. 60/500,295, Hoang et al., filed Sep. 4, 2003.
U.S. Appl. No. 60/499,779, Kallander et al., filed Sep. 3, 2003.
U.S. Appl. No. 60/500,296, Kallander et al., filed Sep. 4, 2003.
U.S. Appl. No. 60/499,762, Hoang et al., filed Sep. 3, 2003.
Grefhorst et al. *Am. J. Physiol. Endocrinol. Metab.*, 289: E829-E838 (2005).
Groot et al. *J. Lipid Res.*, 46: 2182-2191 (2005).
Jaye et al. *J. Med. Chem.*, 48: 5419-5422 (2005).
Ogawa et al. *J. Med. Chem.*, 96: e59-e67 (2005).
Quninet et al. *J. Lipid Res.*, 45: 1929-1942 (2004).
Miao et al. *J. Lipid Res.*, 45: 140-1417 (2004).
Schmuth et al. *J. Invest. Dermatol.* 123: 41-48 (2004).
Farnegardh et al. *J. Biol. Chem.*, 278(40): 38821-38828 (2003).
Wang et al. *J. Molec. Graphics and Modelling*, 22: 173-181 (2003).
Fowler et al. *J. Invest. Dermatol.*, 120: 246-255 (2003).
Joseph et al. *PNAS USA*, 99(11): 7604-7609 (2002).
Fluhr et al. *J. Invest Dermatol.*, 125: 1206-1214 (2005).
Naik et al. *Circulation*, 113: 90-97 (2006).
Kruit et al. *Gastroenterology*, 128: 147-156 (2005).
Laffitte et al. *PNAS USA*, 100(9): 5419-5424 (2003).
Castrillo et al. *J. Biol. Chem.*, 278(12): 10443-10449 (2003).
Laffitte et al. *Mol. & Cell. Biol.*, 23(6): 2182-2191 (2003).
Collins et al. *J. Med. Chem.*, 45: 1963-1966 (2002).
Terasaka et al. *FEBS Journal*, 272: 1546-1556 (2005).
Collins et al. *Abstracts of Papers, 230th ACS National Meeting, Washington, DC. Aug. 28-Sep. 1, 2005. MEDI-237. Publisher: American Chemical Society, Washington, DC.*
Rao et al *Abstracts of Papers, 229th ACS National Meeting, San Diego, CA. Mar. 13-17, 2005. COMP-258. Publisher: American Chemical Society, Washington, DC.*
Jon L. Collins *Abstracts of Papers, 225th ACS National Meeting, New Orleans, LA. Mar. 23-27, 2003. MEDI-152. Publisher: American Chemical Society, Washington, DC.*
Collins et al. *Abstracts of Papers, 223rd ACS National Meeting, Orlando, FL. Apr. 7-11, 2002. MEDI-123. Publisher: American Chemical Society, Washington, DC.*
Angelo Gavezzotti. Acc. Chem. Res., 27: 309-314 (1994).
Vippagunta et al. Advanced Drug Delivery Reviews, 48: 3-26 (2001).
Office Action: U.S. Appl. No. 10/508,849, filed Feb. 5, 2007.

SEQUENCE LISTING

<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Modified polyhistidine tag

<400> SEQUENCE: 1

Met Lys Lys Gly His His His His His His Gly
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Biotinylated Peptide Comprising Amino Acids
      675-699 or SRC-1

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25

AMIDE COMPOUNDS AND METHODS OF USING THE SAME

This application is a 371 of International Application No. PCT/US03/009461, filed 26 Mar. 2003, claims the benefit of U.S. Provisional Application No. 60/368,427, filed 27 Mar. 2002.

FIELD OF THE INVENTION

The present invention relates to compounds useful as modulating agents for liver X receptors (LXR). Additionally, the present invention relates to pharmaceutical formulations comprising such compounds, and the therapeutic use of the same.

BACKGROUND OF THE INVENTION

LXR is a transcription factor. The orphan nuclear receptors, LXRα and LXRβ (collectively LXR) play a role in the maintenance of cholesterol balance. Peet et al., *Curr. Opin. Genet. Dev.* 8:571–575 (1998). In addition, LXR binds to the ATP Binding Cassette Transporter-1 (ABCA1) gene and increases expression of the gene to result in increased ABCA1 protein. ABCA1 is a membrane bound transport protein that is involved in the regulation of cholesterol efflux from extrahepatic cells onto nascent HDL particles. Mutations in the ABCA1 gene are responsible for genetic diseases that result in the complete absence or low levels of HDL cholesterol and a concomitant highly increased risk of cardiovascular disease. See Brooks-Wilson et al., *Nat. Genet.* 22:336–345 (1999); Bodzioch et al., *Nat. Genet.* 22: 347–351 (1999); and Rust et al., *Nat. Genet.* 22:352–355 (1999). ABCA1 knockout mice homozygous for the mutation in the ABCA1 gene have virtually no plasma HDL, whereas the heterozygotes produce 50% of the HDL of wild type animals. See, Orso et al., *Nat. Genet* 24:192–196 (2000) and McNeish et al., *Proc. Natl. Acad. Sci. USA* 97:4245–4250 (2000). ABCA1 knockout mice also show increased cholesterol absorption. See, McNeish et al., *Proc. Natl. Acad. Sci. USA* 97:4245–4250 (2000). Increased expression of ABCA1 results in increased HDL cholesterol, decreased absorption of cholesterol, and increased removal of excess cholesterol from extrahepatic tissues, including macrophages. LXR agonists also upregulate macrophage expression of apolipoprotein E and ABCG1, both of which contribute to the efflux of cellular cholesterol. By stimulating macrophage cholesterol efflux through upregulation of ABCA1, ABCG1, and apoE expression, as well as increasing the expression of other target genes including cholesteryl ester transfer protein and lipoprotein lipase, LXR agonists influence plasma lipoproteins.

Accordingly, compounds which function as LXR modulating agents, and particularly as LXR agonists, would be useful in methods of increasing ABCA1, ABCG1, and apolipoprotein E expression, increasing cholesterol efflux from peripheral cells, and treating LXR mediated diseases and conditions such as cardiovascular disease and inflammation.

SUMMARY OF THE INVENTION

This invention is directed to a compound of Formula I:

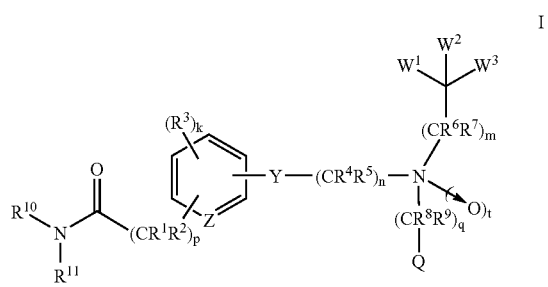

wherein:

Z is CH, CR$^3$ or N, wherein when Z is CH or CR$^3$, k is 0–4 and t is 0 or 1, and when Z is N, k is 0–3 and t is 0;

Y is selected from —O—, —S—, —N(R$^{12}$)—, and —C(R$^4$)(R$^5$)—;

W$^1$ is selected from C$_1$–C$_6$ alkyl, C$_0$–C$_6$ alkyl C$_3$–C$_8$ cycloalkyl, aryl and Het, wherein said C$_1$–C$_8$ alkyl, C$_3$–C$_8$ cycloalkyl, Ar and Het are optionally unsubstituted or substituted with one or more groups independently selected from halo, cyano, nitro, C$_1$–C$_6$ alkyl, C$_3$–C$_6$ alkenyl, C$_3$–C$_6$ alkynyl, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-SO$_3$H, —C$_0$–C$_6$ alkyl-SO$_2$NR$^{13}$R$^{14}$, —C$_0$–C$_6$ alkyl-SO$_2$R$^{12}$, —C$_0$–C$_6$ alkyl-SOR$^{15}$, —C$_0$–C$_6$ alkyl-OCOR$^{15}$, —C$_0$–C$_6$ alkyl-OC(O)NR$^{13}$R$^{14}$, —C$_0$–C$_6$ alkyl-OC(O)OR$^{15}$, —C$_0$–C$_6$ alkyl-NR$^{13}$C(O)OR$^{15}$, —C$_0$–C$_6$ alkyl-NR$^{13}$C(O)NR$^{13}$R$^{14}$, and —C$_0$–C$_6$ alkyl-NR$^{13}$COR$^{15}$, where said C$_1$–C$_6$ alkyl, is optionally unsubstituted or substituted by one or more halo substituents;

W$^2$ is selected from H, halo, C$_1$–C$_6$ alkyl, C$_2$–C$_6$ alkenyl, C$_2$–C$_6$ alkynyl, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-OCOR$^{15}$, —C$_0$–C$_6$ alkyl-OCONR$^{13}$R$^{14}$, —C$_0$–C$_6$ alkyl-NR$^{13}$CONR$^{13}$R$^{14}$, —C$_0$–C$_6$ alkyl-NR$^{13}$COR$^{15}$, —C$_0$–C$_6$ alkyl-Het, —C$_0$–C$_6$ alkyl-Ar and —C$_0$–C$_6$ alkyl-C$_3$–C$_7$ cycloalkyl, wherein said C$_1$–C$_6$ alkyl is optionally unsubstituted or substituted by one or more halo substituents, and wherein the C$_3$–C$_7$ cycloalkyl, Ar and Het moieties of said —C$_0$–C$_6$ alkyl-Het, —C$_0$–C$_6$ alkyl-Ar and —C$_0$–C$_6$ alkyl-C$_3$–C$_7$ cycloalkyl are optionally unsubstituted or substituted with one or more groups independently selected from halo, cyano, nitro, C$_1$–C$_6$ alkyl, C$_3$–C$_6$ alkenyl, C$_3$–C$_6$ alkynyl, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-SO$_3$H, —C$_0$–C$_6$ alkyl-SO$_2$NR$^{13}$R$^{14}$, —C$_0$–C$_6$ alkyl-SO$_2$R$^{12}$, —C$_0$–C$_6$ alkyl-SOR$^{15}$, —C$_0$–C$_6$ alkyl-OCOR$^{15}$, —C$_0$–C$_6$ alkyl-OC(O)NR$^{13}$R$^{14}$, —C$_0$–C$_6$ alkyl-OC(O)OR$^{15}$, —C$_0$–C$_6$ alkyl-NR$^{13}$C(O)OR$^{15}$, —C$_0$–C$_6$ alkyl-NR$^{13}$C(O)NR$^{13}$R$^{14}$, and —C$_0$–C$_6$ alkyl-NR$^{13}$COR$^{15}$, where said C$_1$–C$_6$ alkyl, is optionally unsubstituted or substituted by one or more halo substituents;

W$^3$ is selected from the group consisting of: H, halo, C$_1$–C$_6$ alkyl, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-OCOR$^{15}$, —C$_0$–C$_6$ alkyl-OCONR$^{13}$R$^{14}$, —C$_0$–C$_6$ alkyl-NR$^{13}$CONR$^{13}$R$^{14}$, —C$_0$–C$_6$ alkyl-NR$^{13}$COR$^{15}$, —C$_0$–C$_6$ alkyl-Het, —C$_1$–C$_6$ alkyl-Ar and —C$_1$–C$_6$ alkyl-C$_3$–C$_7$ cycloalkyl, wherein said C$_1$–C$_6$ alkyl is optionally unsubstituted or substituted by one or more halo substituents;

Q is selected from C$_3$–C$_8$ cycloalkyl, Ar and Het; wherein said C$_3$–C$_8$ cycloalkyl, Ar and Het are optionally unsubstituted or substituted with one or more groups independently selected from halo, cyano, nitro, C$_1$–C$_6$ alkyl, C$_3$–C$_6$ alkenyl, C$_3$–C$_6$ alkynyl, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-SO$_3$H, —C$_0$–C$_6$ alkyl-SO$_2$NR$^{13}$R$^{14}$, —C$_0$–C$_6$ alkyl-SO$_2$R$^{12}$, —C$_0$–C$_6$ alkyl-SOR$^{15}$, —C$_0$–C$_6$ alkyl-OCOR$^{15}$, —C$_0$–C$_6$ alkyl-OC(O)NR$^{13}$R$^{14}$, —C$_0$–C$_6$ alkyl-OC(O)OR$^{15}$, —C$_0$–C$_6$ alkyl-NR$^{13}$C(O)OR$^{15}$, —C$_0$–C$_6$ alkyl-NR$^{13}$C(O)NR$^{13}$R$^{14}$, and —C$_0$–C$_6$ alkyl-NR$^{13}$COR$^{15}$, where said C$_1$–C$_6$ alkyl is optionally unsubstituted or substituted by one or more halo substituents;

p is 0–8;
n is 2–8;
m is 0 or 1;
q is 0 or 1;
t is 0 or 1;

each R$^1$ and R$^2$ are independently selected from H, halo, C$_1$–C$_6$ alkyl, C$_3$–C$_6$ alkenyl, C$_3$–C$_6$ alkynyl, —C$_0$–C$_6$ alkyl-NR$^{13}$R$^{14}$, —C$_0$–C$_6$ alkyl-OR$^{12}$, —C$_0$–C$_6$ alkyl-SR$^{12}$, —C$_1$–C$_6$ alkyl-Het, —C$_1$–C$_6$ alkyl-Ar and —C$_1$–C$_6$ alkyl-C$_3$–C$_7$ cycloalkyl, or R$^1$ and R$^2$ together with the carbon to which they are attached form a 3–5 membered carbocyclic or heterocyclic ring, wherein said heterocyclic ring contains one, or more heteroatoms selected from N, O, and S, where any of said C$_1$–C$_6$ alkyl is optionally unsubstituted or substituted by one or more halo substituents;

each R$^3$ is the same or different and is independently selected from halo, cyano, nitro, C$_1$–C$_6$ alkyl, C$_3$–C$_6$ alkenyl, C$_3$–C$_6$ alkynyl, —C$_0$–C$_6$ alkyl-Ar, —C$_0$–C$_6$ alkyl-Het, —C$_0$–C$_6$ alkyl-C$_3$–C$_7$ cycloalkyl, —C$_0$–C$_6$ alkyl-CO$_2$R$^{12}$, —C$_0$–C$_6$ alkyl-C(O)SR$^{12}$, —C$_0$–C$_6$ alkyl-CONR$^{13}$R$^{14}$, —C$_0$–C$_6$ alkyl-COR$^{15}$, —C$_0$–C$_6$ alkyl-NR$^{13}$R$^{14}$, —C$_0$–C$_6$ alkyl-SR$^{12}$, —C$_0$–C$_6$ alkyl-OR$^{12}$, —C$_0$–C$_6$ alkyl-SO$_3$H, —C$_0$–C$_6$ alkyl-SO$_2$NR$^{13}$R$^{14}$, —C$_0$–C$_6$ alkyl-SO$_2$R$^{12}$, —C$_0$–C$_6$ alkyl-SOR$^{15}$, —C$_0$–C$_6$ alkyl-OCOR$^{15}$, —C$_0$–C$_6$ alkyl-OC(O)NR$^{13}$R$^{14}$, —C$_0$–C$_6$ alkyl-OC(O)OR$^{15}$, —C$_0$–C$_6$ alkyl-NR$^{13}$C(O)OR$^{15}$, —C$_0$–C$_6$ alkyl-NR$^{13}$C(O)NR$^{13}$R$^{14}$, and —C$_0$–C$_6$ alkyl-NR$^{13}$COR$^{15}$, wherein said C$_1$–C$_6$ alkyl is optionally unsubstituted or substituted by one or more halo substituents;

each R$^4$ and R$^5$ is independently selected from H, halo, C$_1$–C$_6$ alkyl, —C$_0$–C$_6$ alkyl-Het, —C$_0$–C$_6$ alkyl-Ar and —C$_0$–C$_6$ alkyl-C$_3$–C$_7$ cycloalkyl;

R$^6$ and R$^7$ are each independently selected from H, halo, C$_1$–C$_6$ alkyl, —C$_0$–C$_6$ alkyl-Het, —C$_0$–C$_6$ alkyl-Ar and —C$_0$–C$_6$ alkyl-C$_3$–C$_7$ cycloalkyl;

R$^8$ and R$^9$ are each independently selected from H, halo, C$_1$–C$_6$ alkyl, —C$_0$–C$_6$ alkyl-Het, —C$_0$–C$_6$ alkyl-Ar and —C$_0$–C$_6$ alkyl-C$_3$–C$_7$ cycloalkyl;

R$^{10}$ and R$^{11}$ are each independently selected from H, C$_1$–C$_{12}$ alkyl, C$_3$–C$_{12}$ alkenyl, C$_3$–C$_{12}$ alkynyl, —C$_0$–C$_8$ alkyl-Ar, —C$_0$–C$_8$ alkyl-Het, —C$_0$–C$_8$ alkyl-C$_3$–C$_7$ cycloalkyl, —C$_0$–C$_8$ alkyl-O-Ar, —C$_0$–C$_8$ alkyl-O-Het, —C$_0$–C$_8$ alkyl-O-C$_3$–C$_7$ cycloalkyl, —C$_0$–C$_8$ alkyl-S(O)$_x$— C$_0$–C$_6$ alkyl, —C$_0$–C$_8$ alkyl-S(O)$_x$-Ar, —C$_0$–C$_8$ alkyl-S(O)$_x$-Het, —C$_0$–C$_8$ alkyl-S(O)$_x$–C$_3$–C$_7$ cycloalkyl, —C$_0$–C$_8$ alkyl-NH-Ar, —C$_0$–C$_8$ alkyl-NH-Het, —C$_0$–C$_8$ alkyl-NH—C$_3$–C$_7$ cycloalkyl, —C$_0$–C$_8$ alkyl-N(C$_1$–C$_4$ alkyl)-Ar, —C$_0$–C$_8$ alkyl-N(C$_1$–C$_4$ alkyl)-Het, —C$_0$–C$_8$ alkyl-N(C$_1$–C$_4$ alkyl)-C$_3$–C$_7$ cycloalkyl, —C$_0$–C$_8$ alkyl-Ar, —C$_0$–C$_8$ alkyl-Het and —C$_0$–C$_8$ alkyl-C$_3$–C$_7$ cycloalkyl, where x is 0, 1 or 2, or R$^{10}$ and R$^{11}$, together with the nitrogen to which they are attached, form a 4–7 membered heterocyclic ring which optionally contains one or more additional heteroatoms selected from N, O, and S, wherein said C$_1$–C$_{12}$ alkyl, C$_3$–C$_{12}$ alkenyl, or C$_3$–C$_{12}$ alkynyl is optionally substituted by one or more of the substituents independently selected from the group halo, —OH, —SH, —NH$_2$, —NH(unsubstituted C$_1$–C$_6$ alkyl), —N(unsubstituted C$_1$–C$_6$ alkyl)(unsubstituted C$_1$–C$_6$ alkyl), unsubstituted —OC$_1$–C$_6$ alkyl, —CO$_2$H, —CO$_2$(unsubstituted C$_1$–C$_6$ alkyl), —CONH$_2$, —CONH(unsubstituted C$_1$–C$_6$ alkyl), —CON(unsubstituted C$_1$–C$_6$ alkyl)(unsubstituted C$_1$–C$_6$ alkyl), —SO$_3$H, —SO$_2$NH$_2$, —SO$_2$NH(unsubstituted C$_1$–C$_6$ alkyl) and —SO$_2$N(unsubstituted C$_1$–C$_6$ alkyl)(unsubstituted C$_1$–C$_6$ alkyl);

R$^{12}$ is selected from H, C$_1$–C$_6$ alkyl, C$_3$–C$_6$ alkenyl, C$_3$–C$_6$ alkynyl, —C$_0$–C$_6$ alkyl-Ar, —C$_0$–C$_6$ alkyl-Het and —C$_0$–C$_6$ alkyl-C$_3$–C$_7$ cycloalkyl;

each R$^{13}$ and each R$^{14}$ are independently selected from H, C$_1$–C$_6$ alkyl, C$_3$–C$_6$ alkenyl, C$_3$–C$_6$ alkynyl, —C$_0$–C$_6$ alkyl-Ar, —C$_0$–C$_6$ alkyl-Het and —C$_0$–C$_6$ alkyl-C$_3$–C$_7$ cycloalkyl, or R$^{13}$ and R$^{14}$ together with the nitrogen to which they are attached form a 4–7 membered heterocyclic ring which optionally contains one or more additional heteroatoms selected from N, O, and S; and R$^{15}$ is selected from C$_1$–C$_6$ alkyl, C$_3$–C$_6$ alkenyl, C$_3$–C$_6$ alkynyl, —C$_0$–C$_6$ alkyl-Ar, —C$_0$–C$_6$ alkyl-Het and —C$_0$–C$_6$ alkyl-C$_3$–C$_7$ cycloalkyl;

provided that R$^{10}$ and R$^{11}$ are not both H when Z is CH or N, Y is —O—, n is 3, m is 1 and each R$^4$, R$^5$, R$^6$, R$^7$ are H, W$^3$ is H, p is 0 or p is 1 or 2 and R$^1$ and R$^2$ are each H, k is 0 or k is 1 and R$^3$ is halo or C$_1$–C$_4$ alkoxy, q is 0 or q is 1 or 2 and R$^8$ and R$^9$ are each H, Q is unsubstituted C$_3$–C$_7$ cycloalkyl, phenyl or Het, or phenyl substituted by one or more substituents selected from halo, —CH$_3$, —CH$_2$CH$_3$, —CF$_3$, —OC$_1$–C$_4$ alkyl, —OCH$_2$CH$_2$OH, —OCF$_3$, —OCF$_2$H, —SCH$_3$, —SCF$_3$, —SO$_2$CH$_3$, —CO$_2$H, —CO$_2$CH$_3$, —OH, —OCH$_2$CO$_2$H, —CH$_2$CONH$_2$, —NO$_2$, —CN, —N(CH$_3$)$_2$, and —NHC(O)CH$_3$, or Het substituted by one or more substituents selected from: —C$_1$–C$_3$ alkyl, —OC$_1$–C$_4$ alkyl, —CH$_2$OH, —CO$_2$H, —CO$_2$CH$_2$CH$_3$, —CO$_2$-tert-C$_4$H$_9$ alkyl, —CO$_2$CH$_2$-phenyl, —CONH$_2$, —C(O)phenyl, —C(O)CH$_3$, —CH$_2$CH$_2$-phenyl, and oxo, t is 0, and W$^1$ and W$^2$ are each independently selected from unsubstituted cyclohexyl and unsubstituted phenyl; or
provided that the compound is not:
3-[3-[[2-[3,4-bis(phenylmethoxy)phenyl]-2-hydroxyethyl](phenylmethyl)amino]propyl]-benzamide,
(S)-2-hydroxy-5-[2-[(2-hydroxy-2-phenylethyl)(phenylmethyl)amino]ethoxyl]-benzamide,
5-[2-[[2-[3,5-bis(phenylmethoxy)phenyl]-2-hydroxyethyl](phenylmethyl)amino]ethoxy]-2-hydroxy-benzamide,
2-hydroxy-4-[3-[(2-hydroxy-2-phenylethyl)(phenylmethyl)amino]propoxy]-benzamide,
2-hydroxy-4-[2-[(2-hydroxy-2-phenylethyl)(phenylmethyl)amino]ethoxy]-benzamide,
(R)-2-hydroxy-5-[2-[(2-hydroxy-2-phenylethyl)(phenylmethyl)amino]ethoxy]-benzamide,
2-hydroxy-5-[3-[(2-hydroxy-2-phenylethyl)(phenylmethyl)amino]propyl]-benzamide,
2-hydroxy-5-[2-[(2-hydroxy-2-phenylethyl)(phenylmethyl)amino]ethoxy]-benzamide, 5-[2-[[2-(4-fluorophenyl)-2-hydroxyethyl](phenylmethyl)amino]ethoxy]-2-hydroxy benzamide, 5-[2-[[2-[3-(aminosulfonyl)-4methoxyphenyl]-2-hydroxyethyl](phenylmethyl)amino]ethoxy]-2-hydroxy-benzamide, (R)-4-[2-[[2-hydroxy-2-[3-(trifluoromethyl)phenyl]ethyl](phenylmethyl)amino]ethoxy]-benzeneacetamide, (R)-4-[2-[(2-hydroxy-2-phenylethyl)(phenylmethyl)amino]ethoxy]-benzeneacetamide, 4-[2-[(2-hydroxy-2-phenylethyl)(phenylmethyl)amino]ethoxy]-benzeneacetamide, 5-[2-[[2-4-fluorophenyl)-2-hydroxyethyl](phenylmethyl)amino]ethoxy]-2-hydroxy-benzamine, or 4-[2-[[2-[3,4-bis(phenylmethoxy)phenyl]-2-hydroxyethyl](phenylmethyl)amino]ethoxy]-benzamide, or a pharmaceutically acceptable salt or solvate thereof.

This invention is also directed to methods for the prevention or treatment of an LXR mediated disease or condition comprising administering a therapeutically effective amount of a compound having Formula I-A:

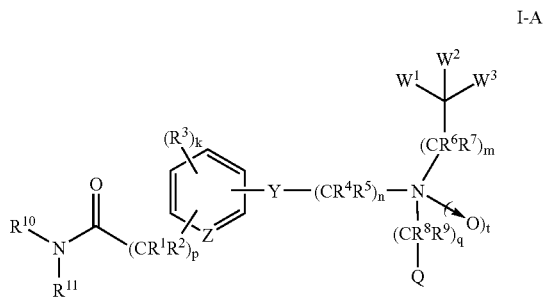

I-A wherein:

Z is CH, $CR^3$ or N, wherein when Z is CH or $CR^3$, k is 0–4 and t is 0 or 1, and when Z is N, k is 0–3 and t is 0;

Y is selected from —O—, —S—, —N($R^{12}$)—, and —C($R^4$)($R^5$)—;

$W^1$ is selected from $C_1$–$C_6$ alkyl, $C_0$–$C_6$ alkyl $C_3$–$C_8$ cycloalkyl, aryl and Het, wherein said $C_1$–$C_8$ alkyl, $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-CON$R^{13}R^{14}$, —$C_0$–$C_6$ alkyl-$COR^{15}$, —$C_0$–$C_6$ alkyl-N$R^{13}R^{14}$, —$C_0$–$C_8$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}C(O)OR^{15}$, —$C_0$–$C_6$ alkyl-$NR^{13}C(O)NR^{13}R^{14}$, and —$C_0$–$C_6$ alkyl-$NR^{13}COR^{15}$, where said $C_1$–$C_6$ alkyl, is optionally unsubstituted or substituted by one or more halo substituents;

$W^2$ is selected from H, halo, $C_1$–$C_6$ alkyl, $C_2$–$C_6$ alkenyl, $C_2$–$C_6$ alkynyl, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$OCOR^{15}$, —$C_0$–$C_6$ alkyl-$OCONR^{13}R^{14}$, —$C_0$–$C_6$ alkyl-$NR^{13}CONR^{13}R^{14}$, —$C_0$–$C_6$ alkyl-$NR^{13}COR^{15}$, —$C_0$–$C_6$ alkyl-Het, —$C_0$–$C_6$ alkyl-Ar and —$C_0$–$C_6$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_6$ alkyl-Het, —$C_0$–$C_6$ alkyl-Ar and —$C_0$–$C_6$ alkyl-$C_3$–$C_7$ cycloalkyl are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}C(O)OR^{15}$, —$C_0$–$C_6$ alkyl-$NR^{13}C(O)NR^{13}R^{14}$, and —$C_0$–$C_6$ alkyl-$NR^{13}COR^{15}$, where said $C_1$–$C_6$ alkyl, is optionally unsubstituted or substituted by one or more halo substituents;

$W^3$ is selected from the group consisting of: H, halo, $C_1$–$C_6$ alkyl, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$OCOR^{15}$, —$C_0$–$C_6$ alkyl-$OCONR^{13}R^{14}$, —$C_0$–$C_6$ alkyl-$NR^{13}CONR^{13}R^{14}$, —$C_0$–$C_6$ alkyl-$NR^{13}COR^{15}$, —$C_0$–$C_6$ alkyl-Het, —$C_1$–$C_6$ alkyl-Ar and —$C_1$–$C_6$ alkyl-$C_3$–$C_7$ cycloalkyl, wherein said $C_1$–$C_6$ alkyl is optionally unsubstituted or substituted by one or more halo substituents;

Q is selected from $C_3$–$C_8$ cycloalkyl, Ar and Het; wherein said $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}C(O)OR^{15}$, —$C_0$–$C_6$ alkyl-$NR^{13}C(O)NR^{13}R^{14}$, and —$C_0$–$C_6$ alkyl-$NR^{13}COR^{15}$, where said $C_1$–$C_6$ alkyl is optionally unsubstituted or substituted by one or more halo substituents;

p is 0–8;

n is 2–8;

m is 0 or 1;

q is 0 or 1;

t is 0 or 1;

each $R^1$ and $R^2$ are independently selected from H, halo, $C_1$–$C_6$ alkyl, $C_3$–$C_6$ alkenyl, $C_3$–$C_6$ alkynyl, —$C_0$–$C_6$ alkyl-$NR^{13}R^{14}$, —$C_0$–$C_6$ alkyl-$OR^{12}$, —$C_0$–$C_6$ alkyl-$SR^{12}$, —$C_0$–$C_6$ alkyl-Het, —$C_1$–$C_6$ alkyl-Ar and —$C_1$–$C_6$ alkyl-$C_3$–$C_7$ cycloalkyl, or $R^1$ and $R^2$ together with the carbon to which they are attached form a 3–5 membered carbocyclic or heterocyclic ring, wherein said heterocyclic ring contains one, or more heteroatoms selected from N, O, and S, where any of said $C_1$–$C_6$ alkyl is optionally unsubstituted or substituted by one or more halo substituents;

each $R^3$ is the same or different and is independently selected from halo, cyano, nitro, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het, —$C_0$–$C_6$ alkyl-$C_3$–$C_7$ cycloalkyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}C(O)OR^{15}$, —$C_0$–$C_6$ alkyl-$NR^{13}C(O)

$NR^{13}R^{14}$, and —$C_0$–$C_6$ alkyl-$NR^{13}COR^{15}$, wherein said $C_1$–$C_6$ alkyl is optionally unsubstituted or substituted by one or more halo substituents;

each $R^4$ and $R^5$ is independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

$R^6$ and $R^7$ are each independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

$R^8$ and $R^9$ are each independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

$R^{10}$ and $R^{11}$ are each independently selected from H, $C_1$–$C_{12}$ alkyl, $C_3$–$C_{12}$ alkenyl, $C_3$–$C_{12}$ alkynyl, —$C_0$–$C_8$ alkyl-Ar, —$C_0$–$C_8$ alkyl-Het, —$C_0$–$C_8$ alkyl-$C_3$–$C_7$ cycloalkyl, —$C_0$–$C_8$ alkyl-O-Ar, —$C_0$–$C_8$ alkyl-O-Het, —$C_0$–$C_8$ alkyl-O-$C_3$–$C_7$ cycloalkyl, —$C_0$–$C_8$ alkyl-$S(O)_x$—$C_0$–$C_6$ alkyl, —$C_0$–$C_8$ alkyl-$S(O)_x$-Ar, —$C_0$–$C_8$ alkyl-$S(O)_x$-Het, —$C_0$–$C_8$ alkyl-$S(O)_x$—$C_3$–$C_7$ cycloalkyl, —$C_0$–$C_8$ alkyl-NH-Ar, —$C_0$–$C_8$ alkyl-NH-Het, —$C_0$–$C_8$ alkyl-NH—$C_3$–$C_7$ cycloalkyl, —$C_0$–$C_8$ alkyl-$N(C_1$–$C_4$ alkyl)-Ar, —$C_0$–$C_8$ alkyl-$N(C_1$–$C_4$ alkyl)-Het, —$C_0$–$C_8$ alkyl-$N(C_1$–$C_4$ alkyl)-$C_3$–$C_7$ cycloalkyl, —$C_0$–$C_8$ alkyl-Ar, —$C_0$–$C_8$ alkyl-Het and —$C_0$–$C_8$ alkyl-$C_3$–$C_7$ cycloalkyl, where x is 0, 1 or 2, or $R^{10}$ and $R^{11}$, together with the nitrogen to which they are attached, form a 4–7 membered heterocyclic ring which optionally contains one or more additional heteroatoms selected from N, O, and S, wherein said $C_1$–$C_{12}$ alkyl, $C_3$–$C_{12}$ alkenyl, or $C_3$–$C_{12}$ alkynyl is optionally substituted by one or more of the substituents independently selected from the group halo, —OH, —SH, —$NH_2$, —NH(unsubstituted $C_1$–$C_6$ alkyl), —N(unsubstituted $C_1$–$C_6$ alkyl)(unsubstituted $C_1$–$C_6$ alkyl), unsubstituted —$OC_1$–$C_6$ alkyl, —$CO_2H$, —$CO_2$(unsubstituted $C_1$–$C_6$ alkyl), —$CONH_2$, —CONH(unsubstituted $C_1$–$C_6$ alkyl), —CON(unsubstituted $C_1$–$C_6$ alkyl)(unsubstituted $C_1$–$C_6$ alkyl), —$SO_3H$, —$SO_2NH_2$, —$SO_2NH$(unsubstituted $C_1$–$C_6$ alkyl) and —$SO_2N$(unsubstituted $C_1$–$C_6$ alkyl)(unsubstituted $C_1$–$C_6$ alkyl);

$R^{12}$ is selected from H, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl;

each $R^{13}$ and each $R^{14}$ are independently selected from H, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl, or $R^{13}$ and $R^{14}$ together with the nitrogen to which they are attached form a 4–7 membered heterocyclic ring which optionally contains one or more additional heteroatoms selected from N, O, and S; and $R^{15}$ is selected from $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl;

provided that $R^{10}$ and $R^{11}$ are not both H when Z is CH or N, Y is —O—, n is 3, m is 1 and each $R^4$, $R^5$, $R^6$, $R^7$ are H, $W^3$ is H, p is 0 or p is 1 or 2 and $R^1$ and $R^2$ are each H, k is 0 or k is 1 and $R^3$ is halo or $C_1$–$C_4$ alkoxy, q is 0 or q is 1 or 2 and $R^8$ and $R^9$ are each H, Q is unsubstituted $C_3$–$C_7$ cycloalkyl, phenyl or Het, or phenyl substituted by one or more substituents selected from halo, —$CH_3$, —$CH_2CH_3$, —$CF_3$, —$OC_1$–$C_4$ alkyl, —$OCH_2CH_2OH$, —$OCF_3$, —$OCF_2H$, —$SCH_3$, —$SCF_3$, —$SO_2CH_3$, —$CO_2H$, —$CO_2CH_3$, —OH, —$OCH_2CO_2H$, —$CH_2CONH_2$, —$NO_2$, —CN, —$N(CH_3)_2$, and —$NHC(O)CH_3$, or Het substituted by one or more substituents selected from: —$C_1$–$C_3$ alkyl, —$OC_1$–$C_4$ alkyl, —$CH_2OH$, —$CO_2H$, —$CO_2CH_2CH_3$, —$CO_2$-tert-$C_4H_9$ alkyl, —$CO_2CH_2$-phenyl, —$CONH_2$, —$C(O)$phenyl, —$C(O)CH_3$, —$CH_2CH_2$-phenyl, and oxo, t is 0, and $W^1$ and $W^2$ are each independently selected from unsubstituted cyclohexyl and unsubstituted phenyl; or or a pharmaceutically acceptable salt or solvate thereof.

Also included within the scope of this invention are methods for preparing compounds of this invention, or pharmaceutically acceptable salts or solvates thereof.

Unless otherwise provided, each alkyl, alkoxy, alkenyl, alkynyl, cycloalkyl, aryl or Het (including any 3–5-membered, 4–7-membered or 5–7-membered carbocyclic or heterocyclic rings or ring moieties) herein is independently unsubstituted or substituted with one ore more substituents defined hereinbelow.

LXR mediated diseases or conditions include inflammation, cardiovascular disease and atherosclerosis. Accordingly, the methods of this invention further comprise methods for increasing reverse cholesterol transport, inhibiting cholesterol absorption, and decreasing inflammation. The present invention also provides pharmaceutical compositions comprising a compound of this invention.

DETAILED DESCRIPTION OF THE INVENTION

As used herein, the term "alkyl" represents a straight-or branched-chain saturated hydrocarbon, containing 1 to 10 carbon atoms, unless otherwise provided, which may be unsubstituted or substituted by one or more of the substituents described below. Exemplary alkyls include, but are not limited to methyl (Me), ethyl (Et), n-propyl, isopropyl, n-butyl, isobutyl, t-butyl, n-pentyl, neopentyl and hexyl and structural isomers thereof. Any "alkyl" herein may be optionally substituted by one or more of the substituents independently selected from the group halo, —OH, —H, —$NH_2$, —NH(unsubstituted $C_1$–$C_6$ alkyl), —N(unsubstituted $C_1$–$C_6$ alkyl)(unsubstituted $C_1$–$C_6$ alkyl), unsubstituted —$OC_1$–$C_6$ alkyl, and —$CO_2H$.

When combined with another substituent term (e.g., aryl or cycloalkyl as in -alkyl-Ar or -alkyl-cycloalkyl), the "alkyl" term therein refers to an alkylene moiety, that is, an unsubstituted divalent straight-or branched-chain saturated hydrocarbon moiety, containing 1 to 10 carbon atoms, unless otherwise provided. For example, the term "—$C_0$–$C_6$ alkyl-Ar", where C is 1–6 is intended to mean the radical -alkyl-aryl (e.g., —$CH_2$-aryl or —$CH(CH_3)$-aryl) and is represented by the bonding arrangement present in a benzyl group. The term "$C_0$ alkyl" in a moiety, such as —$C_0$–$C_6$ alkyl-Ar or —O—($C_0$–$C_6$ alkyl)-Ar, provides for no alkyl/ alkylene group being present in the moiety. Thus, when C is zero, —$C_0$–$C_6$ alkyl-Ar is equivalent to -Ar and —O—($C_0$–$C_6$ alkyl)-Ar is equivalent to —O-Ar.

As used herein, the term "alkenyl" represents a straight-or branched-chain hydrocarbon, containing 2 to 10 carbon atoms, unless otherwise provided, and one or more carbon—carbon double bonds. Alkenyl groups may be unsubstituted or substituted by one or more of the substituents described below. Exemplary alkenyls include, but are not limited to ethenyl, 1-propenyl, 2-propenyl, 1-butenyl, 2-butenyl, isobutenyl, butadienyl, pentenyl and hexenyl and structural isomers thereof. Both cis (Z) and trans (E) isomers of each double bond that may be present in the compounds of this invention are included within the scope of this invention. Any "alkenyl" herein may be optionally substituted by one or more of the substituents independently selected from the group halo, —OH, —SH, —$NH_2$, —NH(unsubstituted $C_1$–$C_6$ alkyl), —N(unsubstituted $C_1$–$C_6$ alkyl)(unsubstituted $C_1$–$C_6$ alkyl), unsubstituted —$OC_1$–$C_6$ alkyl, and —$CO_2H$.

As used herein, the term "alkynyl" represents a straight- or branched-chain hydrocarbon, containing 2 to 10 carbon atoms, unless otherwise provided, and one or more carbon—carbon triple bonds and, optionally, one or more carbon—carbon double bonds. Both cis (Z) and trans (E) isomers of each double bond that may be present in the compounds of this invention are included within the scope of this invention. Exemplary alkynyls include, but are not limited to ethynyl, propynyl (propargyl, isopropynyl), 1-butynyl, 2-butynyl, 3-butynyl, pentynyl and hexynyl and structural isomers thereof. Any "alkynyl" herein may be optionally substituted by one or more of the substituents independently selected from the group halo, —OH, —SH, —$NH_2$, —NH(unsubstituted $C_1$–$C_6$ alkyl), —N(unsubstituted $C_1$–$C_6$ alkyl)(unsubstituted $C_1$–$C_6$ alkyl), unsubstituted —$OC_1$–$C_6$ alkyl, and —$CO_2H$.

For the purposes of this invention, when an alkenyl or alkynyl group is a substituent on an oxygen, nitrogen or sulfur atom (e.g., as in oxy (—OR), thio (—SR), ester (—$CO_2R$ or —C(O)SR), amino (—NRR) or amido (—CONRR) moieties and the like), it is understood that a double or triple bond of the alkenyl or alkynyl group is not located on carbons that are α,β to the oxygen, nitrogen or sulfur atom. Compounds containing ene-amino or enol-type moieties (—NR—CR=CR— or —O—CR=CR—) are not intended to be included within the scope of this invention.

"Cycloalkyl" represents a non-aromatic monocyclic, bicyclic, or tricyclic hydrocarbon containing from 3 to 10 carbon atoms which may be unsubstituted or substituted by one or more of the substituents described below and may be saturated or partially unsaturated. Exemplary cycloalkyls include monocyclic rings having from 3–7, preferably 3–6, carbon atoms, such as cyclopropyl, cyclobutyl, cyclopentyl, cyclopentenyl, cyclopentadienyl, cyclohexyl, cyclohexenyl and cycloheptyl. Any "cycloalkyl" herein may be optionally substituted by one or more of the substituents independently selected from the group halo, cyano, $C_1$–$C_6$ alkyl (which specifically includes $C_1$–$C_6$ haloalkyl, —$C_0$–$C_6$ alkyl-OH, —$C_0$–$C_6$ alkyl-SH and —$C_0$–$C_6$ alkyl-NR'R"), $C_3$–$C_6$ alkenyl, oxo, —$OC_1$–$C_6$alkyl, —$OC_1$–$C_6$ alkenyl, —$C_0$–$C_6$ alkyl-COR', —$C_0$–$C_6$ alkyl-$CO_2R'$, —$C_0$–$C_6$ alkyl-CONR'R", —$OC_0$–$C_6$ alkyl-$CO_2H$, —$OC_0$–$C_6$ alkyl-NR'R", and —$C_0$–$C_6$ alkyl-$SO_2NR'R"$, wherein each R' and R" are independently selected from H and unsubstituted $C_1$–$C_6$ alkyl.

The terms "Ar" or "aryl" as used herein interchangeably at al occurrences mean a substituted or unsubstituted carbocyclic aromatic group, which may be optionally fused to another carbocyclic aromatic group moiety or to a cycloalkyl group moiety, which may be optionally substituted or unsubstituted. Examples of suitable Ar or aryl groups include phenyl, naphthyl indenyl, 1-oxo-1H-indenyl and tetrahydronaphthyl. Any "Ar", "aryl" or "phenyl" herein may be optionally unsubstituted or substituted by one or more of the substituents independently selected from the group halo, cyano, $C_1$–$C_6$ alkyl (which specifically includes $C_1$–$C_6$ haloalkyl, —$C_0$–$C_6$ alkyl-OH, —$C_0$–$C_6$ alkyl-SH and —$C_0$–$C_6$ alkyl-NR'R"), $C_3$–$C_6$ alkenyl, oxo, —$OC_1$–$C_6$alkyl, —$OC_1$–$C_6$ alkenyl, —$C_0$–$C_6$ alkyl-COR', —$C_0$–$C_6$ alkyl-$CO_2R'$, —$C_0$–$C_6$ alkyl-CONR'R", —$OC_0$–$C_6$ alkyl-$CO_2H$, —$OC_2$–$C_6$ alkyl-NR'R", —$C_0$–$C_6$ alkyl-C(=NR')NR'R", and —$C_0$–$C_6$ alkyl-$SO_2NR'R"$, wherein each R' and R" are independently selected from H and unsubstituted $C_1$–$C_6$ alkyl.

The term "Het" as used herein means a stable 5- to 7-membered monocyclic, a stable 7- to 10-membered bicyclic, or a stable 11- to 18-membered tricyclic heterocyclic ring group, all of which are saturated, unsaturated or aromatic, and consist of carbon atoms and from one to three heteroatoms selected from N, O and S, and which includes bicyclic and tricyclic rings containing one or more fused cycloalkyl, aryl (e.g., phenyl) or heteroaryl (aromatic Het) ring moieties. As used herein the term "Het" is also intended to encompass heterocyclic groups containing nitrogen and/or sulfur where the nitrogen or sulfur heteroatoms are optionally oxidized or the nitrogen heteroatom is optionally quaternized. The heterocyclic group may be attached at any heteroatom or carbon atom that results in the creation of a stable structure. Any "Het" herein may be optionally unsubstituted or substituted by one or more of the substituents independently selected from the group halo, cyano, $C_1$–$C_6$ alkyl (which specifically includes $C_1$–$C_6$ haloalkyl, —$C_0$–$C_6$ alkyl-OH, —$C_0$–$C_6$ alkyl-SH and —$C_0$–$C_6$ alkyl-NR'R"), $C_3$–$C_6$ alkenyl, oxo, —$OC_1$–$C_6$alkyl, —$OC_1$–$C_6$ alkenyl, —$C_0$–$C_6$ alkyl-COR', —$C_0$–$C_6$ alkyl-$CO_2R'$, —$C_0$–$C_6$ alkyl-CONR'R", —$OC_0$–$C_6$ alkyl-$CO_2H$, —$OC_2$–$C_6$ alkyl-NR'R", —$C_0$–$C_6$ alkyl-C(=NR')NR'R" and —$C_0$–$C_6$ alkyl-$SO_2NR'R"$, wherein each R' and R" are independently selected from H and unsubstituted $C_1$–$C_6$ alkyl.

Examples of such heterocyclic groups include, but are not limited to piperidinyl, piperazinyl, 2-oxopiperazinyl, 2-oxopiperidinyl, 2-oxopyrrolodinyl, 2-oxoazepinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, 1,3-benzodioxolyl (e.g., methylenedioxy-substituted phenyl), 1,4-benzodioxolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, benzofuranyl, benzothienyl, dihydrobenzofuranyl, dihydrobenzothienyl, dihydroindolyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable.

Examples of the 4–7 membered heterocyclic rings useful in the compounds of this invention, include, but are not limited to azetidinyl, piperidinyl, piperazinyl, 2-oxopiperazinyl, 2-oxopiperidinyl, 2-oxopyrrolodinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 4–7 membered heterocyclic group may be optionally unsubstituted or substituted by one or more of the substituents independently selected from the group halo, cyano, $C_1$–$C_6$ alkyl (which specifically includes $C_1$–$C_6$ haloalkyl, —$C_0$–$C_6$ alkyl-OH, —$C_0$–$C_6$ alkyl-SH and —$C_0$–$C_6$ alkyl-NR'R"), $C_3$–$C_6$ alkenyl, oxo, —$OC_1$–$C_6$alkyl, —$OC_1$–$C_6$ alkenyl, —$C_0$–$C_6$ alkyl-COR', —$C_0$–$C_6$ alkyl-$CO_2R'$, —$C_0$–$C_6$ alkyl-CONR'R", —$OC_0$–$C_6$ alkyl-$CO_2H$, —$OC_2$–$C_6$ alkyl-NR'R", —$C_0$–$C_6$ alkyl-C(=NR')NR'R" and —$C_0$–$C_6$ alkyl-$SO_2NR'R"$, wherein each R' and R" are independently selected from H and unsubstituted $C_1$–$C_6$ alkyl.

Examples of 5 or 6 membered heterocyclic groups include, but are not limited to piperidinyl, piperazinyl, 2-oxopiperazinyl, 2-oxopiperidinyl, 2-oxopyrrolodinyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 5–6 membered heterocyclic group may be attached at any heteroatom or carbon atom that results in the creation of a stable structure. The 5–6 membered heterocyclic group may be optionally unsubstituted or substituted by one or more of the substituents independently selected from the group halo, cyano, $C_1$–$C_6$ alkyl (which specifically includes $C_1$–$C_6$ haloalkyl, —$C_0$–$C_6$ alkyl-OH, —$C_0$–$C_6$ alkyl-SH and —$C_0$–$C_6$ alkyl-NR'R"), $C_3$–$C_6$ alkenyl, oxo, —$OC_1$–$C_6$alkyl, —$OC_1$–$C_6$ alkenyl, —$C_0$–$C_6$ alkyl-COR', —$C_0$–$C_6$ alkyl-$CO_2$R', —$C_0$–$C_6$ alkyl-CONR'R", —$OC_0$–$C_6$ alkyl-$CO_2$H, —$OC_2$–$C_6$ alkyl-NR'R", —$C_0$–$C_6$ alkyl-(=NR')NR'R" and —$C_0$–$C_6$ alkyl-$SO_2$NR'R", wherein each R' and R" are independently selected from H and unsubstituted $C_1$–$C_6$ alkyl.

The terms "halogen" and "halo" represent chloro, fluoro, bromo or iodo substituents. "Alkoxy" is intended to mean the radical —$OR_a$, where $R_a$ is an alkyl group, wherein alkyl is as defined above, provided that —O—$C_1$ alkyl may be optionally substituted by one or more of the substituents independently selected from the group halo, —$CO_2$H and —$SO_3$H. Exemplary alkoxy groups include methoxy, ethoxy, propoxy, and the like. "Phenoxy" is intended to mean the radical —$OR_{ar}$, where $R_{ar}$ is a phenyl group. "Acetoxy" is intended to mean the radical —O—C(=O)-methyl. "Benzoyloxy" is intended to mean the radical —O—C(=O)-phenyl. "Oxo" is intended to mean the keto diradical =O, such as present on a pyrrolidin-2-one ring.

If a substituent described herein is not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful as an intermediate compound in the methods of this invention or is a desired substituent in a target compound.

The term "pharmaceutically acceptable salt" is intended to describe a salt that retains the biological effectiveness of the free acid or base of a specified compound and is not biologically or otherwise undesirable.

If an inventive compound is a base, a desired salt may be prepared by any suitable method known in the art, including treatment of the free base with an inorganic acid, such as hydrochloric acid, hydrobromic acid, sulfuric acid, sulfamic acid, nitric acid, phosphoric acid, metaphosphoric acid and the like, or with an organic acid, such as acetic acid, trifluoroacetic acid, formic acid, maleic acid, lactic acid, succinic acid, mandelic acid, fumaric acid, malonic acid, malic acid, pyruvic acid, oxalic acid, glycolic acid, citric acid, tartaric acid, gluconic acid, glutaric acid, lactobionic, orotic, cholic, a pyranosidyl acid, such as glucuronic acid or galacturonic acid, an amino acid, such as aspartic acid or glutamic acid, an aromatic acid, such as benzoic acid, salicylic acid, cinnamic acid, pamoic acid or 1-hydroxy-2-naphthoic acid, a sulfonic acid, such as benzenesulfonic acid, p-toluenesulfonic acid, naphthalenesulfonic acid, methanesulfonic acid, ethanesulfonic acid or the like. Additional examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates. Embodiments of a pharmaceutically acceptable salt (e.g., the hydrochloride salt) of the compounds of this invention are provided in the Examples.

If an inventive compound is an acid, a desired salt may be prepared by any suitable method known to the art, including treatment of the free acid with an excess of an inorganic or organic alkaline reagent. Illustrative examples of suitable salts include salts derived from ammonia; primary, secondary, tertiary amines (including secondary and tertiary cyclic amines), such as ethylene diamine, dicyclohexylamine, ethanolamine, piperidine, morpholine, and piperazine; salts derived from amino acids such as glycine and arginine; as well as salts derived from an alkali metal, alkaline earth metal, or ammonium hydroxide, carbonate, alkoxide or sulfate, such as sodium hydroxide, sodium carbonate, sodium bicarbonate, sodium sulfate, etc., and corresponding alkaline salts containing, for example, $Li^+$, $K^+$, $Ca^{++}$, $Mg^{++}$ and $NH_4^+$ cations.

The term "solvate" is intended to mean a pharmaceutically acceptable solvate form of a specified compound of this invention, or a salt thereof, that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, or solvates may exist in different crystal forms, all of which are intended to be within the scope of the present invention and specified formulas.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a mesylate salt or a sodium salt.

Also included within the scope of this invention are prodrugs of the compounds of this invention. The ester compounds of this invention, wherein X is other than —OH, may be considered prodrugs. Such ester compounds may be converted to compounds that are active as LXR modulators and may be, themselves, active as LXR modulators. The term "prodrug" is intended to mean a compound that is converted under physiological conditions, e.g., by solvolysis or metabolically, to a compound according to this invention that is pharmaceutically active. A prodrug may be a derivative of one of the compounds of this invention that contains a carboxylic or phosphoric acid ester or amide moiety that may be cleaved under physiological conditions. A prodrug containing such a moiety may be prepared according to conventional procedures, for example, by treatment of a compound of this invention containing an amino, amido or hydroxyl moiety with a suitable derivatizing agent, for example, a carboxylic or phosphoric acid halide or acid anhydride, or by converting a carboxyl moiety of a compound of this invention to an ester or amide. Prodrugs of the compounds of this invention may be determined using techniques known in the art, for example, through metabolic studies. See, e.g., "Design of Prodrugs," (H. Bundgaard, Ed.) 1985, Elsevier Publishers B.V., Amsterdam, The Netherlands.

It will be appreciated by those skilled in the art that the compounds of this invention may exist in different tautomeric forms. All tautomeric forms of the compounds described herein are intended to be encompassed within the scope of the present invention.

The compounds of this invention may contain at least one chiral center and may exist as single stereoisomers (e.g., single enantiomers), mixtures of stereoisomers (e.g., any mixture of enantiomers or diastereomers) or racemic mixtures thereof. All such single stereoisomers, stereoisomeric mixtures and racemates are intended to be encompassed within the broad scope of the present invention. Compounds identified herein as single stereoisomers are meant to describe compounds that are present in a form that are at least 90% enantiomerically pure. Where the stereochemistry of the chiral carbons present in the chemical structures illustrated herein is not specified, the chemical structure is intended to encompass compounds containing either stereoisomer of each chiral center present in the compound. Such compounds may be obtained synthetically, according to the procedures described herein using optically pure (enantiomerically pure) or substantially optically pure materials. Alternatively, these compounds may be obtained by resolution/separation of a mixture of stereoisomers, including racemic mixtures, using conventional procedures. Exemplary methods that may be useful for the resolution/separation of mixtures of stereoisomers include chromatography and crystallization/re-crystallization. Other useful methods may be found in "Enantiomers, Racemates, and Resolutions," J. Jacques et al., 1981, John Wiley and Sons, New York, N.Y., the disclosure of which is incorporated herein by reference.

In another embodiment, this invention is directed to a compound of Formula II:

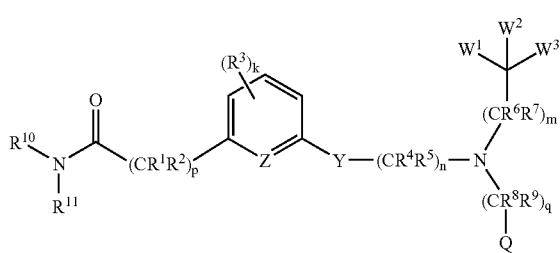

II wherein:

Z is CH or N, wherein k is 0, 1 or 2;

Y is —O— or —C(R$^4$)(R$^5$)—;

W$^1$ is selected from $C_1$–$C_6$ alkyl, $C_3$–$C_8$ cycloalkyl, aryl or Het, wherein said $C_1$–$C_6$ alkyl, $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-C(O)SR$^{12}$, —$C_0$–$C_4$ alkyl-CONR$^{13}R^{14}$, —$C_0$–$C_4$ alkyl-COR$^{15}$, —$C_0$–$C_4$ alkyl-NR$^{13}R^{14}$, —$C_0$–$C_4$ alkyl-SR$^{12}$, —$C_0$–$C_4$ alkyl-OR$^{12}$, —$C_0$–$C_4$ alkyl-SO$_3$H, —$C_0$–$C_4$ alkyl-SO$_2$NR$^{13}R^{14}$, —$C_0$–$C_4$ alkyl-SO$_2R^{12}$, —$C_0$–$C_4$ alkyl-SOR$^{15}$, —$C_0$–$C_4$ alkyl-OCOR$^{15}$, —$C_0$–$C_4$ alkyl-OC(O)NR$^{13}R^{14}$, —$C_0$–$C_4$ alkyl-OC(O)OR$^{15}$, —$C_0$–$C_4$ alkyl-NR$^{13}$C(O)OR$^{15}$, —$C_0$–$C_4$ alkyl-NR$^{13}$C(O)NR$^{13}R^{14}$, and —$C_0$–$C_4$ alkyl-NR$^{13}$COR$^{15}$, where said $C_1$–$C_6$ alkyl is optionally unsubstituted or substituted by one or more halo substituents;

W$^2$ is selected from H, halo, $C_1$–$C_6$ alkyl, $C_2$–$C_6$ alkenyl, $C_2$–$C_6$ alkynyl, —$C_0$–$C_4$ alkyl-NR$^{13}R^{14}$, —$C_0$–$C_4$ alkyl-SR$^{12}$, —$C_0$–$C_4$ alkyl-OR$^{12}$, —$C_0$–$C_4$ alkyl-CO$_2R^{12}$, —$C_0$–$C_4$ alkyl-C(O)SR$^{12}$, —$C_0$–$C_4$ alkyl-CONR$^{13}R^{14}$, —$C_0$–$C_4$ alkyl-COR$^{15}$, —$C_0$–$C_4$ alkyl-OCOR$^{15}$, —$C_0$–$C_4$alkyl-OCONR$^{13}R^{14}$, —$C_0$–$C_4$ alkyl-NR$^{13}$CONR$^{13}R^{14}$, —$C_0$–$C_4$ alkyl-NR$^{13}$COR$^{15}$, —$C_0$–$C_4$ alkyl-Het, —$C_0$–$C_4$ alkyl-Ar and —$C_0$–$C_4$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_4$ alkyl-Het, —$C_0$–$C_4$ alkyl-Ar and —$C_0$–$C_4$ alkyl-$C_3$–$C_7$ cycloalkyl are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-C(O)SR$^{12}$, —$C_0$–$C_4$ alkyl-CONR$^{13}R^{14}$, —$C_0$–$C_4$ alkyl-COR$^{15}$, —$C_0$–$C_4$ alkyl-NR$^{13}R^{14}$, —$C_0$–$C_4$ alkyl-SR$^{12}$, —$C_0$–$C_4$ alkyl-OR$^{12}$, —$C_0$–$C_4$ alkyl-SO$_3$H, —$C_0$–$C_4$ alkyl-SO$_2$NR$^{13}R^{14}$, —$C_0$–$C_4$ alkyl-SO$_2R^{12}$, —$C_0$–$C_4$ alkyl-SOR$^{15}$, —$C_0$–$C_4$ alkyl-OCOR$^{15}$, —$C_0$–$C_4$ alkyl-OC(O)NR$^{13}R^{14}$, —$C_0$–$C_4$ alkyl-OC(O)OR$^{15}$, —$C_0$–$C_4$ alkyl-NR$^{13}$C(O)OR$^{15}$, —$C_0$–$C_4$ alkyl-NR$^{13}$C(O)NR$^{13}R^{14}$, and —$C_0$–$C_4$ alkyl-NR$^{13}$COR$^{15}$, where said $C_1$–$C_6$ alkyl is optionally unsubstituted or substituted by one or more halo substituents;

W$^3$ is selected from the group consisting of: H, halo, $C_1$–$C_6$ alkyl, —$C_0$–$C_4$ alkyl-NR$^{13}R^{14}$, —$C_0$–$C_4$ alkyl-SR$^{12}$, —$C_0$–$C_4$ alkyl-OR$^{12}$, —$C_0$–$C_4$ alkyl-CO$_2R^{12}$, —$C_0$–$C_4$ alkyl-C(O)SR$^{12}$, —$C_0$–$C_4$ alkyl-CONR$^{13}R^{14}$, —$C_0$–$C_4$ alkyl-COR$^{15}$, —$C_0$–$C_4$ alkyl-OCOR$^{15}$, —$C_0$–$C_4$ alkyl-OCONR$^{13}R^{14}$, —$C_0$–$C_4$ alkyl-NR$^{13}$CONR$^{13}R^{14}$, —$C_0$–$C_4$ alkyl-NR$^{13}$COR$^{15}$, —$C_0$–$C_4$ alkyl-Het, —$C_1$–$C_4$ alkyl-Ar and —$C_1$–$C_4$ alkyl-$C_3$–$C_7$ cycloalkyl, wherein said $C_1$–$C_6$ alkyl is optionally unsubstituted or substituted by one or more halo substituents;

Q is phenyl or Het; wherein said phenyl or Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-C(O)SR$^{12}$, —$C_0$–$C_4$ alkyl-CONR$^{13}R^{14}$, —$C_0$–$C_4$ alkyl-COR$^{15}$, —$C_0$–$C_4$ alkyl-NR$^{13}R^{14}$, —$C_0$–$C_4$ alkyl-SR$^{12}$, —$C_0$–$C_4$ alkyl-OR$^{12}$, —$C_0$–$C_4$ alkyl-SO$_3$H, —$C_0$–$C_4$ alkyl-SO$_2$NR$^{13}R^{14}$, —$C_0$–$C_4$ alkyl-SO$_2R^{12}$, —$C_0$–$C_4$ alkyl-SOR$^{15}$, —$C_0$–$C_4$ alkyl-OCOR$^{15}$, —$C_0$–$C_4$ alkyl-OC(O)NR$^{13}R^{14}$, —$C_0$–$C_4$ alkyl-OC(O)OR$^{15}$, —$C_0$–$C_4$ alkyl-NR$^{13}$C(O)OR$^{15}$, —$C_0$–$C_4$ alkyl-NR$^{13}$C(O)NR$^{13}R^{14}$, and —$C_0$–$C_4$ alkyl-NR$^{13}$COR$^{15}$, where said $C_1$–$C_6$ alkyl is optionally unsubstituted or substituted by one or more halo substituents, p is 0–4;

n is 3;

m is 0 or 1;

q is 0 or 1;

t is 0;

each R$^1$ and R$^2$ are independently selected from H, fluoro, $C_1$–$C_6$ alkyl, —$C_0$–$C_4$ alkyl-OR$^{12}$, —$C_0$–$C_4$ alkyl-SR$^{12}$, —$C_1$–$C_4$ alkyl-Het, —$C_1$–$C_4$ alkyl-Ar and —$C_1$–$C_4$ alkyl- $C_3$–$C_7$ cycloalkyl, where any of said $C_1$–$C_6$ alkyl is optionally unsubstituted or substituted by one or more halo substituents;

each $R^3$ is the same or different and is independently selected from halo, cyano, $C_1$–$C_6$ alkyl, —$C_0$–$C_4$ alkyl-$NR^{13}R^{14}$, —$C_0$–$C_4$ alkyl-$OR^{12}$, —$C_0$–$C_4$alkyl-$SO_2NR^{13}R^{14}$, and —$C_0$–$C_4$ alkyl-$CO_2H$, wherein said $C_1$–$C_6$ alkyl is optionally unsubstituted or substituted by one or more halo substituents;

each $R^4$ and $R^5$ is independently selected from H, fluoro and $C_1$–$C_6$ alkyl;

$R^6$ and $R^7$ are each independently selected from H, fluoro and $C_1$–$C_6$ alkyl;

$R^8$ and $R^9$ are each independently selected from H, fluoro and $C_1$–$C_6$ alkyl;

$R^{10}$ and $R^{11}$ are each independently selected from H, $C_1$–$C_{10}$ alkyl, $C_3$–$C_8$ alkenyl, $C_3$–$C_8$ alkynyl, —$C_0$–$C_6$ alkyl-Ar, —$C_0$–$C_6$ alkyl-Het, —$C_0$–$C_6$ alkyl-$C_3$–$C_7$ cycloalkyl, —$C_0$–$C_6$ alkyl-O-Ar, —$C_0$–$C_6$ alkyl-O-Het, —$C_0$–$C_6$ alkyl-O—$C_3$–$C_7$ cycloalkyl, —$C_0$–$C_6$ alkyl-$S(O)_x$, —$C_1$–$C_6$ alkyl, —$C_0$–$C_6$ alkyl-$S(O)_x$-Ar, —$C_0$–$C_6$ alkyl-$S(O)_x$-Het, —$C_0$–$C_6$ alkyl-$S(O)_x$—$C_3$–$C_7$ cycloalkyl, —$C_0$–$C_6$ alkyl-NH-Ar, —$C_0$–$C_6$ alkyl-NH-Het, —$C_0$–$C_6$ alkyl-NH—$C_3$–$C_7$ cycloalkyl, —$C_0$–$C_6$ alkyl-N($C_1$–$C_4$ alkyl)-Ar, —$C_0$–$C_6$ alkyl-N($C_1$–$C_4$ alkyl)-Het, —$C_0$–$C_6$ alkyl-N($C_1$–$C_4$ alkyl)-$C_3$–$C_7$ cycloalkyl, —$C_0$–$C_6$ alkyl-Ar, —$C_0$–$C_6$ alkyl-Het and —$C_0$–$C_6$ alkyl-$C_3$–$C_7$ cycloalkyl, where x is 0, 1 or 2, or $R^{11}$ and $R^{12}$, together with the nitrogen to which they are attached, form a 4–7 membered heterocyclic ring which optionally contains one or more additional heteroatoms selected from N, O, and S, wherein said $C_1$–$C_{10}$ alkyl, $C_3$–$C_{10}$ alkenyl, $C_3$–$C_{10}$ alkynyl are optionally substituted by one or more of the substituents independently selected from the group halo, —OH, —SH, —$NH_2$, —NH(unsubstituted $C_1$–$C_4$ alkyl), —N(unsubstituted $C_1$–$C_4$ alkyl)(unsubstituted $C_1$–$C_4$ alkyl), unsubstituted —O$C_1$–$C_4$ alkyl, —$CO_2H$, —$CO_2$(unsubstituted $C_1$–$C_4$ alkyl), —$CONH_2$, —CONH(unsubstituted $C_1$–$C_4$ alkyl), —CON(unsubstituted $C_1$–$C_4$ alkyl)(unsubstituted $C_1$–$C_4$ alkyl), —$SO_3H$, —$SO_2NH_2$, —$SO_2NH$(unsubstituted $C_1$–$C_4$ alkyl) and —$SO_2N$(unsubstituted $C_1$–$C_4$ alkyl)(unsubstituted $C_1$–$C_4$ alkyl);

$R^{12}$ is selected from H, $C_1$–$C_6$ alkyl, —$C_0$–$C_4$ alkyl-Ar, —$C_0$–$C_4$ alkyl-Het and —$C_0$–$C_4$ alkyl-$C_3$–$C_7$ cycloalkyl;

each $R^{13}$ and $R^{14}$ are each independently selected from H, $C_1$–$C_6$ alkyl, —$C_0$–$C_4$ alkyl-Ar, —$C_0$–$C_4$ alkyl-Het and —$C_0$–$C_4$ alkyl-$C_3$–$C_7$ cycloalkyl, or $R^{13}$ and $R^{14}$ together with the nitrogen to which they are attached form a 4–7 membered heterocyclic ring which optionally contains one or more additional heteroatoms selected from N, O, and S; and $R^{15}$ is selected from $C_1$–$C_6$ alkyl, —$C_0$–$C_4$ alkyl-Ar, —$C_0$–$C_4$ alkyl-Het and —$C_0$–$C_4$ alkyl-$C_3$–$C_7$ cycloalkyl;

provided that $R^{10}$ and $R^{11}$ are not both H when Z is CH or N, Y is —O—, n is 3, m is 1 and each $R^4$, $R^5$, $R^6$, $R^7$ are H, $W^3$ is H, p is 0 or p is 1 or 2 and $R^1$ and $R^2$ are each H, k is 0 or k is 1 and $R^3$ is halo or $C_1$–$C_4$ alkoxy, q is 0 or q is 1 or 2 and $R^8$ and $R^9$ are each H, Q is unsubstituted phenyl or Het, or phenyl substituted by one or more substituents selected from halo, —$CH_3$, —$CH_2CH_3$, —$CF_3$, —$OC_1$–$C_4$ alkyl, —$OCH_2CH_2OH$, —$OCF_3$, —$OCF_2H$, —$SCH_3$, —$SCF_3$, —$SO_2CH_3$, —$CO_2H$, —$CO_2CH_3$, —OH, —$OCH_2CO_2H$, —$CH_2CONH_2$, —$NO_2$, —CN, —$N(CH_3)_2$, and —$NHC(O)CH_3$, or Het substituted by one or more substituents selected from: —$C_1$–$C_3$ alkyl, —$OC_1$–$C_4$ alkyl, —$CH_2OH$, —$CO_2H$, —$CO_2CH_2CH_3$, —$CO_2$-tert-$C_4H_9$ alkyl, —$CO_2CH_2$-phenyl, —$CONH_2$, —$C(O)$phenyl, —$C(O)CH_3$, —$CH_2CH_2$-phenyl, and oxo, t is 0, and $W^1$ and $W^2$ are each independently selected from unsubstituted cyclohexyl and unsubstituted phenyl; or provided that the compound is not 2-hydroxy-4-[3-[(2-hydroxy-2-phenylethyl)(phenylmethyl)amino]propoxy]-benzamide, or a pharmaceutically acceptable salt or solvate thereof.

In another embodiment, this invention is directed to methods for the prevention or treatment of an LXR mediated disease or condition comprising administering a therapeutically effective amount of a compound having Formula II-A:

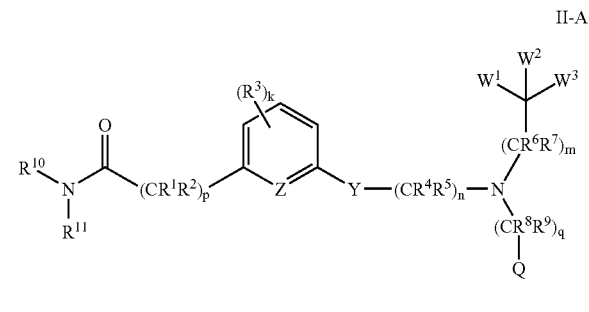

II-A wherein:

Z is CH or N, wherein k is 0, 1 or 2;

Y is —O— or —$C(R^4)(R^5)$—;

$W^1$ is selected from $C_1$–$C_6$ alkyl, $C_3$–$C_8$ cycloalkyl, aryl or Het, wherein said $C_1$–$C_6$ alkyl, $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-$C(O)SR^{12}$, —$C_0$–$C_4$ alkyl-$CONR^{13}R^{14}$, —$C_0$–$C_4$ alkyl-$COR^{15}$, —$C_0$–$C_4$ alkyl-$NR^{13}R^{14}$, —$C_0$–$C_4$ alkyl-$SR^{12}$, —$C_0$–$C_4$ alkyl-$OR^{12}$, —$C_0$–$C_4$ alkyl-$SO_3H$, —$C_0$–$C_4$ alkyl-$SO_2NR^{13}R^{14}$, —$C_0$–$C_4$ alkyl-$SO_2R^{12}$, —$C_0$–$C_4$ alkyl-$SOR^{15}$, —$C_0$–$C_4$ alkyl-$OCOR^{15}$, —$C_0$–$C_4$ alkyl-$OC(O)NR^{13}R^{14}$, —$C_0$–$C_4$ alkyl-$OC(O)OR^{15}$, —$C_0$–$C_4$ alkyl-$NR^{13}C(O)OR^{15}$, —$C_0$–$C_4$ alkyl-$NR^{13}C(O)NR^{13}R^{14}$, and —$C_0$–$C_4$ alkyl-$NR^{13}COR^{15}$, where said $C_1$–$C_6$ alkyl is optionally unsubstituted or substituted by one or more halo substituents;

$W^2$ is selected from H, halo, $C_1$–$C_6$ alkyl, $C_2$–$C_6$ alkenyl, $C_2$–$C_6$ alkynyl, —$C_0$–$C_4$ alkyl-$NR^{13}R^{14}$, —$C_0$–$C_4$ alkyl-$SR^{12}$, —$C_0$–$C_4$ alkyl-$OR^{12}$, —$C_0$–$C_4$ alkyl-$CO_2R^{12}$, —$C_0$–$C_4$ alkyl-$C(O)SR^{12}$, —$C_0$–$C_4$ alkyl-$CONR^{13}R^{14}$, —$C_0$–$C_4$ alkyl-$COR^{15}$, —$C_0$–$C_4$ alkyl-$OCOR^{15}$, —$C_0$–$C_4$alkyl-$OCONR^{13}R^{14}$, —$C_0$–$C_4$ alkyl-$NR^{13}CONR^{13}R^{14}$, —$C_0$–$C_4$ alkyl-$NR^{13}COR^{15}$, —$C_0$–$C_4$ alkyl-Het, —$C_0$–$C_4$ alkyl-Ar and —$C_0$–$C_4$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_4$ alkyl-Het, —$C_0$–$C_4$ alkyl-Ar and —$C_0$–$C_4$ alkyl-$C_3$–$C_7$ cycloalkyl are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-$C(O)SR^{12}$, —$C_0$–$C_4$ alkyl-$CONR^{13}R^{14}$, —$C_0$–$C_4$ alkyl-$COR^{15}$, —$C_0$–$C_4$ alkyl-$NR^{13}R^{14}$, —$C_0$–$C_4$ alkyl-$SR^{12}$, —$C_0$–$C_4$ alkyl-$OR^{12}$, —$C_0$–$C_4$ alkyl-$SO_3H$, —$C_0$–$C_4$ alkyl-$SO_2NR^{13}R^{14}$, —$C_0$–$C_4$ alkyl-$SO_2R^{12}$, —$C_0$–$C_4$ alkyl-$SOR^{15}$, —$C_0$–$C_4$ alkyl-$OCOR^{15}$, —$C_0$–$C_4$ alkyl-$OC(O)NR^{13}R^{14}$, —$C_0$–$C_4$ alkyl-$OC(O)OR^{15}$, —$C_0$–$C_4$ alkyl-$NR^{13}C(O)OR^{15}$, —$C_0$–$C_4$ alkyl-$NR^{13}C(O)NR^{13}R^{14}$, and —$C_0$–$C_4$ alkyl- NR$^{13}$COR$^{15}$, where said C$_1$–C$_6$ alkyl is optionally unsubstituted or substituted by one or more halo substituents;

W$^3$ is selected from the group consisting of: H, halo, C$_1$–C$_6$ alkyl, —C$_0$–C$_4$ alkyl-NR$^{13}$R$^{14}$, —C$_0$–C$_4$ alkyl-SR$^{12}$, —C$_0$–C$_4$ alkyl-OR$^{12}$, —C$_0$–C$_4$ alkyl-CO$_2$R$^{12}$, —C$_0$–C$_4$ alkyl-C(O)SR$^{12}$, —C$_0$–C$_4$ alkyl-CONR$^{13}$R$^{14}$, —C$_0$–C$_4$ alkyl-COR$^{15}$, —C$_0$–C$_4$ alkyl-OCOR$^{15}$, —C$_0$–C$_4$ alkyl-OCONR$^{13}$R$^{14}$, —C$_0$–C$_4$ alkyl-NR$^{13}$CONR$^{13}$R$^{14}$, —C$_0$–C$_4$ alkyl-NR$^{13}$COR$^{15}$, —C$_0$–C$_4$ alkyl-Het, —C$_1$–C$_4$ alkyl-Ar and —C$_1$–C$_4$ alkyl-C$_3$–C$_7$ cycloalkyl, wherein said C$_1$–C$_6$ alkyl is optionally unsubstituted or substituted by one or more halo substituents;

Q is phenyl or Het; wherein said phenyl or Het are optionally unsubstituted or substituted with one or more groups independently selected from halo, cyano, nitro, C$_1$–C$_6$ alkyl, C$_3$–C$_6$ alkenyl, C$_3$–C$_6$ alkynyl, —C$_0$–C$_4$ alkyl-CO$_2$R$^{12}$, —C$_0$–C$_4$ alkyl-C(O)SR$^{12}$, —C$_0$–C$_4$ alkyl-CONR$^{13}$R$^{14}$, —C$_0$–C$_4$ alkyl-COR$^{15}$, —C$_0$–C$_4$ alkyl-NR$^{13}$R$^{14}$, —C$_0$–C$_4$ alkyl-SR$^{12}$, —C$_0$–C$_4$ alkyl-OR$^{12}$, —C$_0$–C$_4$ alkyl-SO$_3$H, —C$_0$–C$_4$ alkyl-SO$_2$NR$^{13}$R$^{14}$, —C$_0$–C$_4$ alkyl-SO$_2$R$^{12}$, —C$_0$–C$_4$ alkyl-SOR$^{15}$, —C$_0$–C$_4$ alkyl-OCOR$^{15}$, —C$_0$–C$_4$ alkyl-OC(O)NR$^{13}$R$^{14}$, —C$_0$–C$_4$ alkyl-OC(O)OR$^{15}$, —C$_0$–C$_4$ alkyl-NR$^{13}$C(O)OR$^{15}$, —C$_0$–C$_4$ alkyl-NR$^{13}$C(O)NR$^{13}$R$^{14}$, and —C$_0$–C$_4$ alkyl-NR$^{13}$COR$^{15}$, where said C$_1$–C$_6$ alkyl is optionally unsubstituted or substituted by one or more halo substituents, p is 0–4;

n is 3;

m is 0 or 1;

q is 0 or 1;

t is 0;

each R$^1$ and R$^2$ are independently selected from H, fluoro, C$_1$–C$_6$ alkyl, —C$_0$–C$_4$ alkyl-OR$^{12}$, —C$_0$–C$_4$ alkyl-SR$^{12}$, —C$_0$–C$_4$ alkyl-Het, —C$_1$–C$_4$ alkyl-Ar and —C$_1$–C$_4$ alkyl-C$_3$–C$_7$ cycloalkyl, where any of said C$_1$–C$_6$ alkyl is optionally unsubstituted or substituted by one or more halo substituents;

each R$^3$ is the same or different and is independently selected from halo, cyano, C$_1$–C$_6$ alkyl, —C$_0$–C$_4$ alkyl-NR$^{13}$R$^{14}$, —C$_0$–C$_4$ alkyl-OR$^{12}$, —C$_0$–C$_4$alkyl-SO$_2$NR$^{13}$R$^{14}$, and —C$_0$–C$_4$ alkyl-CO$_2$H, wherein said C$_1$–C$_6$ alkyl is optionally unsubstituted or substituted by one or more halo substituents;

each R$^4$ and R$^5$ is each independently selected from H, fluoro and C$_1$–C$_6$ alkyl;

R$^6$ and R$^7$ are each independently selected from H, fluoro and C$_1$–C$_6$ alkyl;

R$^8$ and R$^9$ are each independently selected from H, fluoro and C$_1$–C$_6$ alkyl;

R$^{10}$ and R$^{11}$ are each independently selected from H, C$_1$–C$_{10}$ alkyl, C$_3$–C$_8$ alkenyl, C$_3$–C$_8$ alkynyl, —C$_0$–C$_6$ alkyl-Ar, —C$_0$–C$_6$ alkyl-Het, —C$_0$–C$_6$ alkyl-C$_3$–C$_7$ cycloalkyl, —C$_0$–C$_6$ alkyl-O-Ar, —C$_0$–C$_6$ alkyl-O-Het, —C$_0$–C$_6$ alkyl-O—C$_3$–C$_7$ cycloalkyl, —C$_0$–C$_6$ alkyl-S(O)$_x$—C$_1$–C$_6$ alkyl, —C$_0$–C$_6$ alkyl-S(O)$_x$-Ar, —C$_0$–C$_6$ alkyl-S(O)$_x$-Het, —C$_0$–C$_6$ alkyl-S(O)$_x$—C$_3$–C$_7$ cycloalkyl, —C$_0$–C$_6$ alkyl-NH-Ar, —C$_0$–C$_6$ alkyl-NH-Het, —C$_0$–C$_6$ alkyl-NH—C$_3$–C$_7$ cycloalkyl, —C$_0$–C$_6$ alkyl-N(C$_1$–C$_4$ alkyl)-Ar, —C$_0$–C$_6$ alkyl-N(C$_1$–C$_4$ alkyl)-Het, —C$_0$–C$_6$ alkyl-N(C$_1$–C$_4$ alkyl)-C$_3$–C$_7$ cycloalkyl, —C$_0$–C$_6$ alkyl-Ar, —C$_0$–C$_6$ alkyl-Het and —C$_0$–C$_6$ alkyl-C$_3$–C$_7$ cycloalkyl, where x is 0, 1 or 2, or R$^{11}$ and R$^{12}$, together with the nitrogen to which they are attached, form a 4–7 membered heterocyclic ring which optionally contains one or more additional heteroatoms selected from N, O, and S, wherein said C$_1$–C$_{10}$ alkyl, C$_3$–C$_{10}$ alkenyl, C$_3$–C$_{10}$ alkynyl are optionally substituted by one or more of the substituents independently selected from the group halo, —OH, —SH, —NH$_2$, —NH(unsubstituted C$_1$–C$_4$ alkyl), —N(unsubstituted C$_1$–C$_4$ alkyl)(unsubstituted C$_1$–C$_4$ alkyl), unsubstituted —OC$_1$–C$_4$ alkyl, —CO$_2$H, —CO$_2$(unsubstituted C$_1$–C$_4$ alkyl), —CONH$_2$, —CONH(unsubstituted C$_1$–C$_4$ alkyl), —CON(unsubstituted C$_1$–C$_4$ alkyl)(unsubstituted C$_1$–C$_4$ alkyl), —SO$_3$H, —SO$_2$NH$_2$, —SO$_2$NH(unsubstituted C$_1$–C$_4$ alkyl) and —SO$_2$N(unsubstituted C$_1$–C$_4$ alkyl)(unsubstituted C$_1$–C$_4$ alkyl);

R$^{12}$ is selected from H, C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl;

each R$^{13}$ and R$^{14}$ are each independently selected from H, C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl, or R$^{13}$ and R$^{14}$ together with the nitrogen to which they are attached form a 4–7 membered heterocyclic ring which optionally contains one or more additional heteroatoms selected from N, O, and S; and R$^{15}$ is selected from C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl;

provided that R$^{10}$ and R$^{11}$ are not both H when Z is CH or N, Y is —O—, n is 3, m is 1 and each R$^4$, R$^5$, R$^6$, R$^7$ are H, W$^3$ is H, p is 0 or p is 1 or 2 and R$^1$ and R$^2$ are each H, k is 0 or k is 1 and R$^3$ is halo or C$_1$–C$_4$ alkoxy, q is 0 or q is 1 or 2 and R$^8$ and R$^9$ are each H, Q is unsubstituted phenyl or Het, or phenyl substituted by one or more substituents selected from halo, —CH$_3$, —CH$_2$CH$_3$, —CF$_3$, —OC$_1$–C$_4$ alkyl, —OCH$_2$CH$_2$OH, —OCF$_3$, —OCF$_2$H, —SCH$_3$, —SCF$_3$, —SO$_2$CH$_3$, —CO$_2$H, —CO$_2$CH$_3$, —OH, —OCH$_2$CO$_2$H, —CH$_2$CONH$_2$, —NO$_2$, —CN, —N(CH$_3$)$_2$, and —NHC(O)CH$_3$, or Het substituted by one or more substituents selected from: —C$_1$–C$_3$ alkyl, —OC$_1$–C$_4$ alkyl, —CH$_2$OH, —CO$_2$H, —CO$_2$CH$_2$CH$_3$, —CO$_2$-tert-C$_4$H$_9$ alkyl, —CO$_2$CH$_2$-phenyl, —CONH$_2$, —C(O)phenyl, —C(O)CH$_3$, —CH$_2$CH$_2$-phenyl, and oxo, t is 0, and W$^1$ and W$^2$ are each independently selected from unsubstituted cyclohexyl and unsubstituted phenyl;

or a pharmaceutically acceptable salt or solvate thereof.

Unless otherwise provided, each alkyl, alkoxy, alkenyl, alkynyl, cycloalkyl, aryl or Het herein is independently unsubstituted or substituted with one ore more substituents defined hereinabove.

In one embodiment of the compounds of this invention, R$^{10}$ and R$^{11}$ are each independently selected from H, C$_1$–C$_{10}$ alkyl, —C$_0$–C$_6$ alkyl-O-Ar, —C$_0$–C$_6$ alkyl-(O)$_2$C$_1$–C$_6$ alkyl, —C$_0$–C$_6$ alkyl-S(O)$_2$-Ar, —C$_0$–C$_6$ alkyl-Het or R$^{10}$ and R$^{11}$, together with the nitrogen to which they are attached, form a 4–7 membered heterocyclic ring which optionally contains one or more additional heteroatoms selected from N, O, and S. By virtue of the definitions given above for the terms "alkyl", "aryl", "Het" and "4–7 membered heterocyclic ring" this definition of R$^{10}$ and R$^{11}$ also encompasses alkyl, aryl, Het and 4–7 membered heterocyclic ring groups that are optionally substituted with the substituents specified in the definitions above.

In specific embodiments, R$^{10}$ and R$^{11}$ are each independently selected from H, C$_1$–C$_{10}$ alkyl, —C$_1$–C$_4$ alkyl-O-Ar, —C$_0$–C$_4$ alkyl-(O)$_2$C$_1$–C$_6$ alkyl, —C$_0$–C$_4$ alkyl-S(O)$_2$-Ar, and —C$_0$–C$_4$ alkyl-Het or R$^{10}$ and R$^{11}$, together with the nitrogen to which they are attached, form a 4–7 membered heterocyclic ring which optionally contains one or two additional heteroatoms selected from N and O, and wherein when said C$_0$–C$_4$ alkyl is C$_1$–C$_4$ alkyl, said C$_1$–C$_4$ alkyl is unsubstituted or substituted by one or two groups selected from —CO$_2$H and —CO$_2$(unsubstituted C$_1$–C$_6$ alkyl). In another embodiment of the compounds of this invention, R$^{10}$ and R$^{11}$ are each independently selected from H, C$_1$–C$_{10}$ alkyl, —$C_1$–$C_4$ alkyl-O-Ar, —$S(O)_2C_1$–$C_4$ alkyl, —$S(O)_2$-Ar, —$C_0$–$C_4$ alkyl-Het (where the Het group is selected from imidazolyl, thienyl (thiophenyl), morpholinyl, thiomorpholinyl, furyl, tetrahydrofuranyl, pyridyl, isoxazolyl, oxadiazolyl, triazolyl and thiazolyl) or $R^{10}$ and $R^{11}$, together with the nitrogen to which they are attached, form a substituted or unsubstituted 4–7 membered heterocyclic ring which optionally contains one additional heteroatom selected from N and O, wherein the substituted ring is substituted with $C_1$–$C_4$ alkyl, and wherein when said $C_0$–$C_4$ alkyl is $C_1$–$C_4$ alkyl, said $C_1$–$C_4$ alkyl is unsubstituted or substituted by —$CO_2H$ or —$CO_2$(unsubstituted $C_1$–$C_6$ alkyl).

More specifically, $R^{10}$ and $R^{11}$ are each independently selected from H, methyl, ethyl, imidazol-2-yl-methyl-, 5-bromo-thiophen-2-yl-methyl- (or 5-bromo-thien-2-yl-methyl-), thiophen-2-yl-methyl- (or thien-2-yl-methyl-), 2-methoxy-ethyl-, 2-dimethylamino-ethyl-, 2-morpholin-4-yl-ethyl-, 2-methoxy-1-methyl-ethyl-, 2-methoxy-ethyl-, furan-2-yl-methyl-, 3-methyl-isoxazol-5-yl-methyl-, 2-thiomorpholinyl-ethyl-, 2-pyrrolidin-1-yl-ethyl-, pyridin-3-yl-methyl-, 2-pyridin-2-yl-ethyl-, 3-phenoxy-ethyl-, 3-isopropoxy-propyl-, 3-methoxy-propyl-, 5-methyl-[1,3,4]oxadiazol-2-yl-methyl-, 4-methyl-thiazol-2-yl-methyl-, 1-thiophen-2-yl-ethyl-, thiophen-3-yl-methyl-5-methyl-4H-[1,2,4]triazol-3-yl-methyl-, pyridin-2-yl-methyl-, tetrahydrofuran-2-yl-methyl-, 1-ethyl-pyrrolidin-2-yl-methyl-, octyl, decyl, 2-(2-hydroxy-ethoxy)-ethyl-, 1-carboxy-thiophen-2-yl-methyl- (or 1-carboxy-thien-2-yl-methyl-), phenyl, methyl-sulfonyl-(mesyl), phenyl-sulfonyl-(benzene sulfonyl), or $R^{10}$ and $R^{11}$, together with the nitrogen to which they are attached, form an azetidinly, pyrrolidinyl, piperidnyl, azepanyl, 4-methyl-piperazin-1-yl, or morpholin-4-yl group.

In other embodiments, each $R^1$ and $R^2$ are each independently selected from H, $C_1$–$C_4$ alkyl and —$C_0$–$C_4$ alkyl-$OR^{11}$. By virtue of the definitions given above for the term "alkyl", this definition of $R^3$ also encompasses alkyl groups that are optionally substituted with the substituents specified in the definitions above. Accordingly, in the compounds and methods of this invention, each $R^1$ and $R^2$ may be independently selected from H, $C_1$–$C_4$ alkyl, —OH, —$C_1$–$C_4$ alkyl-OH, —$C_1$–$C_4$ alkyl-$NH_2$, —$C_1$–$C_4$ alkyl-NH($C_1$–$C_4$ alkyl), and —$C_1$–$C_4$ alkyl-N($C_1$–$C_4$ alkyl)($C_1$–$C_4$ alkyl). In a specific embodiment of the compounds of this invention, $R^1$ and $R^2$ are H.

In specific embodiments, the compounds of this invention are defined wherein p is 0–3. In preferred embodiments, p is 0, 1 or 2.

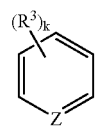

The group describes a 6-membered aromatic ring, specifically, a phenyl or pyridyl ring, which may be unsubstituted (k=0) or substituted by one or more substituents $R^3$. In a preferred embodiment, the compounds of this invention are defined where Z is CH. The total number of $R^3$ substituents that may be present in a compound of this invention is represented by "k". When Z is $CR^3$, k is 0–4, meaning that there can be up to four $R^3$ substituents on the 6-membered aromatic ring. When Z is CH or N, k is 0–3, meaning that there can be up to three $R^3$ substituents on the 6-membered aromatic ring. In this embodiment, $R^3$ is not attached to the Z moiety (N or C atom) of the ring. Preferably, k is 0 or 1.

In the embodiments wherein k is 1 or more, each $R^3$ may be the same or different and may be independently selected from halo, $C_1$–$C_4$ alkyl and $C_1$–$C_4$ alkoxy. By virtue of the definitions given above for the term "alkyl", this definition of $R^3$ also encompasses alkyl groups that are optionally substituted with the substituents specified in the definitions above.

When the moiety —$Y(CR^4R^5)_n$— is substituted and $R^4$ and $R^5$ are different on at least one $(CR^4R^5)$ moiety (e.g., when one of $R^4$ or $R^5$ is methyl and the other of $R^4$ and $R^5$ is hydrogen) a chiral compound is obtained. All single stereoisomers, mixtures and racemates of these chiral compounds are intended to be encompassed within the broad scope of the present invention.

In another embodiment, the compounds of this invention are defined wherein n is 2–4. In specific embodiments, n is 3.

In specific embodiments of the compounds this invention, q is 1 and $R^8$ and $R^9$ are both H.

In the compounds of this invention, t may be 0 or 1. When Z is CH or $CR^3$ and t is 1, the compound of this invention is the N-oxide of the tertiary amine, having the formula:

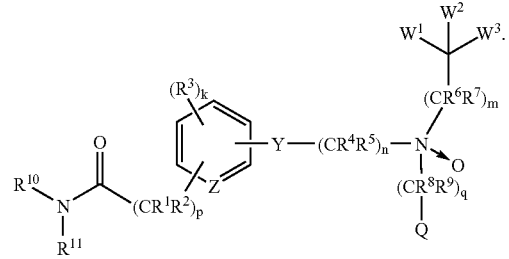

When Z is N, CH or $CR^3$ and t is 0, the compound of this invention is the tertiary amine having the formula:

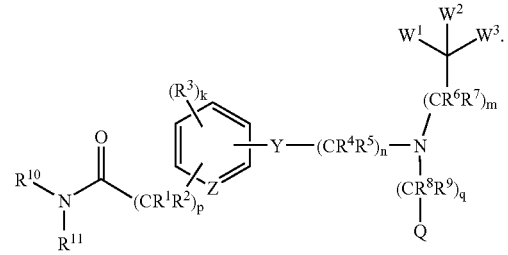

Group Q is selected from $C_3$–$C_7$ cycloalkyl, aryl and Het. By virtue of the definitions given above for the terms "cycloalkyl", "aryl" and "Het", this definition of Q also encompasses cycloalkyl, aryl and Het groups that are optionally substituted from 1 to 4 times, more preferably, from 1 to 3 times with the substituents specified in the definitions above. In one embodiment, Q is an aryl group. In specific non-limiting embodiments, Q is a substituted phenyl group, containing two substituents selected from halo and $C_1$–$C_4$ alkyl; specifically $C_1$–$C_4$ haloalkyl. More specifically, Q is a 2-chloro-3-(trifluoromethyl)phenyl group.

In one embodiment of the compounds of this invention, m is 0 or 1 and $R^6$ and $R^7$ are each independently selected from H and $C_1$–$C_4$ alkyl. In another embodiment, $W^3$ is H. In yet another embodiment, $W^1$ and $W^2$ are the same or different $W^1$ is selected from $C_3$–$C_6$ cycloalkyl, aryl and Het and $W^2$ is selected from $C_1$–$C_4$ alkyl, $C_3$–$C_6$ cycloalkyl, aryl and Het. In another embodiment, m is 1, $R^6$ and $R^7$ are both H, $W^3$ is H, $W^1$ is selected from $C_3$–$C_6$ cycloalkyl, aryl and Het and $W^2$ is selected from —$CO_2R^{10}$, —$NR^{11}R^{12}$, —$CONR^{11}R^{12}$, —$OCOR^{13}$, —$OCONR^{11}R^{12}$, $C_1$–$C_4$ alkyl, —$C_0$–$C_4$ alkyl-$OR^{10}$, —$C_1$–$C_4$ alkyl-Het, —$C_1$–$C_4$ alkyl-Ar and —$C_1$–$C_4$ alkyl-$C_3$–$C_6$ cycloalkyl. In other embodiments of the compounds of this invention, m is 0 or m is 1 and $R^6$ and $R^7$ are both H, $W^1$ is selected from $C_3$–$C_6$ cycloalkyl, aryl and Het and $W^2$ and $W^3$ are each H. By virtue of the definitions given above, for the terms "alkyl", "cycloalkyl", "aryl" and "Het", $W^1$ and $W^2$ also encompasses the foregoing groups optionally substituted with the substituents specified in the definitions above. In one embodiment, $W^1$ and/or $W^2$ may be phenyl, thienyl, pyridyl, furanyl, pyrrolyl, morpholinyl, or pyrrolidinyl, where each phenyl, thienyl, pyridyl, furanyl, pyrrolyl, morpholinyl, or pyrrolidinyl may be optionally substituted from 1 to 3 times, more preferably from 1 to 2 times with one or more of the substituents defined hereinabove. For example, $W^1$ and/or $W^2$ may be each independently substituted by one or more substituents independently selected from $C_1$–$C_4$ alkyl, —OH, halo, —O—$C_1$–$C_4$ alkyl, and —$C_1$–$C_4$ haloalkyl. In another embodiment, $W^1$ may be phenyl, thienyl, pyridyl, furanyl, pyrrolyl, morpholinyl, or pyrrolidinyl and $W^2$ may be phenyl, thienyl, pyridyl, furanyl, pyrrolyl, morpholinyl, pyrrolidinyl, cyclohexyl, cyclopentyl, $C_1$–$C_4$ alkyl (such as methyl, ethyl, n-propyl, iso-propyl, n-butyl, iso-butyl, tert-butyl and sec-butyl) or $C_1$–$C_4$ haloalkyl, where each phenyl, thienyl, pyridyl, furanyl, pyrrolyl, morpholinyl, or pyrrolidinyl may be optionally independently substituted with 1, 2 or 3 substituents independently selected from $C_1$–$C_4$ alkyl, —OH, halo, —O—$C_1$–$C_4$ alkyl, and —$C_1$–$C_4$ haloalkyl. In specific embodiments of this invention, m is 1 and $R^6$ and $R^7$ are both H, $W^3$ is H, $W^1$ and $W^2$ are aryl or $W^1$ is aryl and $W^2$ is aryl or $C_1$–$C_4$ alkyl. In specific embodiments of this invention, m is 1, $R^6$ and $R^7$ are both H, $W^3$ is H, $W^1$ and $W^2$ are each unsubstituted phenyl or $W^1$ is unsubstituted phenyl and $W^2$ is $C_1$–$C_4$ alkyl, specifically methyl.

In other embodiments of this invention, unless otherwise specified, the —$C_0$–$C_8$ alkyl-, —$C_0$–$C_6$ alkyl- and —$C_0$–$C_4$ alkyl-moieties of the substituents defined herein are unsubstituted —$C_0$–$C_8$ alkyl-, unsubstituted —$C_0$–$C_6$ alkyl- and unsubstituted —$C_0$–$C_4$ alkyl-moieties, respectively.

It is to be understood that the present invention covers all combinations of particular and preferred groups described herein above.

Specific embodiments of this invention comprise compounds of Formulas I, II, I-A or II-A wherein $R^1$, $R^2$, $R^3$, $R^6$, $R^7$, $R^8$, $R^9$ and $W^3$ are each H; $R^4$ and $R^5$ are each independently selected from H and $C_1$–$C_4$ alkyl, $R^{10}$ and $R^{11}$ are each independently selected from H, $C_1$–$C_{10}$ alkyl, —$C_1$–$C_4$ alkyl-O-Ar, —$S(O)_2C_1$–$C_4$ alkyl, —$S(O)_2$-Ar, —$C_0$–$C_4$ alkyl-Het, where the Het group is selected from imidazolyl, thienyl (thiophenyl), morpholinyl, thiomorpholinyl, furyl, tetrahydrofuranyl, pyridyl, isoxazolyl, oxadiazolyl, triazolyl and thiazolyl; or $R^{10}$ and $R^{11}$, together with the nitrogen to which they are attached, from a substituted or unsubstituted 4–7 membered heterocyclic ring which optionally contains one additional heteroatom selected from N and O, wherein the substituted ring is substituted with $C_1$–$C_4$ alkyl, wherein when said $C_0$–$C_4$ alkyl is $C_1$–$C_4$ alkyl, said $C_1$–$C_4$ alkyl is unsubstituted or substituted by —$CO_2H$ or —$CO_2$(unsubstituted $C_1$–$C_6$ alkyl); Z is CH; Y is —O— or —C($R^4$)($R^5$)—; Q is a substituted phenyl group, containing two substituents selected from halo and $C_1$–$C_4$ haloalkyl; p is 0, 1 or 2; n is 3; m is 0 or 1; q is 1; k is 0; t is 0; and $W^1$ and $W^2$ are aryl or $W^1$ is aryl and $W^2$ is aryl or $C_1$–$C_4$ alkyl; or a pharmaceutically acceptable salt or solvate thereof.

More specific embodiments of this invention comprise compounds of Formulas I, II, I-A or II-A wherein $R^1$, $R^2$, $R^3$, $R^6$, $R^7$, $R^8$, $R^9$ and $W^3$ are each H; $R^4$ and $R^5$ are each independently selected from H and methyl; $R^{10}$ and $R^{11}$ are each independently selected from H, methyl, ethyl, imidazol-2-yl-methyl-, 5-bromo-thiophen-2-yl-methyl- (or 5-bromo-thien-2-yl-methyl-), thiophen-2-yl-methyl- (or thien-2-yl-methyl-), 2-methoxy-ethyl-, 2-dimethylamino-ethyl-, 2-morpholin-4-yl-ethyl-, 2-methoxy-1-methyl-ethyl-, 2-methoxy-ethyl-, furan-2-yl-methyl-, 3-methyl-isoxazol-5-yl-methyl-, 2-thiomorpholin-4-yl-ethyl-, 2-pyrrolidin-1-yl-ethyl-, pyridin-3-yl-methyl-, 2-pyridin-2-yl-ethyl-, 3-phenoxy-ethyl-, 3-isopropoxy-propyl-, 3-methoxy-propyl-, 5-methyl-[1,3,4]oxadiazol-2-yl-methyl-, 4-methyl-thiazol-2-yl-methyl-, 1-thiophen-2-yl-ethyl-, thiophen-3-yl-methyl-5-methyl-4H-[1,2,4]triazol-3-yl-methyl-, pyridin-2-yl-methyl-, tetrahydrofuran-2-yl-methyl-, 1-ethyl-pyrrolidin-2-yl-methyl-, octyl, decyl, 2-(2-hydroxy-ethoxy)-ethyl-, 1-carboxy-thiophen-2-yl-methyl- (or 1-carboxy-thien-2-yl-methyl-), phenyl, methyl-sulfonyl-(mesyl), phenyl-sulfonyl-(benzene sulfonyl), or $R^{10}$ and $R_{11}$, together with the nitrogen to which they are attached, form an azetidinly, pyrrolidinyl, piperidnyl, azepanyl, 4-methyl-piperazin-1-yl, or morpholin-4-yl group; Z is CH; Y is —O—; Q is 2-chloro-3-(trifluoromethyl)phenyl; p is 1; n is 3; q is 1; k is 0; t is 0; m is 1; and $W^1$ and $W^2$ are each unsubstituted phenyl or $W^1$ is unsubstituted phenyl and $W^2$ is methyl; or a pharmaceutically acceptable salt or solvate thereof.

In another specific non-limiting embodiment of the compounds of this invention, $R^1$ and $R^2$ are H.

Particular embodiments of this invention are directed to a compound of Formula I, II, I-A or II-A, as defined above, wherein at least one of Y, $W^1$, $W^2$, $W^3$, t, $R^1$, $R^2$, $R^4$, $R^5$, $R^6$, $R^7$, $R^8$, $R^9$, $R^{10}$ or $R^{11}$ is defined as follows:

wherein:

Y is —S—, —N($R^{12}$)—, or —C($R^4$)($R^5$)—; or $W^1$ is $C_1$–$C_6$ alkyl or Het, optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}C(O)OR^{15}$, —$C_0$–$C_6$ alkyl-$NR^{13}C(O)NR^{13}R^{14}$, and —$C_0$–$C_6$ alkyl-$NR^{13}COR^{15}$, where said $C_1$–$C_6$ alkyl, is optionally unsubstituted or substituted by one or more halo substituents; or $W^2$ is H, halo, $C_1$–$C_6$ alkyl, $C_2$–$C_6$ alkenyl, $C_2$–$C_6$ alkynyl, —$C_0$–$C_6$ alkyl $NR^{13}R^{14}$, —$C_0$–$C_6$ alkyl-$SR^{12}$, —$C_0$–$C_6$ alkyl-$OR^{12}$, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$OCOR^{15}$, —$C_0$–$C_6$ alkyl-$OCONR^{13}R^{14}$, —$C_0$–$C_6$ alkyl-$NR^{13}CONR^{13}R^{14}$, —$C_0$–$C_6$ alkyl-$NR^{13}COR^{15}$, —$C_0$–$C_6$ alkyl-Het, —$C_1$–$C_6$ alkyl-Ar or —$C_1$–$C_6$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_6$ alkyl-Het, —$C_1$–$C_6$ alkyl-Ar and —$C_1$–$C_6$ alkyl-$C_3$–$C_7$ cycloalkyl are optionally unsubstituted or substituted with one or more groups independently selected from halo, cyano, nitro, —$C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-C(O)$OR^{15}$, —$C_0$–$C_6$ alkyl-$NR^{13}$C(O)$OR^{15}$, —$C_0$–$C_6$ alkyl-$NR^{13}$C(O)$NR^{13}R^{14}$, and —$C_0$–$C_6$ alkyl-$NR^{13}COR^{15}$, where said $C_1$–$C_6$ alkyl, is optionally unsubstituted or substituted by one or more halo substituents; or $W^3$ is halo, $C_1$–$C_6$ alkyl, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$OCOR^{15}$, —$C_0$–$C_6$ alkyl-$OCONR^{13}R^{14}$, —$C_0$–$C_6$ alkyl-$NR^{13}CONR^{13}R^{14}$, —$C_0$–$C_6$ alkyl-$NR^{13}COR^{15}$, —$C_0$–$C_6$ alkyl-Het, —$C_1$–$C_6$ alkyl-Ar or —$C_1$–$C_6$ alkyl-$C_3$–$C_7$ cycloalkyl, wherein said $C_1$–$C_6$ alkyl is optionally unsubstituted or substituted by one or more halo substituents; or t is 1; or at least one $R^1$ or $R^2$ is halo, $C_3$–$C_6$ alkenyl, $C_3$–$C_6$ alkynyl, —$C_0$–$C_6$ alkyl-$NR^{13}R^{14}$, —$C_1$–$C_6$ alkyl-$OR^{12}$, —$C_1$–$C_6$ alkyl-$SR^{12}$, —$C_1$–$C_6$ alkyl-Het, —$C_1$–$C_6$ alkyl-Ar and —$C_1$–$C_6$ alkyl-$C_3$–$C_7$ cycloalkyl, or $R^1$ and $R^2$ together with the carbon to which they are attached form a 3–5 membered carbocyclic or heterocyclic ring, wherein said heterocyclic ring contains one, or more heteroatoms selected from N, O, and S, where any of said $C_1$–$C_6$ alkyl is optionally unsubstituted or substituted by one or more halo substituents; or at least one $R^4$ or $R^5$ is halo, $C_1$–$C_6$ alkyl, —$C_0$–$C_6$ alkyl-Het, —$C_0$–$C_6$ alkyl-Ar or —$C_0$–$C_6$ alkyl-$C_3$–$C_7$ cycloalkyl; or at least one $R^6$ or $R^7$ is halo, $C_1$–$C_6$ alkyl, —$C_0$–$C_6$ alkyl-Het, —$C_0$–$C_6$ alkyl-Ar or —$C_0$–$C_6$ alkyl-$C_3$–$C_7$ cycloalkyl; or at least one of $R^8$ or $R^9$ is halo, —$C_0$–$C_6$ alkyl-Het, —$C_0$–$C_6$ alkyl-Ar or —$C_0$–$C_6$ alkyl-$C_3$–$C_7$ cycloalkyl; or at least one of $R^{10}$ and $R^{11}$ is $C_1$–$C_{12}$ alkyl, $C_3$–$C_{12}$ alkenyl, $C_3$–$C_{12}$ alkynyl, —$C_0$–$C_8$ alkyl-Ar, —$C_0$–$C_8$ alkyl-Het, —$C_0$–$C_8$ alkyl-$C_3$–$C_7$ cycloalkyl, —$C_0$–$C_8$ alkyl-O-Ar, —$C_0$–$C_8$ alkyl-O-Het, —$C_0$–$C_8$ alkyl-O—$C_3$–$C_7$ cycloalkyl, —$C_0$–$C_8$ alkyl-S(O)$_x$—$C_1$–$C_6$ alkyl, —$C_0$–$C_8$ alkyl-S(O)$_x$-Ar, —$C_0$–$C_8$ alkyl-S(O)$_x$-Het, —$C_0$–$C_8$ alkyl-S(O)$_x$—$C_3$–$C_7$ cycloalkyl, —$C_0$–$C_8$ alkyl-NH-Ar, —$C_0$–$C_8$ alkyl-NH-Het, —$C_0$–$C_8$ alkyl-NH—$C_3$–$C_7$ cycloalkyl, —$C_0$–$C_8$ alkyl-N($C_1$–$C_4$ alkyl)-Ar, —$C_0$–$C_8$ alkyl-N($C_1$–$C_4$ alkyl)-Het, —$C_0$–$C_8$ alkyl-N($C_1$–$C_4$ alkyl)-$C_3$–$C_7$ cycloalkyl, —$C_0$–$C_8$ alkyl-Ar, —$C_0$–$C_8$ alkyl-Het or —$C_0$–$C_8$ alkyl-$C_3$–$C_7$ cycloalkyl, where x is 0, 1 or 2, or $R^{10}$ and $R^{11}$, together with the nitrogen to which they are attached, form a 4–7 membered heterocyclic ring which optionally contains one or more additional heteroatoms selected from N, O, and S, wherein said $C_1$–$C_6$ alkyl is optionally substituted by one or more of the substituents independently selected from the group halo, —OH, —SH, —$NH_2$, —NH(unsubstituted $C_1$–$C_6$ alkyl), —N(unsubstituted $C_1$–$C_6$ alkyl)(unsubstituted $C_1$–$C_6$ alkyl), unsubstituted —O$C_1$–$C_6$ alkyl, —$CO_2H$, —$CO_2$(unsubstituted $C_1$–$C_6$ alkyl), —$CONH_2$, —CONH(unsubstituted $C_1$–$C_6$ alkyl), —CON(unsubstituted $C_1$–$C_6$ alkyl)(unsubstituted $C_1$–$C_6$ alkyl), —$SO_3H$, —$SO_2NH_2$, —$SO_2NH$(unsubstituted $C_1$–$C_6$ alkyl) and —$SO_2N$(unsubstituted $C_1$–$C_6$ alkyl)(unsubstituted $C_1$–$C_6$ alkyl). Other specific embodiments of this invention comprise a compound of Formula I, II, I-A or II-A, wherein at least one of $R^4$, $R^5$, $R^{10}$, $R^{11}$, or $W^2$ is defined as follows, wherein:

at least one of $R^4$, $R^5$, $R^{10}$ or $R^{11}$ is not H, or $W^2$ is $C_1$–$C_4$ alkyl or Het. Yet other specific embodiments of this invention comprise a compound of Formula I, II, I-A or II-A, wherein at least one of $R^{10}$, $R^{11}$ or $W^2$ is defined as follows, wherein at least one of $R^{10}$ or $R^{11}$ is not H, or $W^2$ is $C_1$–$C_4$ alkyl or Het.

Another particular embodiment of this invention is directed to a compound of Formula I, I-A, II or II-A, as defined above, provided that $R^{10}$ and $R^{11}$ are not both H when: Z is CH, $CR^3$ or N, wherein when Z is CH or $CR^3$, k is 0–4 and when Z is N, k is 0–3; Y is —O—; $W^1$ and $W^2$ are each independently $C_3$–$C_8$ cycloalkyl or aryl; wherein said $C_3$–$C_8$ cycloalkyl and Ar are optionally unsubstituted or substituted as defined herein; Q is $C_3$–$C_8$ cycloalkyl, Ar or 4–8 membered Het; wherein said $C_3$–$C_8$ cycloalkyl, Ar or Het are optionally unsubstituted or substituted as defined herein; $W^3$ is H; p is 0–6; n is 2–8; m is 0 or 1; q is 0 or 1; t is 0; each $R^1$ and $R^2$ are independently H, $C_1$–$C_6$ alkyl, —O$C_1$–$C_6$ alkyl or —S$C_1$–$C_6$ alkyl; each $R^3$ is the same or different and is independently halo, cyano, nitro, $C_1$–$C_6$ alkyl, $C_3$–$C_6$ alkenyl, —O$C_1$–$C_6$ alkyl, —$C_0$–$C_6$ alkyl-$CO_2R_{12}$, —$COR^{15}$, —$SR^{12}$, —$SOR^{15}$, —$SO_2R^{12}$ (where $R^{12}$ is H, $C_1$–$C_6$ alkyl or $C_3$–$C_6$ alkenyl and $R^{15}$ is $C_1$–$C_6$ alkyl or $C_3$–$C_6$ alkenyl), —OCO$C_1$–$C_6$ alkyl, —OC(O)$NR^{13}R^{14}$, —$CONR^{13}R^{14}$, —$C_0$–$C_6$ alkyl-$NR^{13}R^{14}$ (where each $R^{13}$ and each $R^{14}$ are independently selected from H, $C_1$–$C_6$ alkyl, $C_3$–$C_6$ alkenyl, and $C_3$–$C_6$ alkynyl) or a 5–6 membered Het; each $R^4$, $R^5$, $R^6$, $R^7$ and $R^8$ are H; and $R^9$ is H or $C_1$–$C_6$ alkyl;

Compounds of Formulas I, II, I-A or II-A according to this invention include:

2-(3-{3-[(2-chloro-3-(trifluoromethyl)-benzyl)-(2,2-diphenylethyl)-amino]-propoxy}phenyl)-1-morpholin-4-yl-ethanone;

2-(3-{3-[(2-chloro-3-(trifluoromethyl)-benzyl)-(2,2-diphenylethyl)-amino]-propoxy}phenyl)-N-methyl-acetamide;

2-(3-{3-[(2chloro-3-(trifluoromethyl)-benzyl)-(2,2-diphenylethyl)-amino]-propoxy}phenyl)-N,N-dimethyl-acetamide;

2-(3-{3-[(2-chloro-3-(trifluoromethyl)-benzyl)-(2,2-diphenylethyl)-amino]-propoxy}phenyl)-1-piperidyn-1-yl-ethanone;

2-(3-{3-[(2-chloro-3-(trifluoromethyl)-benzyl)-(2,2-diphenylethyl)-amino]-propoxy}phenyl)-1-(4-methyl-piperazin-1-yl)-ethanone;

2-(3-{3-[(2-chloro-3-(trifluoromethyl)-benzyl)-(2,2-diphenylethyl)-amino]-propoxy}phenyl)-1-pyrrolidin-1-yl-ethanone;

2-(3-{3-[(2-chloro-3-trifluoromethyl)-benzyl)-(2,2-diphenylethyl)-amino]-propoxy}phenyl)-N-ethyl-acetamide;

2-(3-{3-[(2-chloro-3-(trifluoromethyl)-benzyl)-(2,2-diphenylethyl)-amino]-propoxy}phenyl)-N,N-diethyl-acetamide;

2-(3-{3-[(2-chloro-3-(trifluoromethyl)-benzyl)-(2,2-diphenylethyl)-amino]-propoxy}phenyl)-1-azetidin-1-yl-ethanone;

2-(3-{3-[(2-chloro-(trifluoromethyl)-benzyl)-(2,2-diphenylethyl)-amino]-propoxy}phenyl)-1-azepan-1-yl-ethanone;

(S)-2-(3-{3-[[2-chloro-3-(trifluoromethylbenzyl](2-phenylpropyl)amino]propoxy}-phenyl)-acetamide;

2-(3-{3-[(2-chloro-3-trifluoromethyl-benzyl)-diphenylethyl-amino]-propoxy}-phenyl)-N-(1H-imidazol-2-ylmethyl)-acetamide;

N-(5-bromo-thiophen-2-ylmethyl)-2-3-{3-[(2-chloro-3-trifluoromethyl-benzyl)-diphenylethyl-amino]-propoxy}-phenyl)-acetamide;

2-(3-{3-[(2-chloro-3-trifluoromethyl-benzyl)-diphenyl-ethyl-amino]-propoxy}-phenyl)-N-thiophen-2-ylmethyl-acetamide;

2-(3-{3-[(2-chloro-3-trifluoromethyl-benzyl)-diphenyl-ethyl-amino]-propoxy}-phenyl)-N-(2-methoxy-ethyl)-acetamide;

2-(3-{3-[(2-chloro-3-trifluoromethyl-benzyl)-diphenyl-ethyl-amino]-propoxy}-phenyl)-N-(2-dimethylamino-ethyl)-acetamide;

2-(3-{3-[(2-chloro-3-trifluoromethyl-benzyl)-diphenyl-ethyl-amino]-propoxy}-phenyl)-N-(2-morpholin-4-yl-ethyl)-acetamide;

2-(3-{3-[(2-chloro-3-trifluoromethyl-benzyl)-diphenyl-ethyl-amino]-propoxy}-phenyl)-N-(2-methoxy-1-methyl-ethyl)-acetamide;

2-(3-{3-[(2-chloro-3-trifluoromethyl-benzyl)-diphenyl-ethyl-amino]-propoxy}-phenyl)-N-(2-methoxy-ethyl)-N-methyl-acetamide;

2-(3-{3-[(2-chloro-3-trifluoromethyl-benzyl)-diphenyl-ethyl-amino]-propoxy}-phenyl)-N,N-bis-(2-methoxy-ethyl)-acetamide;

2-(3-{3-[(2-chloro-3-trifluoromethyl-benzyl)-diphenyl-ethyl-amino]-propoxy}-phenyl)-N-furan-2-ylmethyl-acetamide;

2-(3-{3-[(2-chloro-3-trifluoromethyl-benzyl)-diphenyl-ethyl-amino]-propoxy}-phenyl)-N-(3-methyl-isoxazol-5-ylmethyl)-acetamide;

2-(3-{3-[(2-chloro-3-trifluoromethyl-benzyl)-diphenyl-ethyl-amino]-propoxy}-phenyl)-N-(2-thiomorpholin-4-yl-ethyl)-acetamide;

2-(3-{3-[(2-chloro-3-trifluoromethyl-benzyl)-diphenyl-ethyl-amino]-propoxy}-phenyl)-N-(2-pyrrolidin-1-yl-ethyl)-acetamide;

2-(3-{3-[(2-chloro-3-trifluoromethyl-benzyl)-diphenyl-ethyl-amino]-propoxy}-phenyl)-N-pyridin-3-ylmethyl-acetamide;

2-(3-{3-[(2-chloro-3-trifluoromethyl-benzyl)-diphenyl-ethyl-amino]-propoxy}-phenyl)-N-2-pyridin-2-yl-ethyl)-acetamide;

2-(3-{3-[(2-chloro-3-trifluoromethyl-benzyl)-diphenyl-ethyl-amino]-propoxy}-phenyl)-N-(3-phenoxy-ethyl)-acetamide;

2-(3-{3-[(2-chloro-3-trifluoromethyl-benzyl)-diphenyl-ethyl-amino]-propoxy}-phenyl)-N-(3-isopropoxy-propyl)-acetamide;

2-(3-{3-[(2-chloro-3-trifluoromethyl-benzyl)-diphenyl-ethyl-amino]-propoxy}-phenyl)-N-(3-methoxy-propyl)-acetamide;

2-(3-{3-[(2-chloro-3-trifluoromethyl-benzyl)-diphenyl-ethyl-amino]-propoxy}-phenyl)-N-(5-methyl-[1,3,4]oxadiazol-2-ylmethyl)-acetamide;

2-(3-{3-[(2-chloro-3-trifluoromethyl-benzyl)-diphenyl-ethyl-amino]-propoxy}-phenyl)-N-(4-methyl-thiazol-2-ylmethyl)-acetamide;

2-(3-{3-[(2-chloro-3-trifluoromethyl-benzyl)diphenylethyl-amino]-propoxy}-phenyl)-N-(1-thiophen-2-yl-ethyl)-acetamide;

2-(3-{3-[(2-chloro-3-trifluoromethyl-benzyl)-diphenyl-ethyl-amino]-propoxy}-phenyl)-N-thiophen-3-ylmethyl-acetamide;

2-(3-{3-[(2-chloro-3-trifluoromethyl-benzyl)-diphenyl-ethyl-amino]-propoxy}-phenyl)-N-(5-methyl-4H-[1,2,4]triazol-3-ylmethyl)-acetamide;

2-3-{3-[(2-chloro-3-trifluoromethyl-benzyl)-diphenylethyl-amino]-propoxy}-phenyl)-N-pyridin-2-ylmethyl-acetamide;

2-(3-{3-[(2-chloro-3-trifluoromethyl-benzyl)-diphenyl-ethyl-amino]-propoxy}-phenyl)-N-(tetrahydro-furan-2-ylmethyl)-acetamide;

2-(3-{3-[(2-chloro-3-trifluoromethyl-benzyl)diphenylethyl-amino]-propoxy}-phenyl)-N-(1-ethyl-pyrrolidin-2-ylmethyl)-acetamide;

2-(3-{3-[(2-chloro-3-trifluoromethyl-benzyl)-diphenyl-ethyl-amino]-propoxy}-phenyl)-N-octyl-acetamide;

2-(3-{3-[(2-chloro-3-trifluoromethyl-benzyl)-diphenyl-ethyl-amino]-propoxy}-phenyl)-N-decyl-acetamide;

2-(3-{3-[(2-chloro-3-trifluoromethyl-benzyl)-diphenyl-ethyl-amino]-propoxy}-phenyl)-N-[2-(2-hydroxy-ethoxy)-ethyl]-acetamide;

[2-(3-{3-[(2-chloro-3-trifluoromethyl-benzyl)-diphenyl-ethyl-amino]-propoxy}-phenyl)-ethanoylamino]-2-thiophen-2-yl-acetic acid;

3-[2-(3-{3-[(2-chloro-3-trifluoromethyl-benzyl)-diphenyl-ethyl-amino]-propoxy}-phenyl)-ethanoylamino]-propionic acid;

3-[2-(3-{3-[(2-chloro-3-trifluoromethyl-benzyl)-diphenyl-ethyl-amino]-propoxy}-phenyl)-ethanoylamino]-acetic acid;

(R)-2-(3-{3-[(2-chloro-3-(trifluoromethyl)-benzyl)-(2,2-diphenylethyl)-amino]-2-methyl-propoxy}phenyl)-1-morpholin-4-yl-ethanone;

2-(3-{(R)-3-[(2-chloro-3-trifluoromethyl-benzyl)-diphenyl-ethyl-amino]-butoxy}-phenyl)-1-morpholin-4-yl-ethanone;

4-{3-[(2-chloro-3-trifluoromethyl-benzyl)-diphenylethyl-amino]-propoxy}-N,N-dimethyl-benzamide;

1-(4-{3-[(2-chloro-3-trifluoromethyl-benzyl)-diphenyl-ethyl-amino]-propoxy}-phenyl)-1-morpholin-4-yl-methanone;

1-(4-{3-[(2-chloro-3-trifluoromethyl-benzyl)-diphenyl-ethyl-amino]-propoxy}-phenyl)-1-(4-methyl-piperazin-1-yl)-methanone;

3-{3-[(2-chloro-3-trifluoromethyl-benzyl)-diphenylethyl-amino]-propoxy}-N,N-dimethyl-benzamide;

3-{3-[(2-chloro-3-trifluoromethyl-benzyl)-diphenylethyl-amino]-propoxy}N-phenyl-benzamide;

1-(3-{3-[(2-chloro-3-trifluoromethyl-benzyl)-diphenyl-ethyl-amino]-propoxy}-phenyl)-1-morpholin-4-yl-methanone;

1-(3-{3-[(2-chloro-3-trifluoromethyl-benzyl)-diphenyl-ethyl-amino]-propoxy}-phenyl)-1-(4-methyl-piperazin-1-yl)-methanone;

N-[1-(3-{3-[(2-chloro-3-trifluoromethyl-benzyl)-diphenyl-ethyl-amino]-propoxy}-phenyl)-methanoyl]-methanesulfonamide;

N-[1-(3-{3-[(2-chloro-3-trifluoromethyl-benzyl)-diphenyl-ethyl-amino]-propoxy}-phenyl)-methanoyl]-benzenesulfonamide;

N-[2-(3-{3-[(2-chloro-3-trifluoromethyl-benzyl)-diphenyl-ethyl-amino]-propoxy}-phenyl)-ethanoyl]-methanesulfonamide;

N-[2-(3-{3-[(2-chloro-3-trifluoromethyl-benzyl)-diphenyl-ethyl-amino]-propoxy}-phenyl)-ethanoyl]-benzenesulfonamide N-[-(3-{3-[(2-chloro-3-trifluoromethyl-benzyl)-diphenyl-ethyl-amino]-propoxy}-phenyl-ethanoyl]-N-methylbenzenesulfonamide;

N-[2-(3-{3-[(chlorotrifluoromethyl-benzyl)-diphenylethyl-amino]-propoxy}-phenyl)-ethanoyl]-N-methyl-methanesulfonamide;

2-(3-{3-[(2-chloro-3-trifluoromethyl-benzyl)-((S)-2-phenyl-propyl)-amino]-propoxy}-phenyl)-1-morpholinyl-4-yl-ethanone;

2-(3-{3-[(2-chloro-3-trifluoromethyl-benzyl)-((S)-2-phenyl-propyl)-amino]-propoxy}-phenyl)-N-ethyl-acetamide;

2-(3-{3-[(2-chloro-3-trifluoromethyl-benzyl)-((R)-2-phenyl-propyl)-amino]-propoxy}-phenyl)-N,N-dimethyl-acetamide;

2-(3-{3-[(2-chloro-3-trifluoromethyl-benzyl)-((R)-2-phenyl-propyl)-amino]-propoxy}-phenyl)acetamide;

2-(3-{3-[(2-chloro-3-trifluoromethyl-benzyl)-((R)-2-phenyl-propyl)-amino]-propoxy}-phenyl)-N-methyl-acetamide;

2-3-{3-[(2-chloro-3-trifluoromethyl-benzyl)-((R)-2-phenyl-propyl)-amino]-propoxy}-phenyl)-N,N-dimethyl-acetamide, and a stereoisomer, a stereoisomeric mixture or racemate thereof and a pharmaceutically acceptable salt or solvate thereof.

Preferred compounds of Formulas I, II, I-A or II-A include:

2-(3-{3-[(2-chloro-3-(trifluoromethyl)-benzyl)-(2,2-diphenylethyl)-amino]-propoxy}phenyl)-N-methyl-acetamide, 2-(3-{3-[(2-chloro-3-(trifluoromethyl)-benzyl)-(2,2-diphenylethyl)-amino]-propoxy}phenyl)-N,N-dimethyl-acetamide, 2-(3-{3-[(2-chloro-3-(trifluoromethyl)-benzyl)-(2,2-diphenylethyl)-amino]-propoxy}phenyl)-N-ethyl-acetamide, 2-(3-{3-[(2-chloro-3-trifluoromethyl-benzyl)-diphenylethyl-amino]-propoxy}-phenyl)-N,N-bis-(2-methoxyethyl)-acetamide;

2-(3-{3-[(2-chloro-3-trifluoromethyl-benzyl)-diphenylethyl-amino]-propoxy}-phenyl)-N-thiophen-3-ylmethyl-acetamide;

2-(3-{3-[(2-chloro-3-trifluoromethyl-benzyl)-((R)-2-phenyl-propyl)-amino]-propoxy}-phenyl)acetamide;

2-(3-{3-[(2-chloro-3-trifluoromethyl-benzyl)-((R)-2-phenyl-propyl)-amino]-propoxy}-phenyl)-N-methyl-acetamide;

and a stereo isomer, a stereoisomeric mixture or racemate thereof and a pharmaceutically acceptable salt or solvate thereof.

The term "LXR modulator," as used herein, means a small molecule that modulates the biological activities of LXRα and/or LXRβ. More specifically, such an LXR modulator either enhances or inhibits the biological activities of LXR. If such a modulator partially or completely enhances the biological activities of LXR, it is a partial or complete LXR agonist, respectively. If such a modulator partially or completely inhibits the biological activities of LXR, it is a partial or complete LXR agonist, respectively. Preferably, the LXR modulator compounds of this invention are LXR agonists. As used herein, the term "LXR agonist" refers to compounds which achieve at least 20% activation of LXR relative to 24(S),25-epoxycholesterol, the appropriate positive control in the HTRF assay described below in Test Method 1. It should be noted that to show activity in the specific Test Methods described herein, the LXR modulator compound must bind to the LXR nuclear receptor and recruit the specific peptide derived from the coactivator protein, SRC1, to the modulator compound-bound LXR complex. The compounds of this invention that form an LXR-modulator compound-complex may also recruit at least one or more of the other >80 known different nuclear receptor cofactors. Recruiter peptides derived from any of these other nuclear receptor cofactors may be similarly prepared and assayed according to known procedures.

The compounds of this invention are useful for a variety of medicinal purposes. The compounds of this invention may be used in methods for the prevention or treatment of LXR mediated diseases and conditions. This invention further provides compounds of this invention for use in the preparation of a medicament for the prevention or treatment of an LXR mediated disease or condition. LXR mediated diseases or conditions include inflammation, cardiovascular disease including atherosclerosis, arteriosclerosis, hypercholesteremia, and hyperlipidemia. In particular, the compounds of this invention are useful in the treatment and prevention of inflammation, cardiovascular disease including atherosclerosis and hypercholesteremia.

The present invention also provides a method for increasing reverse cholesterol transport, compounds of this invention for increasing reverse cholesterol transport and the use of compounds of this invention for the preparation of a medicament for increasing reverse cholesterol transport. Lipoprotein metabolism is a dynamic process comprised of production of triglyceride rich particles from the liver (as VLDL), modification of these lipoprotein particles within the plasma (VLDL to IDL to LDL) and clearance of the particles from the plasma, again by the liver. This process provides the transport of triglycerides and free cholesterol to cells of the body. Reverse cholesterol transport is the proposed mechanism by which peripheral cholesterol is returned to the liver from extra-hepatic tissue. The process is carried out by HDL cholesterol. The combination of lipoprotein production (VLDL, HDL) from the liver, modification of particles (all) within the plasma and subsequent clearance back to the liver, accounts for the steady state cholesterol concentration of the plasma. Without wishing to be bound by any particular theory, it is currently believed that the compounds of this invention increase reverse cholesterol transport by increasing cholesterol efflux from the arteries.

Additionally, this invention provides a method for inhibiting cholesterol absorption, compounds of this invention for inhibiting cholesterol absorption and the use of compounds of this invention for the preparation of a medicament for inhibiting cholesterol absorption. This invention also provides a method for increasing reverse cholesterol transport, compounds of this invention for increasing reverse cholesterol transport and the use of compounds of this invention for the preparation of a medicament for increasing reverse cholesterol transport.

The compounds of this invention may also be useful for the prevention or treatment of inflammation and neurodegenerative diseases or neurological disorders. Accordingly, this invention also provides a method for preventing or treating inflammation (See A. J. Fowler et al., J. Invest. Dermatol., 2003 February, 120 (2): 246–255 and S. B. Joseph, et al. Nat. Med., 2003 February, 9 (2): 213–219) and a method for preventing or treating neurodegenerative diseases or neurological disorders, particularly neurodegenerative diseases or disorders characterized by neuron degeneration, neuron injury or impaired plasticity or inflammation in the CNS (as disclosed in U.S. Provisional Patent Application No. 60/368,424, filed 27 Mar., 2002). Particular diseases or conditions that are characterized by neuron degeneration and inflammation, and thus benefiting from the growth and/or repair of neurons include stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis. Diseases or conditions that are characterized by neuron degeneration and/or impaired plasticity include psychiatric disorders such as schizophrenia and depression. Particular diseases or conditions that, are characterized by neuronal injury include those conditions associated with brain and/or spinal cord injury, including trauma.

The methods of the present invention are useful for the treatment of animals including mammals generally and particularly humans. The present invention further provides the use of compounds of this invention for the preparation of a medicament for increasing reverse cholesterol transport.

The methods of the present invention comprise the step of administering a therapeutically effective amount of the compound of this invention. As used herein, the term "therapeutically effective amount" refers to an amount of the compound of this invention that is sufficient to achieve the stated effect. Accordingly, a therapeutically effective amount of a compound of this invention used in the method for the prevention or treatment of LXR mediated diseases or conditions will be an amount sufficient to prevent or treat the LXR mediated disease or condition. Similarly, a therapeutically effective amount of a compound of this invention for use in the method of increasing reverse cholesterol transport will be an amount sufficient to increase reverse cholesterol transport.

The amount of a compound of this invention or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of LXR mediated diseases and conditions in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including increasing reverse cholesterol transport, and inhibiting cholesterol absorption.

In another embodiment, the present invention provides pharmaceutical compositions comprising a compound of this invention or a pharmaceutically acceptable salt or solvate thereof, as the active ingredient, and at least one pharmaceutical carrier or diluent These pharmaceutical compositions may be used in the prophylaxis and treatment of the foregoing diseases or conditions and in cardiovascular therapies as mentioned above. The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of LXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

Suitable formulations for administration by inhalation include fine particle dusts or mists which may be generated by means of various types of metered dose pressurized aerosols, nebulisers, or insufflators.

For pulmonary administration via the mouth, the particle size of the powder or droplets is typically in the range 0.5–10 µM, preferably 1–5 µM, to ensure delivery into the bronchial tree. For nasal administration, a particle size in the range 10–500 µM is preferred to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 µL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

General Methods

In one embodiment of this invention, the method for the preparation of compounds of Formulas I, II, I-A and II-A comprises the steps of:

(a) reacting an alcohol having the formula: $HY'—(CR^4R^5)_n$-L, where $Y'$ is —O—, —S—, —NH or protected —NH and L is a leaving group, such as a halogen (iodide, bromide or chloride), sulfonate (tosylate, mesylate, triflate, etc.) or is a group that is converted to a leaving group (e.g., an alcohol), with an alcohol having the formula:

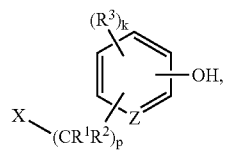

where X is a protected carboxylic acid moiety, to form a compound having the formula:

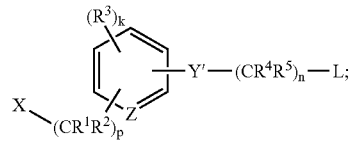

(b) reacting the compound formed in step (a) with a secondary amine having the formula

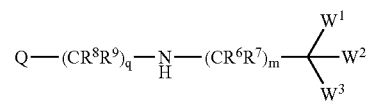

to form a compound having the formula:

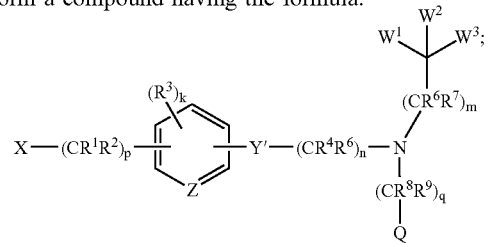

(c) converting the protected carboxylic acid moiety into a desired amide moiety; and (d) optionally oxidizing the compound formed in step (b) to the N-oxide thereof.

In another embodiment of this invention, the method for the preparation of compounds of Formulas I, II, I-A and II-A comprises the steps of (a) reacting an acetylene having the formula: $R'O—(CR^4R^5)_{n-1}—C≡C—H$, where $R'$ is a hydroxyl protecting group, with a halogen-containing aromatic compound having the formula

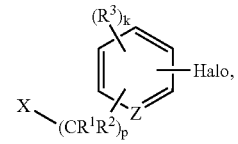

where X is a protected carboxylic acid moiety and Halo is bromo or iodo, in the presence of a catalyst to form a compound having the formula:

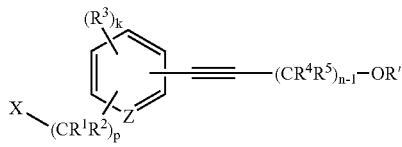

(b) reducing the compound formed in step (a) and converting the protected hydroxyl group into a leaving group, L, such as a halogen (iodide, bromide or chloride), sulfonate (tosylate, mesylate, triflate, etc.) or is a group that is converted to a leaving group (e.g., an alcohol), to form a compound having the formula:

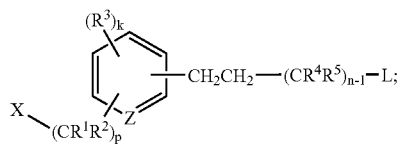

(c) reacting the compound formed in step (b) with an amine having the formula:

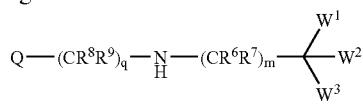

to form a compound having the formula:

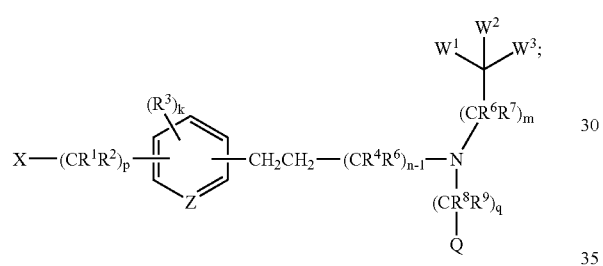

(d) converting the protected carboxylic acid moiety into a desired amide moiety; and (e) optionally oxidizing the compound formed in step (b) to the N-oxide thereof.

Specific Methods

Compounds of Formulas I, II, I-A and II-A were prepared by methods analogous to those described in Schemes 1–3.

Scheme 1

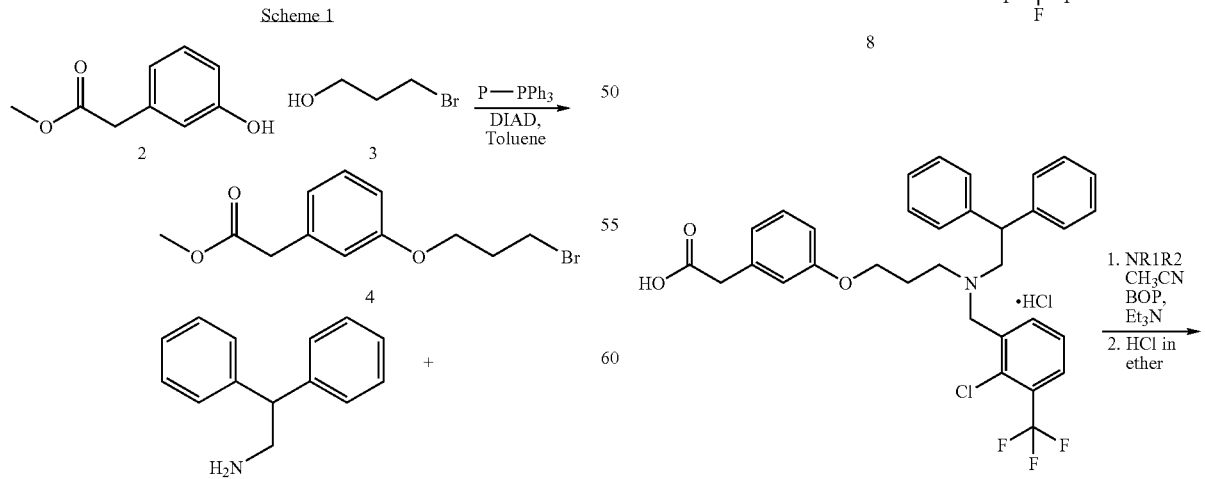

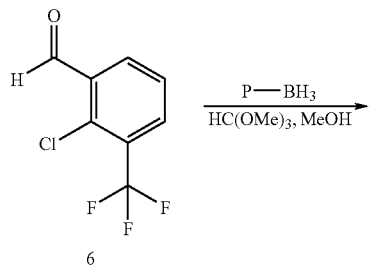

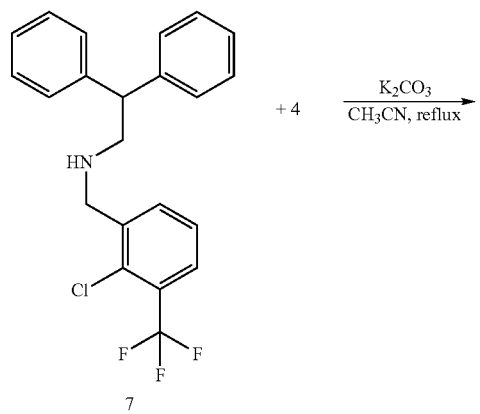

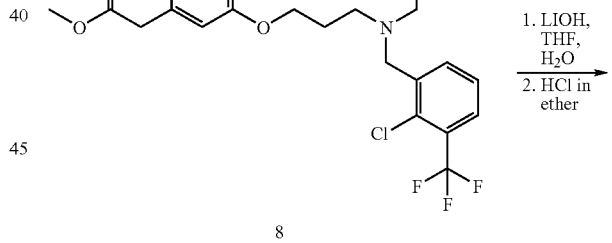

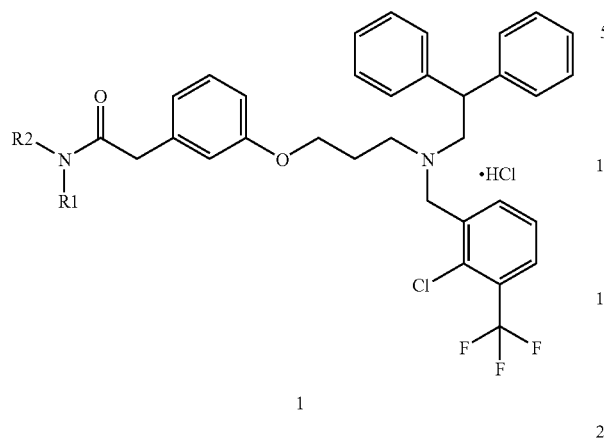

A phenol (2) was coupled to an alcohol (3) in the presence of polymer bound triphenylphosphine and diisopropyl azodicarboxylate (DIAD) to give an aryl ether (4). A secondary amine (7) was prepared by reductive amination of a primary amine (5) with an aldehyde (6) in the presence of a reducing agent, such as polymer-bound borohydride. The secondary amine (7) then displaced the bromine from compound (4) to form a tertiary amine (8). The ester of compound (8) was then hydrolyzed to the acid (9) under basic conditions. Acid compound (9) may optionally be converted to a salt, such as a hydrochloride salt. The acid (9) was treated with an amine and BOP reagent (benzotriazol-1-yloxytris(dimethylamino)phosphonium hexafluorophosphate) to form the amide product. The amide may be optionally converted to a salt (1), such as a hydrochloride salt, using conventional procedures.

Scheme 2

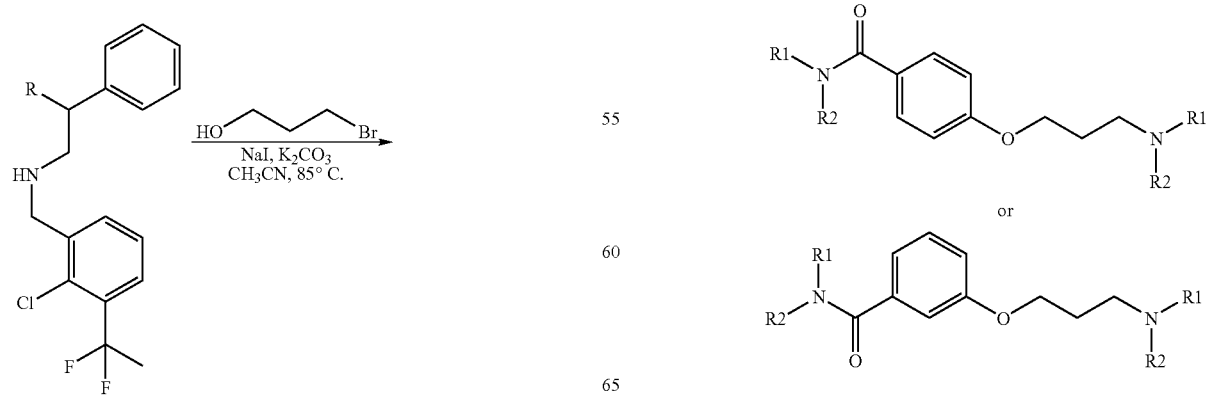

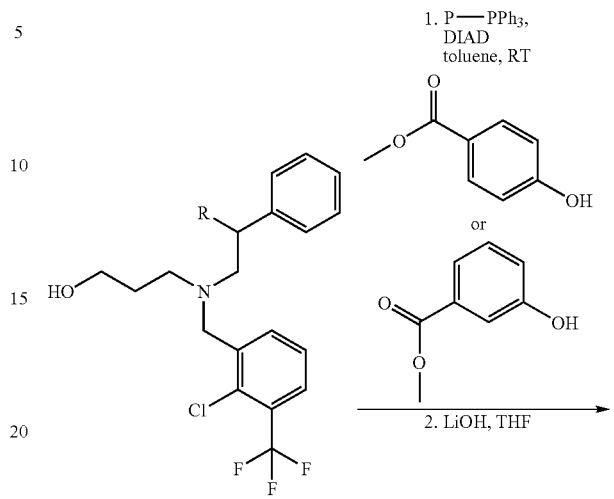

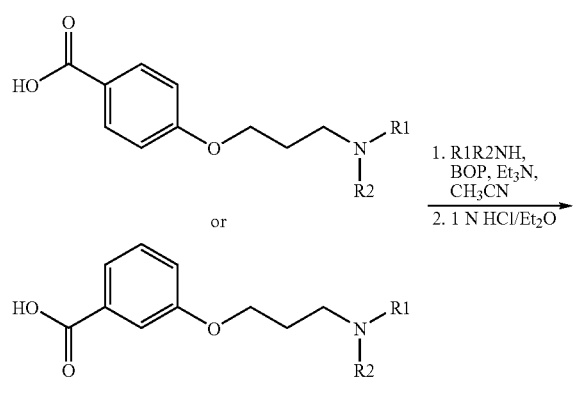

Scheme 3

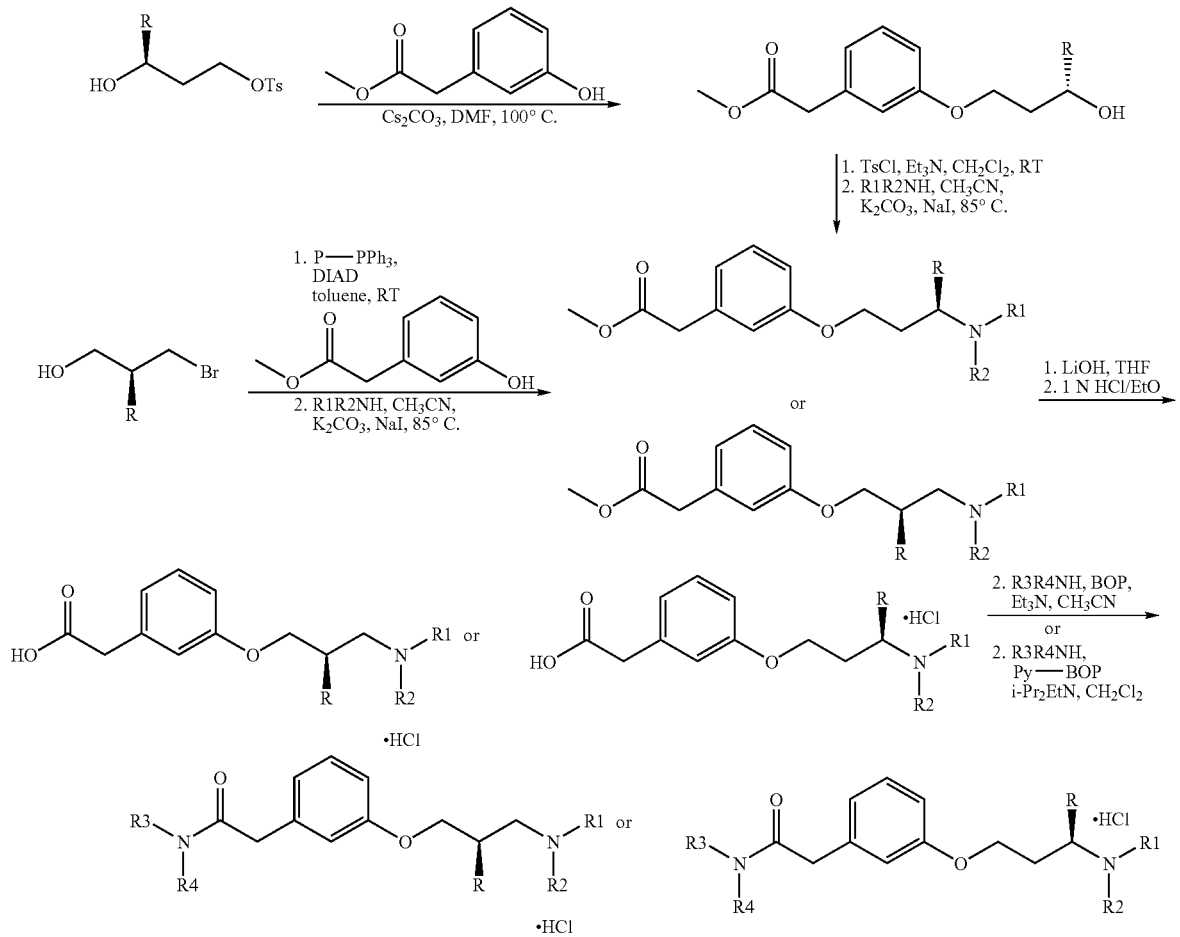

Each of the above-described methods further include the optional step(s) of forming a pharmaceutically acceptable salt of a compound of this invention, and/or of forming a pharmaceutically acceptable solvate of a compound of this invention or a pharmaceutically acceptable salt thereof.

The following Test Methods and Examples are intended for illustration only and are not intended to limit the scope of the invention in any way; the present invention being defined by the claims.

In the Test Methods and Examples, the following terms have the designated meaning: "pRSETa" is a known expression vector available from Invitrogen; "IPTG" means isopropyl β-D-thiogalactopyranoside; "PO$_4$" means phosphate; "PBS" means phosphate buffered saline; "TBS" means tris-buffered saline; EDTA means ethylenediamine tetraacetic acid; "DTT" means dithiothreitol; "FAF-BSA" means fatty-acid free bovine serum albumin; "SRC-1" means steroid receptor coactivator 1; "CS" means charcoal stripped; "nM" means nanomolar; "µM" means micromolar; "mM" means millimolar; "mmol" means millimoles; "g" means grams; "ng" means nanograms; "mg/ml" means milligram per milliliter; "µL" means microliters; and "mL" means milliliter.

Test Method 1: Ligand Sensing Assay (LiSA) for LXRβ Agonist Activity

This assay measures the recruitment of a peptide derived from the coactivator protein, SRC1, to the agonist-bound LXR□. Peptides derived from other nuclear receptor cofactors may be similarly prepared and assayed.

To generate the human LXRβ ligand binding domain suitable for LiSA, a modified polyhistidine tag (MKKGH-HHHHHG) (SEQ ID No. 1) was fused in frame to the human LXRβ ligand binding domain (amino acids 185–461 of Genbank accession number U07132) and subcloned into the expression vector pRSETa (Invitrogen) under the control of an IPTG inducible T7 promoter. The human LXRβ ligand binding domain was expressed in *E. coli* strain BL21(DE3). Ten-liter fermentation batches were grown in Rich PO$_4$ media with 0.1 mg/mL Ampicillin at 25° C. for 12 hours, cooled to 9° C. and held at that temperature for 36 hours to a density of OD600=14. At this cell density, 0.25 mM IPTG was added and induction proceeded for 24 hours at 9° C., to a final OD600=16. Cells were harvested by centrifugation (20 minutes, 3500 g, 4° C.), and concentrated cell slurries were stored in PBS at −80° C.

Typically 25–50 g of cell paste is resuspended in 250–500 mL TBS, pH 8.0 (25 mM Tris, 150 mM NaCl). Cells are lysed by passing 3 times through an APV Rannie MINI-lab homogenizer and cell debris is removed by centrifugation (30 minutes, 20,000 g, 4° C.). The cleared supernatant is filtered through coarse pre-filters, and TBS, pH 8.0, containing 500 mM imidazole is added to obtain a final imidazole concentration of 50 mM. This lysate is loaded onto a column (XK-26, 10 cm) packed with Sepharose [Ni++ charged] Chelation resin (available from Pharmacia) and pre-equilibrated with TBS pH 8.0/50 mM imidazole. After washing to baseline absorbance with equilibration buffer, the column is washed with approximately one column volume of TBS pH −8.0 containing 95 mM imidazole. LXRβLBD (185–461) is eluted with a gradient from 50 to 500 mM imidazole. Column peak fractions are pooled immediately and diluted 5 fold with 25 mM Tris pH 8.0, containing 5% 1,2-propanediol, 0.5 mM EDTA and 5 mM DTT. The diluted protein sample is then loaded onto a column (XK-16, 10 cm) packed with Poros HQ resin (anion exchange). After washing to baseline absorbance with the dilution buffer the protein is eluted with a gradient from 50–500 mM NaCl. Peak fractions are pooled and concentrated using Centriprep 10K (Amicon) filter devices and subjected to size exclusion, using a column (XK-26, 90 cm) packed with Superdex-75 resin (Pharmacia) pre-equilibrated with TBS, pH 8.0, containing 5% 1,2-propanediol, 0.5 mM EDTA and 5 mM DTT.

LXRβ protein was diluted to approximately 10 μM in PBS and fivefold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000× molar excess of Tris-HCl, pH 8. The modified LXRβ protein was dialyzed against 4 buffer changes, each of at least 50 volumes, PBS containing 5 mM DTT, 2 mM EDTA and 2% sucrose. The biotinylated LXRβ protein was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

The biotinylated protein was incubated for 20–25 minutes at a concentration of 5 nM in assay buffer (50 mM NaF, 50 mM MOPS-pH 7.5, 0.1 mg/ml FAF-BSA, 0.05 mM CHAPS, 10 mM DTT) with equimolar amounts of streptavidin-AlloPhycoCyanin (APC, Molecular Probes). At the same time, the biotinylated peptide comprising amino acids 676–700 of SRC-1 (CPSSHSSLTERHKILHRLLQEGSPS-CONH2) (SEQ ID No. 2) at a concentration of 10 nM was incubated in assay buffer with a ½ molar amount of streptavidin-labelled Europium (Wallac) for 20–25 minutes. After the initial incubations are completed, a 20 molar excess of biotin was added to each of the solutions to block the unattached streptavidin reagents. After 20 min at room temp, the solutions were mixed yielding a concentration of 5 nM for the dye-labeled LXR protein and 10 nM for SRC-1 peptide.

49 uL of the protein/peptide mixture was added to each well of an assay plate containing 1 ul of test compound serial diluted in 100% DMSO. The final volume in each well was 0.05 mL, and the concentration in the well for the dye-labeled protein and peptide was 5 nM protein and 10 nM SRC1-peptide. The final test compound concentrations between 33 pM and 20 uM. The plates were incubated at room temp 2-hours and then counted on a Wallac Victor V fluorescent plate reader.

In this assay 1 μM 24(S), 25-epoxycholesterol gave a reading of 20000 fluorescence units over a background reading of 10000 fluorescence units.

Test Method 2: Ligand Sensing Assay for LXRα Agonist Activity

The assay for LXRα was run according to the procedures of Test Method 1, above using his-tagged LXRα ligand binding domain (amino acids 183–447 of Genbank accession number U22662, with the 14$^{th}$ amino acid corrected to A from R). In this assay 1 μM 24(S),25-epoxycholesterol gave a reading of 20000 fluorescence units over a background reading of 10000 fluorescence units.

EXAMPLE 1

2-(3-{3-[(2-Chloro-3-(trifluoromethyl)-benzyl)-(2, 2diphenylethyl)-amino]-propoxy}phenyl)-1-morpholin-4-yl-ethanone hydrochloride salt

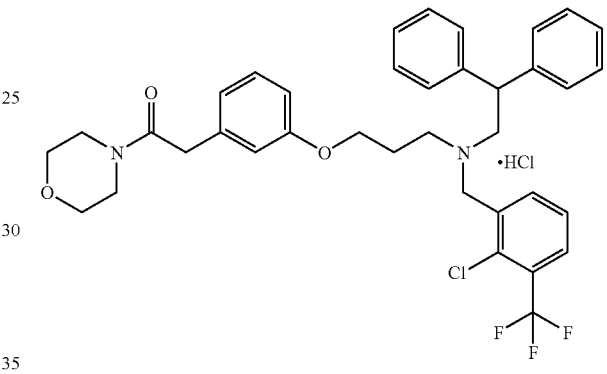

a) Methyl [3-(3-bromopropoxy)phenyl]acetate

A solution of methyl 3-hydroxyphenylacetate (11.3 g, 0.068 mole) in 300 mL of anhydrous toluene was treated with 3-bromopropanol (12.2 g, 0.088 mole). Polymer bound triphenylphosphine (36.0 g, 0.108 mole, 3 mmol/g, Fluka Chemie) was then added, and the mixture reacted for 15 minutes. The reaction mixture was then cooled to 0° C. and diisopropylazodicarboxylate (16.9 g, 0.084 mol) was added in a dropwise fashion. After stirring at room temperature overnight, the crude reaction mixture was filtered and the solid washed with 100 mL toluene. After concentration of the filtrate in vacuo, the crude product was purified by column chromatography over silica gel (silica gel 60, EM Science) using 15% EtOAc:hexane as eluent to afford 15.8 g (81% yield) of the title compound as an oil: $^1$H NMR (CDCl$_3$, 400 MHz) δ 7.23–7.19 (m, 1 H), 6.85–6.7 (m, 3), 4.09–4.06 (t, 2 H, J=5.8), 3.67 (s, 3 H), 3.67–3.56 (m, 4 H), 2.32–2.26 (p, 2 H, J=6.0); MS (ESP+) m/e 288 (MH$^+$); TLC (hexanes:EtOAc/3:1) R$_f$=0.68. Anal. (C$_{12}$H$_{15}$O$_3$Br) C, H, N.

b) N-[2-Chloro-3-(trifluoromethyl)benzyl]-N-(2,2-diphenylethyl)amine

A solution of 2,2-diphenethylamine (10.0 g, 50.7 mmol) and 2-chloro-3-trifluoromethylbenzaldehyde (10.5 g, 50.7 mmol) in 80 mL of methanol and 40 mL of trimethylorthoformate was stirred at room temperature for 15 hours whereupon polymer-supported borohydride resin (20.3 g, 55.8 mmol, 2.5 mmol/g, Aldrich) was added in one portion.

After stirring at room temperature for 24 h, the reaction was filtered and the filtrate was concentrated in vacuo. The crude product was purified by column chromatography over silica gel (silica gel 60, EM Science) using EtOAc:hexane/40:60 with 1% NH$_4$OH as the eluent to give 11.2 g (57% yield) of the title compound as an oil: $^1$H NMR (CDCl$_3$, 400 MHz) δ 7.57 (d, 1 H, J=8.0), 7.52 (d, 1 H, J=7.6), 7.32–7.15 (m, 11 H), 4.20 (t, 1 H, J=7.6), 3.94 (s, 2 H), 3.22 (d, 2 H, J=7.6); HPLC (Waters symmetry shield, RPq 3.5 micron, 2.1×30 mm, 85:15/H$_2$O:CH$_3$CN with 0.1% HCOOH to 100% CH$_3$CN after 4 min, flow rate=0.8 mL/min) t$_R$=2.39 min; MS (ESP+) m/e 390 (MH$^+$); TLC (hexanes:EtOAc/4:1) R$_f$=0.42.

c) Methyl (3-{3-[[2-Chloro-3-(trifluoromethyl)benzyl](2,2-diphenylethyl)amino]propoxy}phenyl)acetate A solution of methyl [3-(3-bromopropoxy)phenyl]acetate (1.0 g, 3.48 mmole) and N-[2chloro-3-(trifluoromethyl) benzyl]-2,2-diphenylethanamine (1.63 g, 4.18 mmole) in 20 mL of acetonitrile was treated with potassium carbonate (0.72 g, 5.2 mmol). The reaction mixture was heated to reflux and stirred for 4 days. The reaction mixture was filtered, and the filtrate was concentrated in vacuo. The crude product was purified by flash chromatography (silica gel cartridge, Biotage 32–63 um, 60A) with 10% EtOAc:hexanes as the eluent to afford 1.69 g (81% yield) of the title compound as a viscous oil: $^1$H NMR (CDCl$_3$, 400 MHz) δ 7.46–7.44 (d, 1 H, J=7.7), 7.25–7.14 (m, 12 H), 6.91–6.84 (m, 2 H), 6.66–6.62 (m, 2 H), 4.154.09 (t, 1 H, J=7.6), 3.78 (s, 1 H), 3.69–3.66 (m, 5 H), 3.59(S, 2 H), 3.15–3.13 (d, 2 H, J=7.7), 2.72–2.68 (t, 2 H, J=6.6), 1.87–1.80 (m, 2 H); MS (ESP+) m/e 597 (MH$^+$); TLC (hexanes:EtOAc/9:1) R$_f$=0.36.

d) 2-(3-{3-[[2-Chloro-3-(trifluoromethyl)benzyl](2,2-diphenylethyl)amino]propoxy}-phenyl)acetic acid hydrochloride salt A solution of methyl (3-{3-[[2-chloro-3-(trifluoromethyl) benzyl](2,2-diphenylethyl)amino]propoxy}phenyl)acetate (113 mg, 0.19 mmol) in 1.5 mL of tetrahydrofuran and 1 mL of water was treated with 1N aqueous LiOH (0.29 mL, 0.29 mmol). After stirring at room temperature for 2 hours, additional 1N aqueous LiOH (0.29 mL, 0.29 mmol) was added and stirring was continued for 2 hours. The reaction was neutralized with AcOH (66 µL, 0.58 mmol) and poured into H$_2$O/EtOAc. The layers were separated and the aqueous layer was extracted with EtOAc (3×). The combined organic layers were washed with brine (1×), dried over magnesium sulfate, filtered, and concentrated in vacuo. The crude material was purified by preparative thin layer chromatography (silica gel, 1 mm plates, Merck 20×20 cm silica gel 60 F$_{254}$) eluting with CH$_2$Cl$_2$:MeOH (95:5) to afford an oil. The oil was dissolved in Et$_2$O and acidified with excess HCl/Et$_2$O. The reaction was concentrated in vacuo and dried under reduced pressure to give 65 mg (56% yield) of the title compound as a white solid: H NMR (C$_5$D$_5$N, 400 MHz) δ 7.60–7.05 (m, 15 H), 7.01 (t, 1 H, J=7.6), 6.84 (dd, 1 H, J=8.4, 2.4), 4.32 (t, 1 H, J=7.6), 3.89 (s, 2 H), 3.77 (s, 2 H), 3.71 (t, 2 H, J=5.6), 3.16 (d, 2 H, J=7.6), 2.65 (t, 2 H, J=6.4), 1.88–1.78 (m, 2 H).

e) 2-(3-{3-[(2-Chloro-3-(trifluoromethyl)-benzyl)-(2,2-diphenylethyl)-amino]-propoxy}phenyl)-1-morpholinyl-ethanone hydrochloride salt 2-(3-{3-[[2-chloro-3-(trifluoromethyl)benzyl)(2,2-diphenylethyl)-amino]-propoxy}-phenyl acetic acid (50 mg, 0.086 mmole) and morpholine (8.7 mg, 0.10 mmole) were dissolved in CH3CN (2 ml). BOP reagent (44 mg, 0.10 mmole) was added followed by Et3N (20 mg, 0.20 mmole). The resultant mixture was stirred at room temperature for 2 h. The mixture was concentrated under reduced pressure. The residue was partitioned between EtOAc and aqueous Na$_2$CO$_3$ (5%) solution. The organic layer was separated, dried over MgSO$_4$ and concentrated. In cases where the product required further purification, a preparative Gilson HPLC was used (YMC CombiPrep ODS-A, 50×20 mm, 20 ml/min, 30–90% CH3CN over 15 minutes). The HCl salt was made by adding HCl (in ether) to an ether solution of the product and then evaporation of the solvent to give a yellow solid (32 mg, 54%). MS(ES) m/e 651.2 [M+H]$^+$.

EXAMPLE 2

2-3-{3-[(2-Chloro-3-(trifluoromethyl)-benzyl)-(2,2-diphenylethyl)-amino]-propoxy}phenyl)-N-methyl-acetamide hydrochloride salt

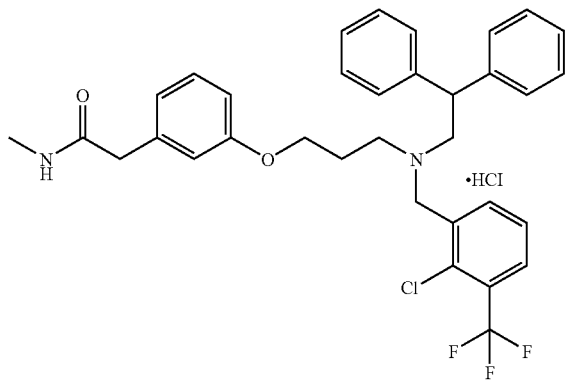

Following the procedure of Example 1 except substituting methylamine for morpholine in step e, the title compound was obtained as a yellow solid (36 mg, 66%). MS(ES) m/e 595.2 [M+H]$^+$.

EXAMPLE 3

2-(3-{3-[(2-Chloro-3-(trifluoromethyl)-benzyl)(2,2-diphenylethyl)-amino]-propoxy}phenyl)-N,N-dimethyl-acetamide hydrochloride salt

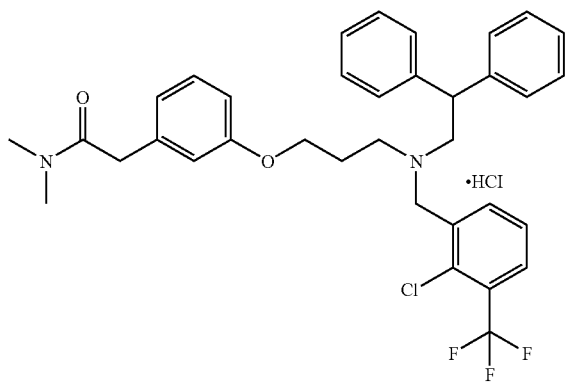

Following the procedure of Example 1 except substituting dimethylamine for morpholine in step e, the title compound was obtained as a yellow solid (36 mg, 65%). MS(ES) m/e 609.4 [M+H]+.

EXAMPLE 4

2-(3-{3-[(2-Chloro-3-(trifluoromethyl)-benzyl)-(2,2-diphenylethyl)-amino]-propoxy}phenyl)-1-piperidyn-1-yl-ethanone hydrochloride salt

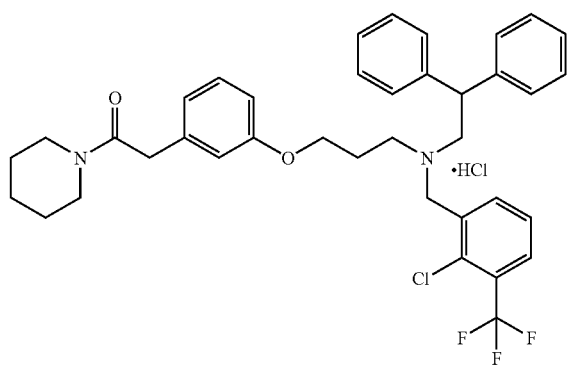

Following the procedure of Example 1 except substituting piperidine for morpholine in step e, the title compound was obtained as a yellow solid (50 mg, 85%). MS(ES) m/e 649.4 [M+H]+.

EXAMPLE 5

2-(3-{3-[(2-Chloro-3-(trifluoromethyl)-benzyl)-(2,2-diphenylethyl)-amino]-propoxy}phenyl)-1-(4-methyl-piperazin-1-yl)-ethanone hydrochloride salt

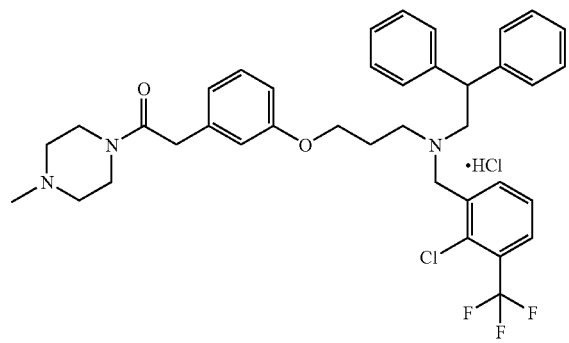

Following the procedure of Example 1 except substituting 4-methyl-piperazine for morpholine in step e, the title compound was obtained as a yellow solid (60 mg, quantitative yield). MS(ES) m/e 664.2 [M+H]+.

EXAMPLE 6

2-(3-{3-[(2Chloro-3-(trifluoromethyl)-benzyl)-(2,2-diphenylethyl)-amino]-propoxy}phenyl)-1-pyrrolidin-1-yl-ethanone hydrochloride salt

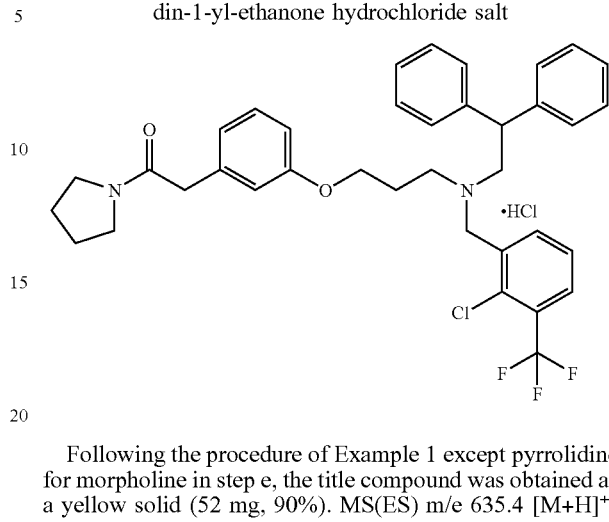

Following the procedure of Example 1 except pyrrolidine for morpholine in step e, the title compound was obtained as a yellow solid (52 mg, 90%). MS(ES) m/e 635.4 [M+H]+.

EXAMPLE 7

2-(3-{3-[(2-Chloro-3-(trifluoromethyl)-benzyl)-(2,2-diphenylethyl)amino]-propoxy}phenyl)-N-ethyl-acetamide hydrochloride salt

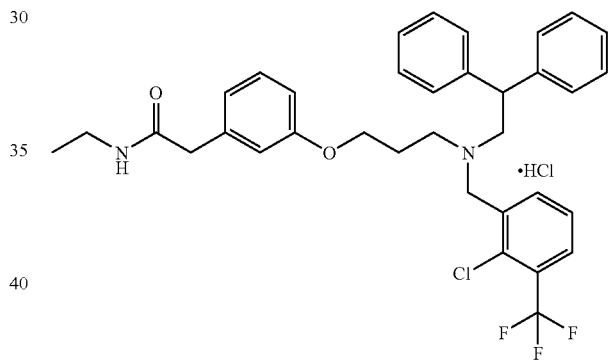

Following the procedure of Example 1 except ethylamine for morpholine in step e, the title compound was obtained as a yellow solid (40 mg, 72%). MS(ES) m/e 609.2 [M+H]+.

EXAMPLE 8

2-(3-{3-[(2-Chloro-3-(trifluoromethyl)-benzyl)-2,2-diphenylethyl)-amino]-propoxy}phenyl)-N,N-diethyl-acetamide hydrochloride salt

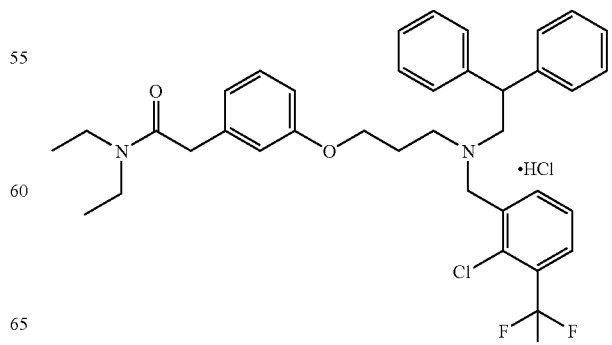

Following the procedure of Example 1 except diethylamine for morpholine in step e, the title compound was obtained as a yellow solid (50 mg, 86%). MS(ES) m/e 637.2 [M+H]+.

EXAMPLE 9

2-3-{3-[(2-Chloro-3-(trifluoromethyl)-benzyl)-(2,2-diphenylethyl)-amino]-propoxy}phenyl)-1-azetidin-1-yl-ethanone hydrochloride sat

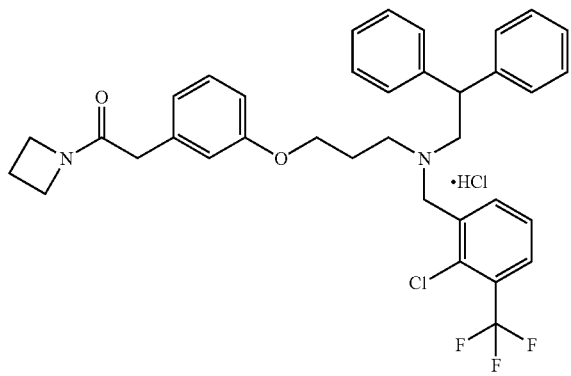

Following the procedure of Example 1 except azetidine for morpholine in step e, the title compound was obtained as a yellow solid (57 mg, quantitative yield). MS(ES) m/e 621.2 [M+H]+.

EXAMPLE 10

2-3-{3-[(2-Chloro-3-(trifluoromethyl)-benzyl)-(2,2-diphenylethyl)-amino]-propoxy}phenyl)-1-azepan-1-yl-ethanone hydrochloride salt

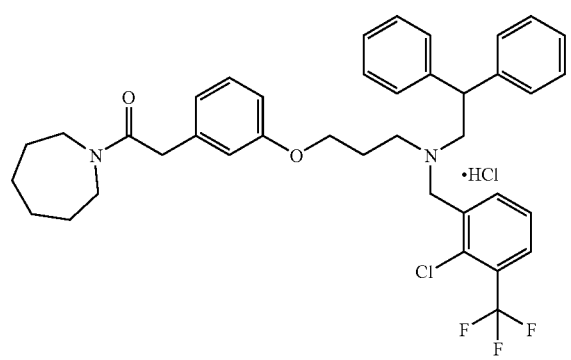

Following the procedure of Example 1 except azepane for morpholine in step e, the title compound was obtained as a yellow solid (60 mg, quantitative yield). MS(ES) m/e 663.2 [M+H]+.

EXAMPLE 11

(S)-2-(3-{3-[[2Chloro-3-(trifluoromethyl)benzyl](2-phenyl-propyl)amino]propoxy}-phenyl)-acetamide

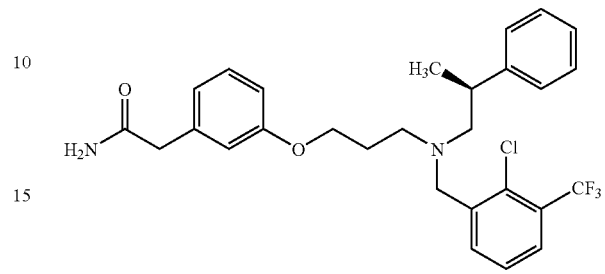

a) (S)-(2-Chloro-3-trifluoromethyl-benzyl)-(2-phenyl-propyl)-amine

To a solution of (S)-2-phenyl propylamine (0.5 g, 3.7 mmol) in dry dichloromethane was added acetic acid followed by 2-chloro-3-trifluoromethylbenzaldehyde (1.1 g, 5.5mmol) and sodium triacetoxyborohydride (1.5 g, 7.4 mmol). After the resulting mixture was stirred for 1.5 h at RT water was added to quench the reaction. The aqueous layer was extracted with ethyl acetate. The combined organic layers were washed with brine, dried over sodium sulfate, and concentrated in vacuo. The crude mixture was purified by column chromatograph (Ethyl acetate:Hexane/25:75) to give the title compound as an oil (0.55 g, 45%). MS (ESI) 327.6 (M+H)+.

b) (S)-(3-{3-[[2-Chloro3-(trifluoromethyl)benzyl](2-phenyl-propyl)amino]propoxy}-phenyl)acetic acid methyl ester A solution of (3-{3-bromo-propoxyl}-phenyl)acetic acid methyl ester (0.55 g, 1.5 mmol) and (S)-(2-Chloro-3-trifluoromethyl-benzyl)-(2-phenyl-propyl)-amine (0.55 g, 1.6 mmol) in acetonitrile (10 ml) was treated with solid potassium carbonate(0.4 g, 2.4 mmol).The reaction was heated to reflux and stirred for 48 h. Upon cooling to RT, the reaction was filtered through a pad of celite, washed with ethyl acetate, and the filtrate was concentrated in vacuo. The crude product was purified by column chromatograph (Ethyl acetate:Hexane/20:80) to give the title compound as an oil (0.6 g, 67%). MS (ESI) 534.6 (M+H)+.

c) (S)-2-3-{3-[[2-Chloro-3-(trifluoromethyl)benzyl](2-phenyl-propyl)amino]propoxy}-phenyl)acetic acid A solution of (S)-(3-{3-[[2-chloro-3-(trifluoromethyl)benzyl](2-phenyl-propyl)amino]propoxy}phenyl)acetic acid methyl ester (0.6 g, 1.1 mmol) in THF (9 ml) and water (6 ml) was treated with aqueous LiOH (1.0 N, 1.0 ml, 1.0 mmol). After stirring at RT for 2 h, additional LiOH (1.0 ml, 1.0 mmol) was added and stirring was continued for 2 h. The reaction was neutralized with acetic acid and poured into water and ethyl acetate. The layers were separated and the aqueous layer was extracted with ethyl acetate. The combined organic layers were washed with brine, dried over sodium sulfate and concentrated in vacuo. The crude mixture was purified by HPLC to give the title compound as an oil (0.4 g, 75%). MS (ESI) 520.2 (M+H)⁺.

d) (S)-2-(3-{3-[(2-Chloro-3-(trifluoromethyl)benzyl](2-phenyl-propyl)amino]propoxy}-phenyl)acetic acid hydrochloride salt To a solution of the (S)-2-(3-{3-[[2-chloro-3-(trifluoromethyl)benzyl](2-phenyl-propyl)amino]propoxy}-phenyl) acetic acid in ethyl ether was added HCl in diethyl ether (1.0M).The suspension was filtered and dried to give the title compound as a white solid (99%). NMR(400 MHz, CD₃OD) δ: 8.0 (d, J=4.0Hz, 1H), 7.9 (d, J=4.0Hz, 1H), 7.7–7.3 (m, 7H), 7.1 (d, J=8.0 Hz, 1H), 6.8 (m, 2H), 4.1–3.4 (m, 11H), 2.3 (m, 2H), 1.5 (d, J=4.0 Hz, 3H).

e)-2-(3-{3-[[2-Chloro-3-trifluoromethyl)benzyl](2-phenyl-propyl)amino]propoxy}-phenyl)-acetamide To a solution (S)-2-(3-{3-[[2-chloro-3-(trifluoromethyl)benzyl](2-phenyl-propyl)amino]propoxy}-phenyl)acetic acid hydrochloride salt (50 mg, 0.1 mmol) in dichloromethane, 1,2-dichloroethane (EDC, 19.2 mg, 0.1 mmol), 1-hydroxybenzotriazole hydrate (HOBT, 13.6 mg, 0.1 mmol), triethylamine (Et3N, 14 μl, 0.1 mmol) and ammonia (1.0M in dioxane, 0.24 ml) were added. After the resulting mixture was stirred at room temperature for over night it was washed with 0.1N HCl, saturated NaHCO₃, water and brine. The organic layer was dried over Na₂SO₄ and concentrated under vacuum. The residue was purified with HPLC to give the tittle compound as a light yellow oil 30 mg, yield 60%. MS m/e 519.0 (M+H)⁺.

The following compounds 12–41 were prepared using the below-listed amine in the experimental procedures described herein:

| Ex. | Amine | Compound Name | M/S |
|---|---|---|---|
| 12 | (1H-Imidazol-2-yl)-methylamine | 2-(3-{3-[(2-Chloro-3-trifluoromethyl-benzyl)-diphenylethyl-amino]-propoxy}-phenyl)-N-(1H-imidazol-2-ylmethyl)-acetamide hydrochloride salt | 661.4 (M⁺) |
| 13 | (5-Bromo-thiophen-2-yl)-methylamine | N-(5-Bromo-thiophen-2-ylmethyl)-2-(3-{3-[(2-Chloro-3-trifluoromethyl-benzyl)-diphenylethyl-amino]-propoxy}-phenyl)-acetamide hydrochloride salt | 755.2 (M − H)⁺ |
| 14 | Thiophen-2-yl-methylamine | 2-(3-{3-[(2-Chloro-3-trifluoromethyl-benzyl)-diphenylethyl-amino]-propoxy}-phenyl)-N-thiophen-2-ylmethyl-acetamide hydrochloride salt | 677.2 (M⁺) |
| 15 | 2-Methoxy-ethylamine | 2-(3-{3-[(2-Chloro-3-trifluoromethyl-benzyl)-diphenylethyl-amino]-propoxy}-phenyl)-N-(2-methoxy-ethyl)-acetamide hydrochloride salt | 639.4 (M⁺) |
| 16 | N¹,N¹-Dimethyl-ethane-1,2-diamine | 2-(3-{3-[(2-Chloro-3-trifluoromethyl-benzyl)-diphenylethyl-amino]-propoxy}-pheny)-N-(2-dimethylamino-ethyl)-acetamide hydrochloride salt | 652.2 (M⁺) |
| 17 | 2-Morpholin-4-yl-ethylamine | 2-(3-{3-[(2-Chloro-3-trifluoromethyl-benzyl)-diphenylethyl-amino]-propoxy}-phenyl)-N-(2-morpholin-4-yl-ethyl)-acetamide hydrochloride salt | 694.2 (M⁺) |
| 18 | 2-Methoxy-1-methyl-ethylamine | 2-(3-{3-[(2-Chloro-3-trifluoromethyl-benzyl)-diphenylethyl-amino]-propoxy}-phenyl)-N-(2-methoxy-1-methyl-ethyl)-acetamide hydrochloride salt | 653.2 (M⁺) |
| 19 | (2-Methoxy-ethyl)-methylamine | 2-(3-{3-[(2-Chloro-3-trifluoromethyl-benzyl)-diphenylethyl-amino]-propoxy}-phenyl)-N-(2-methoxy-ethyl)-N-methyl-acetamide hydrochloride salt | 653.4 (M⁺) |
| 20 | Bis-(2-methoxy-ethyl)-amine | 2-(3-{3-[(2-Chloro-3-trifluoromethyl-benzyl)-diphenylethyl-amino]-propoxy}-phenyl)-N,N-bis-(2-methoxy-ethyl)-acetamide hydrochloride salt | 697.2 (M⁺) |
| 21 | Furan-2-yl-methylamine | 2-(3-{3-[(2-Chloro-3-trifluoromethyl-benzyl)-diphenylethyl-amino]-propoxy}-phenyl)-N-furan-2-ylmethyl-acetamide hydrochloride salt | 661.4 (M⁺) |
| 22 | (3-Methyl-isoxazol-5-yl)-methylamine | 2-(3-{3-[(2-Chloro-3-trifluoromethyl-benzyl)-diphenylethyl-amino]-propoxy}-phenyl)-N-(3-methyl-isoxazol-5-ylmethyl)-acetamide hydrochloride salt | 676.2 (M⁺) |
| 23 | 2-Thiomorpholin-4-yl-ethylamine | 2-(3-{3-[(2-Chloro-3-trifluoromethyl-benzyl)-diphenylethyl-amino]-propoxy}-phenyl)-N-(2-thiomorpholin-4-yl-ethyl)-acetamide hydrochloride salt | 710.2 (M⁺) |
| 24 | 2-Pyrrolidin-1-yl-ethylamine | 2-(3-{3-[(2-Chloro-3-trifluoromethyl-benzyl)-diphenylethyl-amino]-propoxy}-phenyl)-N-(2-pyrrolidin-1-yl-ethyl)-acetamide hydrochloride salt | 678.2 (M⁺) |
| 25 | Pyridin-3-yl-methylamine | 2-(3-{3-[(2-Chloro-3-trifluoromethyl-benzyl)-diphenylethyl-amino]-propoxy}-phenyl)-N-pyridin-3-ylmethyl-acetamide hydrochloride salt | 672.2 (M⁺) |
| 26 | 2-Pyridin-2-yl-ethylamine | 2-(3-{3-[(2-Chloro-3-trifluoromethyl-benzyl)-diphenylethyl-amino]-propoxy}-phenyl)-N-(2-pyridin-2-yl-ethyl)-acetamide hydrochloride salt | 686.2 (M⁺) |
| 27 | 2-Phenoxy-ethylamine | 2-(3-{3-[(2-Chloro-3-trifluoromethyl-benzyl)-diphenylethyl-amino]-propoxy}-phenyl)-N-(3-phenoxy-ethyl)-acetamide hydrochloride salt | 701.4 (M⁺) |

-continued

| Ex. | Amine | Compound Name | M/S |
|---|---|---|---|
| 28 | 3-Isopropoxy-propylamine | 2-(3-{3-[(2-Chloro-3-trifluoromethyl-benzyl)-diphenylethyl-amino]-propoxy}-phenyl)-N-(3-isopropoxy-propyl)-acetamide hydrochloride salt | 667.4 $(M - CH_3)^+$ |
| 29 | 3-Methoxy-propylamine | 2-(3-{3-[(2-Chloro-3-trifluoromethyl-benzyl)-diphenylethyl-amino]-propoxy}-phenyl)-N-(3-methoxy-propyl)-acetamide hydrochloride salt | 667.6 $(M^+)$ |
| 30 | (5-Methyl-[1,3,4]oxadiazol-2-yl)-methylamine | 2-(3-{3-[(2-Chloro-3-trifluoromethyl-benzyl)-diphenylethyl-amino]-propoxyl]-phenyl)-N-(5-methyl-[1,3,4] oxadiazol-2-ylmethyl)-acetamide hydrochloride salt | 677.2 $(M^+)$ |
| 31 | (4-Methyl-thiazol-2-yl)-methylamine | 2-(3-{3-[(2-Chloro-3-trifluoromethyl-benzyl)-diphenylethyl-amino]-propoxy}-phenyl)-N-(4-methyl-thiazol-2-ylmethyl)-acetamide hydrochloride salt | 692.4 $(M^+)$ |
| 32 | 1-Thiophen-2-yl-ethylamine | 2-(3-{3-[(2-Chloro-3-trifluoromethyl-benzyl)-diphenylethyl-amino]-propoxy}-phenyl)-N-(1-thiophen-2-yl-ethyl)-acetamide hydrochloride salt | 691.4 $(M^+)$ |
| 33 | Thiophen-3-yl-methylamine | 2-(3-{3-[(2-Chloro-3-trifluoromethyl-benzyl)-diphenylethyl-amino]-propoxy}-phenyl)-N-thiophen-3-ylmethyl-acetamide hydrochloride salt | 677.2 $(M^+)$ |
| 34 | (5-Methyl-4H-[1,2,4]triazol-3-yl)-methylamine | 2-(3-{3-[(2-Chloro-3-trifluoromethyl-benzyl)-diphenylethyl-amino]-propoxy}-phenyl)-N-(5-methyl-4H-[1,2,4]triazol-3-ylmethyl)-acetamide hydrochloride salt | 676.2 $(M^+)$ |
| 35 | Pyridin-2-yl-methylamine | 2-(3-{3-[(2-Chloro-3-trifluoromethyl-benzyl)-diphenylethyl-amino]-propoxy}-phenyl)-N-pyridin-2-ylmethyl-acetamide hydrochloride salt | 672.4 $(M^+)$ |
| 36 | (Tetrahydro-furan-2-yl)-methylamine | 2-(3-{3-[(2-Chloro-3-trifluoromethyl-benzyl)-diphenylethyl-amino]-propoxy}-phenyl)-N-(tetrahydro-furan-2-ylmethyl)-acetamide hydrochloride salt | 665.4 $(M^+)$ |
| 37 | (1-Ethyl-pyrrolidin-2-yl)-methylamine | 2-(3-{3-[(2-Chloro-3-trifluoromethyl-benzyl)-diphenylethyl-amino]-propoxy}-phenyl)-N-(1-ethyl-pyrrolidin-2-ylmethyl)-acetamide hydrochloride salt | 692.4 $(M^+)$ |
| 38 | Octylamine | 2-(3-{3-[(2-Chloro-3-trifluoromethyl-benzyl)-diphenylethyl-amino]-propoxy}-phenyl)-N-octyl-acetamide hydrochloride salt | 693.4 $(M^+)$ |
| 39 | Decylamine | 2-(3-{3-[(2-Chloro-3-trifluoromethyl-benzyl)-diphenylethyl-amino]-propoxy}-phenyl)-N-decyl-acetamide hydrochloride salt | 721.2 $(M^+)$ |
| 40 | 2-(2-Amino-ethoxy)-ethanol | 2-(3-{3-[(2-Chloro-3-trifluoromethyl-benzyl)-diphenylethyl-amino]-propoxy}-phenyl)-N-[2-(2-hydroxy-ethoxy)-ethyl]-acetamide hydrochloride salt | 669.2 $(M^+)$ |
| 41 | 2-Amino-2-thiophen-2-yl-acetic acid | [2-(3-{3-[(2-Chloro-3-trifluoromethyl-benzyl)-diphenylethyl-amino]-propoxy}-phenyl)-ethanoylamino]-2-thiophen-2-yl-acetic acid hydrochloride salt | 721.2 $(M^+)$ |

EXAMPLE 42

3-[2-(3-{3-[(2-Chloro-3-trifluoromethyl-benzyl)diphenylethyl-amino]-propoxy}-phenyl)-ethanoylamino]-propionic acid hydrochloride salt

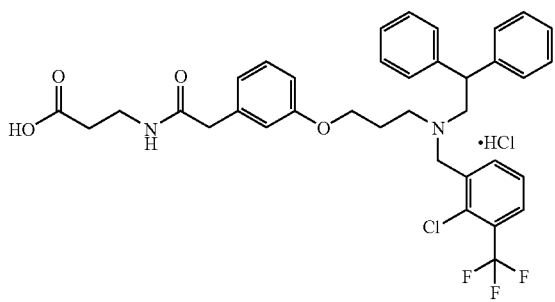

a) 3-[2-(3-{3-[(2-Chloro3-trifluoromethyl-benzyl)-diphenylethyl-amino]-propoxy}-phenyl)-ethanoylamino]-propionic acid tert-butyl ester Following the procedure of Example 1 steps (a)–(e) expect 3-amino-propionic acid tert-butyl ester hydrochloride was used in step 1(e) instead of morpholine the title compound was synthesized as an oil, 110 mg (96%). MS(ES) m/e 709.0 $(M^+)$.

b) 3-[2-(3-{3-[(2-Chloro-3-trifluoromethyl-benzyl)-diphenylethyl-amino]-propoxy}-phenyl)-ethanoylamino]-propionic acid hydrochloride salt To a stirring solution of 3-[2-(3-{3-[(2-Chloro-3-trifluoromethyl-benzyl)-diphenylethyl-amino]-propoxy}-phenyl)-ethanoylamino]-propionic acid tert-butyl ester (110 mg, 0.15 mmol) in $Et_2O$ (5 mL) was added 1M HCl in $Et_2O$ (0.46 ml, 0.46 mmol). The mixture was stirred at room temperature for 18 hours. Purification by preparative HPLC (YMC, 75×30 mm, 25 ml/min, 40–100% $CH_3CN:H_2O$) afforded the desired carboxylic acid. Treatment of the tertiary amine/ carboxylic acid with 1 N HCl (Et₂O) followed by concentration in vacuo afforded the title compound as a yellow solid (84 mg, 79%). MS(ES) m/e 653.4 (M⁺).

EXAMPLE 43

3-[2-(3-{3-[(2-Chloro-3-trifluoromethyl-benzyl)-diphenylethyl-amino]-propoxy}-phenyl)-ethanoylamino]-acetic acid hydrochloride salt

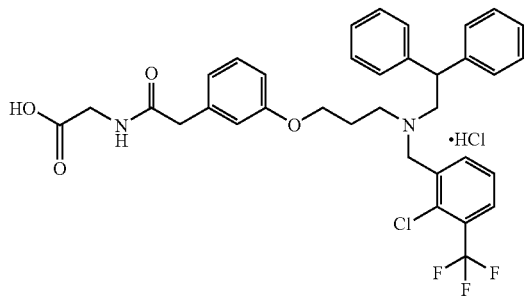

Following the procedure of Example 42 steps (a)–(b) except 3-amino-acetic acid tert-butyl ester hydrochloride was used in step 41(a) instead of 3-amino-propionic acid tert-butyl ester hydrochloride the title compound was obtained as a yellow solid (77 mg, 79% for two steps). MS(ES) m/e 639.4 (M⁺).

EXAMPLE 44

(R)-2-(3-{3-[(2-Chloro-3-(trifluoromethyl)-benzyl)-(2,2-diphenylethyl)-amino]-2-methyl-propoxy}phenyl)-1-morpholin-4-yl-ethanone hydrochloride salt

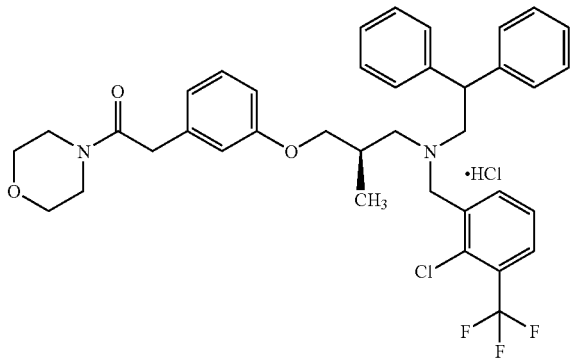

a) (3-Hydroxy-phenyl)-acetic acid methyl ester

To a stirring solution of (3-hydroxy-phenyl)-acetic acid (4.3 g, 0.028 mole) in methanol (30 mL) was added H₂SO₄ (1 mL) and the mixture was heated to reflux for 2 hours. The solvent was removed, the residue was washed with H₂O, and extracted three times with EtOAc (ethyl acetate). The combined organic layers were dried over Na₂SO₄, filtered, and concentrated to give 4.7 g (99% yield) of the title compound as an oil. MS (ESI) 167.0(M+H⁺).

b) (S)-[3-(2-Methyl-3-bromopropoxy)phenyl]acetic acid methyl ester

To a stirring solution of (3-hydroxy-phenyl)-acetic acid methyl ester (0.75 g, 0.0045 mol) in anhydrous toluene (30 mL) was added (S)-(+)-3-bromo-2-methyl-1-propanol (0.90 g, 0.0059 mol). Polymer bound triphenylphosphine (2.4 g, 0.0072 mole, 3 mmol/g, Fluka Chemie) was then added, and the mixture was stirred for 15 minutes. The reaction mixture was then cooled to 0° C. and diisopropylazodicarboxylate (1.1 g, 0.0056 mol) was added in a dropwise fashion. After stirring at room temperature overnight, the crude reaction mixture was filtered, and the solid washed with toluene. After concentration of the filtrate in vacuo, the crude product was purified by column chromatography over silica gel (silica gel 60, EM Science) using 15% EtOAc:hexane as eluent to afford 0.86 g (63% yield) of the title compound as an oil: MS (ESI) 303.0 (M+2H⁺).

c) N-(2,2-Diphenylethyl)-N-(2-chloro-3-trifluoromethyl-benzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36 g, 0.011 mole) and acetic acid (2.0 mL). The reaction mixture was stirred overnight. Solvent was removed, the residue was washed with saturated NaHCO₃, and extracted three times with EtOAc. The organic extracts were dried over Na₂SO₄, filtered, and concentrated. The crude mixture was subjected to column chromatography over silica gel (silica gel 60, EM Science) using 30% EtOAc:hexane as eluent to afford 3.0 g (76% yield) of the title compound as a yellow oil: MS (ESI) 390.0 (M+H⁺).

d) (R)-2-(3-{3-[[2-Chloro-3-(trifluoromethyl)benzyl](2,2-diphenylethyl)amino]-2-methyl-propoxy}-phenyl)acetic acid methyl ester To a stirring solution of (S)-[3-(2-methyl-3-bromopropoxy)phenyl]acetic acid methyl ester (100 mg, 0.33 mmol) and N-(2,2-diphenylethyl)-N-(2-chloro-3-trifluoromethyl)amine (130 mg, 0.33 mmol) in acetonitrile (5 mL) was added solid K₂CO₃ (138 mg, 1.0 mmol) and NaI (149 mg, 1.0 mmol). The reaction was heated to reflux and stirred overnight. Upon cooling to room temperature, the reaction was filtered, washed with acetonitrile, and the filtrate was concentrated. The crude product was purified by preparative HPLC (TMC CombiPrep PDS, 75×30 mm, 25 mL/min, acetonitrile: H₂O, UV detection at 254 nm) to give 29 mg (14% yield) of title compound as a viscous oil. MS(ESI) 610.2(M⁺).

e) (R)-2-(3-{3-[[2Chloro-3-(trifluoromethyl)benzyl](2,2-diphenylethyl)amino]-2-methyl-propoxy}-phenyl)acetic acid hydrochloride salt To a stirring solution of (R)-2-(3-{3-[[2-chloro-3-(trifluoromethyl)benzyl](2,2-diphenylethyl)amino]-2-methyl-propoxy}-phenyl)acetic acid methyl ester (22 mg, 0.0361 mmol) in THF (0.75 ml) and water (0.25 ml) was added LiOH (3.0 mg, 0.072 mmol). The reaction mixture was stirred overnight at RT. The reaction mixture was concentrated and 3 N HCl (aq.) was added until the pH was less than two. The aqueous layer was extracted three times with EtOAc, the combined organic layers were dried over sodium sulfate, filtered, and concentrated in vacuo. The resulting amine/carboxylic acid was dissolved in Et$_2$O and acidified with 1.0 M HCl/Et$_2$O. The reaction mixture was concentrated in vacuo and dried under reduced pressure to give 18 mg (78% yield) of the title compound as a white solid. MS(ESI) 596.0(M$^+$).

f) (R)-2-(3-{3-[(2Chloro-3-(trifluoromethyl)-benzyl)-(2,2-diphenylethyl)-amino]-2-methyl-propoxy}phenyl)-1-morpholin-4-yl-ethanone hydrochloride salt Following the procedure of Example 1 step (e) except (R)-2-(3-{3-[[2-chloro-3-(trifluoromethyl)benzyl](2,2-diphenylethyl)amino]-2-methyl-propoxy}-phenyl)acetic acid was used in step 1(e) instead of 2-(3-{3-[[2-chloro-3-(trifluoromethyl)benzyl](2,2-diphenylethyl)-amino]-propoxy}-phenyl acetic acid the title compound was prepared as a white solid (80%). MS(ESI) 665.4 (M$^+$).

EXAMPLE 45

2-(3-{(R)-3-[(2-Chloro-3-trifluoromethyl-benzyl)-diphenylethyl-amino]-butoxy}-phenyl)-1-morpholin-4-yl-ethanone hydrochloride salt

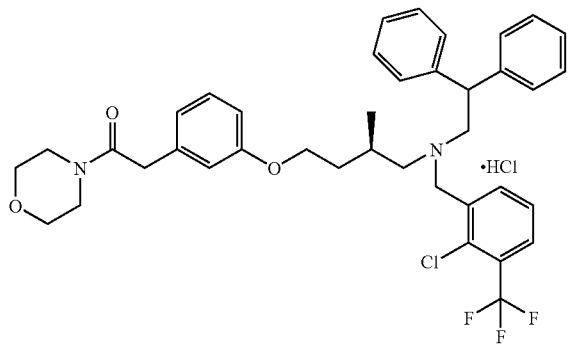

a) (S)-[3-(3-Hydroxy-butoxy)phenyl]-acetic acid methyl ester

To a stirring solution of (S)-1,3-butanediol (1.0 g, 0.01 mmol) and triethylamine (1.39 g, 0.014 mmol) in dichloromethane (10 mL) at −20° C. was added dropwise p-toluenesulfonyl chloride and the mixture was stirred for 2 h. The reaction mixture was then warmed to RT and stirred overnight. The reaction mixture was poured into cold H$_2$O (20 mL), and extracted three times with dichloromethane. The organic extracts were then washed with brine. The organic layer was dried over sodium sulfate, filtered, and concentrated in vacuo to give 2.6 g (96% yield) of title compound as an oil. MS(ESI) 244.8(M$^+$). The crude tosylate was used without further purification.

To a stirring solution of (3-hydroxy-phenyl)-acetic acid methyl ester (0.93 g, 0.0056 mole) and toluene-4-sulfonic acid-(S)-3-hydroxy-butyl ester (1.5 g, 0.0061 mole) (from above) in anhydrous DMF (10 mL) was added Cs$_2$CO$_3$ (2.0 g, 0.006 mole). The reaction was heated to 100° C. and stirred for 4 hours. The mixture was cooled to RT and filtered. The filtrate was poured into H$_2$O (50 mL) and extracted three times with EtOAc. The combined organic layers were dried over sodium sulfate, filtered, and concentrated. The crude product was subjected to column chromatography over silica gel (silica gel 60, EM Science) using 30% EtOAc:hexane as eluent to afford 0.59 g (44% yield) of the title compound as an oil: MS (ESI) 239.0 (M+H$^+$).

b) (S)-{3-[3-(Toluene-4-sulfonyloxy)-butoxy]-phenyl}-acetic acid methyl ester

To a stirring solution of (S)-[3-(3-hydroxy-butoxy)-phenyl]-acetic acid methyl ester (589 mg, 2.47 mmol) and triethylamine (376 mg, 3.71 mmol) in dichloromethane (10 mL) at 0° C. was added p-toluenesulfonyl chloride (944 mg, 4.95 mmol). The reaction was then stirred at RT for 30 min. and refluxed overnight. The reaction mixture was poured into H$_2$O (40 mL) and extracted three times with dichloromethane. The combined organic extracts were dried over sodium sulfate, filtered, and concentrated. The crude product was purified by column chromatography over silica gel (silica gel 60, EM Science) using 15% EtOAc:hexane as eluent to afford 0.61 g (63% yield) of the title compound as an oil: MS (ESI) 393.0 (M+H$^+$).

c) (R)-2-(3-{3-[(2,2-Diphenylethyl)amino]-3-methyl-propoxy}-phenyl)acetic acid methyl ester To a stirring solution of 2,2-diphenethylamine (151 mg, 0.765 mmol) and (S)-{3-[3-(toluene-4-sulfonyloxy)-butoxy]-phenyl}-acetic acid methyl ester (300 mg, 0.765 mmol) in acetonitrile (5 mL) was treated with solid K$_2$CO$_3$ (317 mg, 2.30 mmol). The reaction was heated to reflux and stirred for 48 hours. Upon cooling to room temperature, the reaction mixture was filtered, washed with acetonitrile, and the filtrate was concentrated. The crude product was purified by column chromatography over silica gel (silica gel 60, EM Science) using 50% EtOAc:hexane as eluent to afford 200 mg (63% yield) of the title compound as an oil: MS (ESI) 418.2 (M+H$^+$).

d) (R)-2-(3-{3-[[2-Chloro-3-(trifluoromethyl)benzyl](2,2-diphenylethyl)amino]-3-methyl-propoxy}-phenyl)acetic acid methyl ester To a stirring solution of (R)-2-(3-{3-(2,2-diphenylethyl)amino]-3-methyl-propoxy}-phenyl)acetic acid methyl ester (150 mg, 0.359 mmol) and 2-chloro-3-trifluoromethylbenzaldehyde (164 mg, 0.79 mmol) in dichloromethane (5 ml) was added sodium triacetoxyborohydride (168 mg, 0.79 mmol) and acetic acid (10 drops). The reaction mixture was stirred at RT for three days. The reaction mixture was concentrated, the residue was dissolved in EtOAc, and then washed with saturated aqueous NaHCO$_3$. The EtOAc layer was dried over Na$_2$SO$_4$, filtered, and concentrated. The crude mixture was purified by preparative HPLC (TMC CombiPrep PDS, 75×30 mm, 25 mL/min, acetonitrile: H$_2$O, UV detection at 254 nm) to give 140 mg (64%) of the title compound as a viscous oil. MS(ESI) 610.0(M$^+$).

e) (R)-2-(3-{3-[[2Chloro-3-(trifluoromethyl)benzyl](2,2-diphenylethyl)amino]-3-methyl-propoxy}-phenyl)acetic acid hydrochloride salt Following the procedure of Example 44 step(e) except (R)-2-(3-{3-[[2-chloro-3-(trifluoromethyl)benzyl](2,2-diphenylethyl)amino]-3-methyl-propoxy}-phenyl)acetic acid methyl ester was used in step 44(e) instead of (R)-2-(3-{3-[[2-chloro-3-(trifluoromethyl)benzyl](2,2-diphenylethyl)amino]-2-methyl-propoxy}-phenyl)acetic acid methyl ester the title compound was isolated to give a white solid (100 mg, 89%). MS(ESI) 596.0 (M+).

f) 2-(3-{(R)-3-[(2Chloro-3-trifluoromethyl-benzyl)-diphenylethyl-amino]-butoxy}-phenyl)-1-morpholin-4-yl-ethanone hydrochloride salt Following the procedure of Example 1 step (e) except (R)-2-(3-{3-[[2-Chloro-3-(trifluoromethyl)benzyl](2,2-diphenylethyl)amino]-3-methyl-propoxy}-phenyl)acetic acid was used instead of 2-(3-{3-[[2-chloro-3-(trifluoromethyl)benzyl)(2,2-diphenylethyl)-amino]-propoxy}-phenyl acetic acid in step 1(e) the title compound was prepared as a white solid (80%). MS(ESI) 665.4 (M+).

EXAMPLE 46

4-{3-[(2Chloro-3-trifluoromethyl-benzyl)-diphenylethyl-amino]-propoxy}-N,N-dimethyl-benzamide

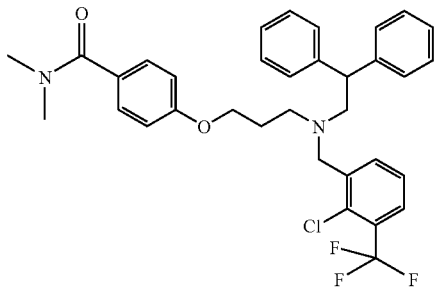

a) (2,2-Diphenylethyl)(2-chloro-3-trifluoromethyl-benzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36 g, 0.011 mole) and acetic acid (2.0 mL). The reaction mixture was stirred overnight. The solvent was removed and the residue was dissolved in ethyl acetate. The ethyl acetate solution was washed with saturated NaHCO₃, the ethyl acetate extracts were dried over Na₂SO₄, filtered, and concentrated. The crude product was subjected to column chromatography over silica gel (silica gel 60, EM Science) using 30% ethyl acetate:hexane as eluent to afford 3.0 g (76% yield) of the title compound as a yellow oil: MS (ESI) 390.0 (M+H+).

b) N-(2,2-Diphenylethyl)-N-(3-hydroxy-propyl)-N-(2-chloro-3-trifluoromethyl-benzyl)amine To a stirring solution of 3-bromo-propanol (77 ul, 0.84 mmol) in acetonitrile (10 ml) was added NaI (0.25 g, 1.7 mmol) and K₂CO₃ (0.23 g, 1.7 mmol). The mixture was stirred at 85° C. for 1 h, and then N-(2,2-diphenylethyl)-N-(2-chloro-3-trifluoromethyl-benzyl)amine (0.43 g, 1.12 mmol) was added. The reaction mixture was heated at 85° C. overnight. The reaction mixture was concentrated, the residue was dissolved in EtOAc, and washed with H₂O. The EtOAc extracts were dried over Na₂SO₄, filtered, and concentrated. The crude mixture was purified by preparative HPLC (TMC CombiPrep PDS, 75×30 mm, 25 mL/min, acetonitrile:H₂O, UV detection at 254 nm) to give 225 mg (60%) of the title compound as a white solid. MS (ESI) 448.0 (M+H+).

c) 4-{3-[(2-Chloro-3-trifluoromethyl-benzyl)-diphenylethyl-amino]-propoxy}-benzoic acid methyl ester To a solution of N-(2,2-diphenylethyl)-N-(3-hydroxy-propyl)-N-(2-chloro-3-trifluoromethyl-benzyl)amine (0.60 g, 1.33 mmol) in toluene (4 ml) at ambient temperature was added 4-hydroxy-benzoic acid methyl ester (0.22 g, 1.45 mmol) under Argon with stirring. The mixture was treated with polymer bound PPh₃ (0.71 g, 2.13 mmol). After 15 minutes of stirring the mixture was treated with DIAD (0.32 mL, 1.66 mmol) and was stirred at room temperature overnight. The reaction mixture was filtered, and concentrated in-vacuo. The resulting oil was dissolved in DMSO and was purified via preparative reverse-phase HPLC (TMC CombiPrep PDS, 75×30 mm, 25 mL/min, acetonitrile:H₂O, UV detection at 254 nm) to yield the title compound, 0.24 g (32%); MS (ESI) m/e 583 [M+H]+.

d) 4-{3-[(2Chloro-3-trifluoromethyl-benzyl)-diphenylethyl-amino]-propoxy}-benzoic acid A solution of 4-{3-[(2-Chloro-3-trifluoromethyl-benzyl)-diphenylethyl-amino]-propoxy}-benzoic acid methyl ester (0.20 g, 0.34 mmol) in tetrahydrofuran (7.5 mL) and H₂O (2.5 mL) at ambient temperature was treated with LiOH.H₂O (0.029 g, 0.68 mmol). The mixture was stirred overnight at ambient temperature. The mixture was then treated with additional LiOH.H₂O (0.058 g, 1.37 mmol) and heated at 50° C. overnight. The reaction was cooled to 0° C. and was quenched with H₂O (5 mL). The mixture was the acidified to a pH=2 with 1 N HCl (aq.). The mixture was then extracted three times with EtOAc, dried, filtered and concentrated in-vacuo to afford the carboxylic acid product. The acid was purified via reverse-phase HPLC (TMC CombiPrep PDS, 75×30 mm, 25 mL/min, acetonitrile:H₂O, UV detection at 254 nm) to yield the title compound, 0.140 g (72%); MS (ESI) m/e 569 [M+H]+.

e) 4-{3-[(2-Chloro-3-trifluoromethyl-benzyl)-diphenylethyl-amino]-propoxy}-N,N-dimethyl-benzamide A solution of 4-{3-[(2-Chloro-3-trifluoromethyl-benzyl)-diphenylethyl-amino]-propoxy}-benzoic acid (0.023 g, 0.041 mmol) in acetonitrile (3 ml) was treated with BOP reagent (0.02 g, 0.04 mmol) followed by triethylamine (0.013 mL, 0.09 mmol). To the mixture was added (CH₃)₂NH₂.HCl (4 mg, 0.045 mmol), and the reaction was stirred at ambient temperature overnight. The reaction mixture was then concentrated in-vacuo to afford an oil. The crude product was then dissolved in DMSO and purified via reverse-phase HPLC (TMC CombiPrep PDS, 75×30 mm, 25 mL/min, acetonitrile:H₂O, UV detection at 254 nm) to afford the title compound, 186 mg (77%); MS (ESI) m/e 596 [M+H]+.

EXAMPLE 47

1-(4-{3-[(2-Chloro-3-trifluoromethyl-benzyl)-diphenylethyl-amino]-propoxy}-phenyl)-1-morpholin-4-yl-methanone

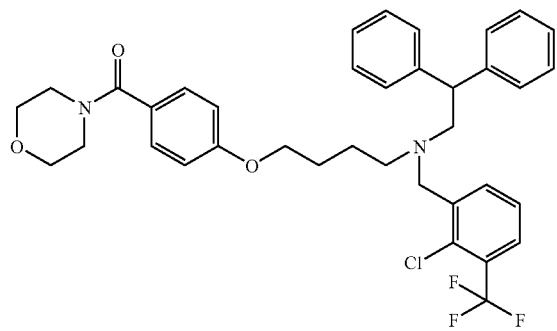

Following the procedure of Example 46 steps (a)–(e) except morpholine was used in step 46(e) instead of dimethylamine the title compound was prepared (9%). MS (ESI) m/e 638 [M+H]+

EXAMPLE 48

1-(4-{3-[(2-Chloro-3-trifluoromethyl-benzyl)-diphenylethyl-amino]-propoxy}-phenyl)-1-(4-methyl-piperazin-1-yl)-methanone

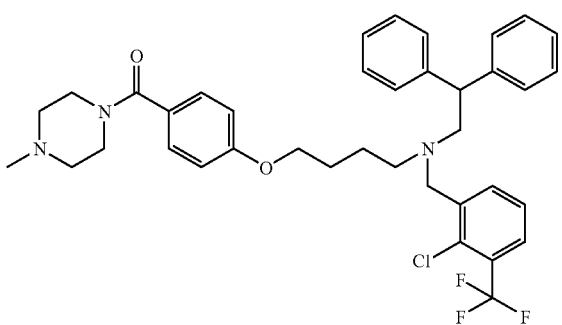

Following the procedure of Example 46 steps (a)–(e) except N-methylpiperazine was used in step 46(e) instead of dimethylamine the title compound was prepared (10%). MS (ESI) m/e 651 [M+H]+

EXAMPLE 49

3-{3-[(2-Chloro-3-trifluoromethyl-benzyl)-diphenylethyl-amino]-propoxy}-N,N-dimethyl-benzamide

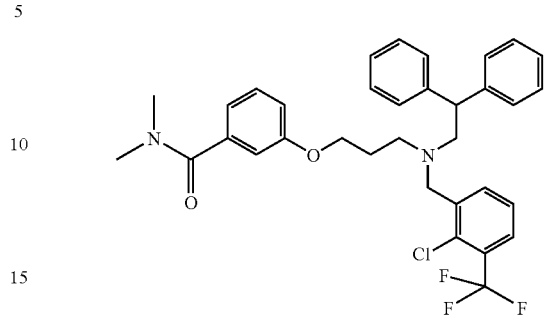

Following the procedure of Example 46 steps (a)–(e) except 3-hydroxy-benzoic acid methyl ester was used in step 46(c) instead of 4-hydroxy-benzoic acid methyl ester the title compound was prepared (10%). MS (ESI) m/e 596 [M+H]+.

EXAMPLE 50

3-{3-[(2Chloro-3-trifluoromethyl-benzyl)diphenylethyl-amino]-propoxy}-N-phenyl-benzamide

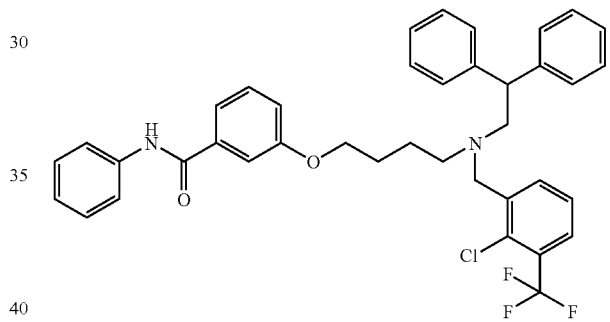

Following the procedure of Example 46 steps (a)–(e) except 3-hydroxy-benzoic acid methyl ester was used in step 46(c) instead of 4-hydroxy-benzoic acid methyl ester, and aniline was used in step 46(e) instead of dimethylamine the title compound was prepared (10%). MS(ESI) m/e 644 [M+H]+.

EXAMPLE 51

1-(3-{3-[(2-Chloro-3-tifluoromethyl-benzyl)-diphenylethyl-amino]-propoxy}-phenyl)-1-morpholin-4-yl-methanone

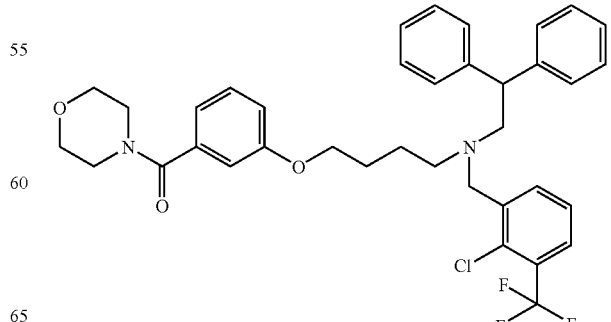

Following the procedure of Example 46 steps (a)–(e) except 3-hydroxy-benzoic acid methyl ester was used in step 46(c) instead of 4-hydroxy-benzoic acid methyl ester, and morpholine was used in step 46(e) instead of dimethylamine the title compound was prepared (11%). MS (ESI) m/e 638 [M+H]+.

EXAMPLE 52

1-(3-{3-[(2Chloro-3-trifluoromethyl-benzyl)-diphenylethyl-amino]-propoxy}-phenyl)-1-(4-methyl-piperazin-1-yl)-methanone

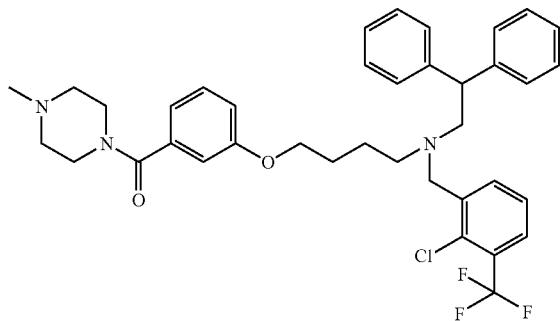

Following the procedure of Example 46 steps (a)–(e) except 3-hydroxy-benzoic acid methyl ester was used in step 46(c) instead of 4-hydroxy-benzoic acid methyl ester, and N-methylpiperazine was used in step 46(e) instead of dimethylamine the title compound was prepared (10%). MS (ESI) m/e 651 [M+H]+.

EXAMPLE 53

N-[1-(3-{3-[(2-Chloro-3-trifluoromethyl-benzyl)-diphenylethyl-amino]-propoxy}-phenyl)-methanoyl]-methanesulfonamide

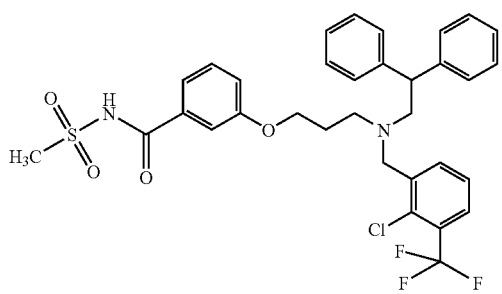

Following the procedure of Example 46 steps (a)–(e) except 3-hydroxy-benzoic acid methyl ester was used in step 46(c) instead of 4-hydroxy-benzoic acid methyl ester, and methanesulfonamide was used in step 46(e) instead of dimethylamine the title compound was prepared (10%). MS (ESI) m/e 646 [M+H]+.

EXAMPLE 54

N-[1-(3-{3-[(2-Chloro-3-trifluoromethyl-benzyl)-diphenylethyl-amino]-propoxy}-phenyl)-methanoyl]-benzenesulfonamide

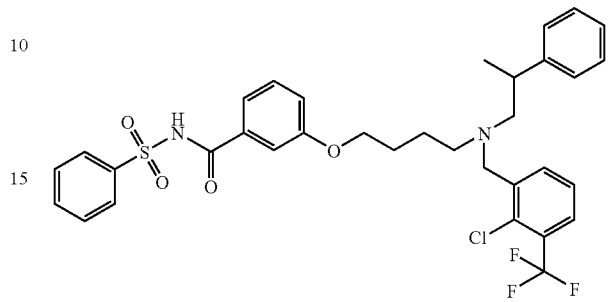

Following the procedure of Example 46 steps (a)–(e) except 3-hydroxy-benzoic acid methyl ester was used in step 46(c) instead of 4-hydroxy-benzoic acid methyl ester, and benzenesulfonamide was used in step 46(e) instead of dimethylamine the title compound was prepared (10%). MS (ESI) m/e 708 [M+H]+.

EXAMPLE 55

N-[2-(3-{3-[(2-Chloro-3-tifluoromethyl-benzyl)-diphenylethyl-amino]-propoxy}-phenyl)-ethanoyl]-methanesulfonamide

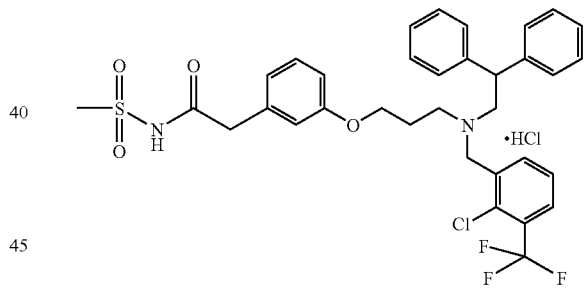

N-[2-3-{3-[(2Chloro-3-trifluoromethyl-benzyl)-diphenyl-ethyl-amino]-propoxy}-phenyl)-ethanoyl]-methanesulfonamide Diisopropylethylamine (224 µL, 1.29 mmol) was added in one portion to a stirred suspension of (3-{3-[(2-Chloro-3-trifluoromethyl-benzyl)-diphenylethyl-amino]-propoxy}-phenyl)-acetic acid (159.4 mg, 0.26 mmol—Example 1(a)–(d)), PyBOP® (202.1 mg, 0.39 mmol), and methylsulfonamide (36.8 mg, 0.30 mmol) in dichloromethane (2 mL). The resulting clear solution was left at ambient temperature for 18 h. The reaction mixture was concentrated to provide a syrup (588.1 mg). The crude product was purified by preparative HPLC (Phenomenx Luna Combi-HTS 30×75 mm, 5 µ, $C_{18}$, 40 ml/min, A: acetonitrile B: water, A 20 to 98% over 12 min, UV detection 214 nm). The tertiary amine was treated with 1 N HCl in $Et_2O$, and then concentrated in vacuo to provide the title compound, 37.1 mg (20%). mp 170° C. MS (ESI) 659.0 (M+H+).

EXAMPLE 56

N-[2-(3-{3-[(2-Chloro-3-trifluoromethyl-benzyl)-diphenylethyl-amino]-propoxy}-phenyl)-ethanoyl]-benzenesulfonamide

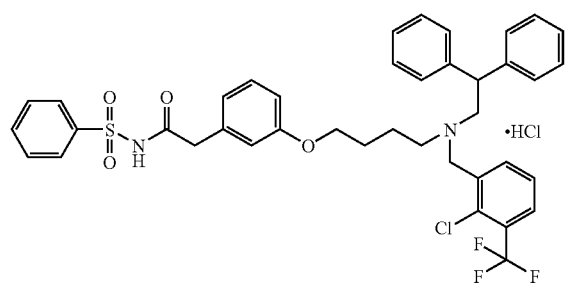

Following the procedure of Example 55 except benzenesulfonamide was used instead of methanesulfonamide the title compound was prepared, 120 mg (65%). mp 110° C. MS (ES+) m/e 721 [M+].

EXAMPLE 57

N-[-(3-{3-[(2-Chloro-3-trifluoromethyl-benzyl)-diphenylethyl-amino]-propoxy}-phenyl-ethanoyl]-N-methyl-benzenesulfonamide

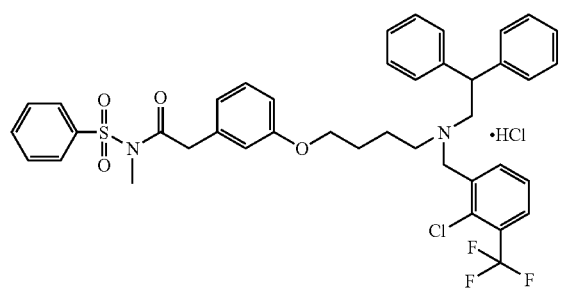

Following the procedure of Example 55 except N-methyl-benzenesulfonamide was used instead of methanesulfonamide the title compound was prepared, 75.1 mg (19%). MS (ESI) 735.0 (M+H+).

EXAMPLE 58

N-[2-(3-{3-[(Chlorotrifluoromethyl-benzyl)-diphenylethyl-amino]-propoxy}-phenyl)-ethanoyl]-N-methyl-methanesulfonamide

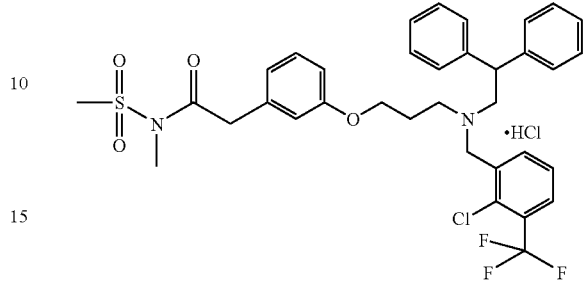

Following the procedure of Example 55 except N-methyl-methanesulfonamide was used instead of methanesulfonamide the title compound was prepared, 62.1 mg (34%). MS (ESI) 673.0 (M+H+).

EXAMPLE 59

2-(3-{3-[(2-Chloro-3-trifluoromethyl-benzyl)-((S)-2-phenyl-propyl)-amino]-propoxy}-phenyl)-1-morpholin-4-yl-ethanone hydrochloride salt

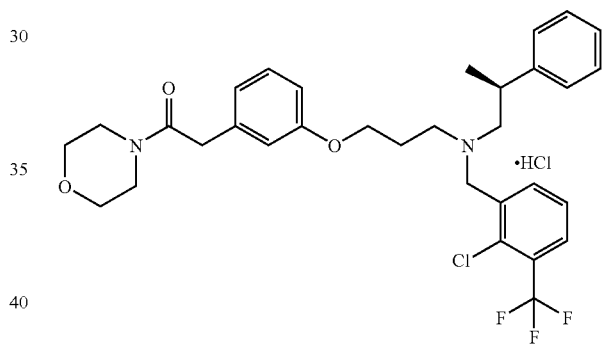

Following the procedure of Example 11 steps (a)–(e) except morpholine was used in step 11(e) instead of ammonia the title compound was synthesized as a white solid. MS m/e 589.2(M+H)+.

EXAMPLE 60

2-(3-{3-[(2-Chloro-3-trifluoromethyl-benzyl)-((S)-2-phenyl-propyl)-amino]-propoxy}-phenyl)-N-ethyl-acetamide hydrochloride salt

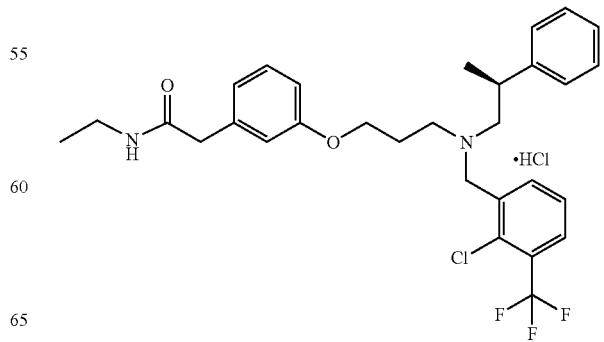

Following the procedure of Example 11 steps (a)–(e) except ethylamine was used in step 11(e) instead of ammonia the title compound was synthesized as a white solid, 35 mg (45%). MS m/e 547.2 (M+).

EXAMPLE 62

2-(3-{3-[(2-Chloro-3-trifluoromethyl-benzyl)-((R)-2-phenyl-propyl)-amino]-propoxy}-phenyl)-N,N-dimethyl-acetamide

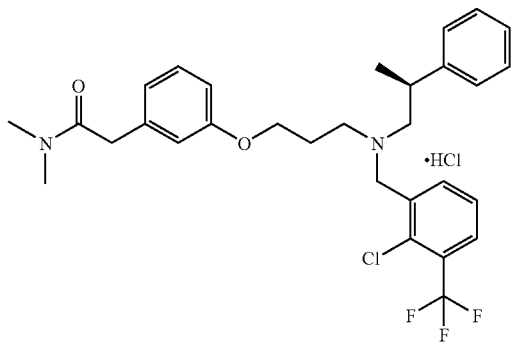

Following the procedure of Example 11 steps (a)–(e) except dimethylamine was used in step 11(e) instead of ammonia the title compound was synthesized as a white solid, 35 mg (45%). MS m/e 548.2 (M+H)+.

EXAMPLE 63

2-(3-{3-[(2-Chloro-3-trifluoromethyl-benzyl)-((R)-2-phenyl-propyl)-amino]-propoxy}-phenyl)acetamide hydrochloride salt

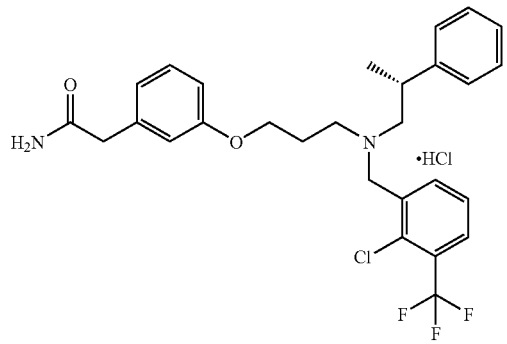

Following the procedure of Example 11 steps (a)–(e) except (R)-2-phenyl propylamine was used in step 11(a) instead of (S)-2-phenyl propylamine, the title compound was synthesized as a white solid, 32 mg (60%). MS m/e 519.6 (M+).

EXAMPLE 64

2-(3-{3-[(2-Chloro-3-trifluoromethyl-benzyl)-((R)-2-phenyl-propyl)-amino]-propoxy}-phenyl)-N-methyl-acetamide hydrochloride salt

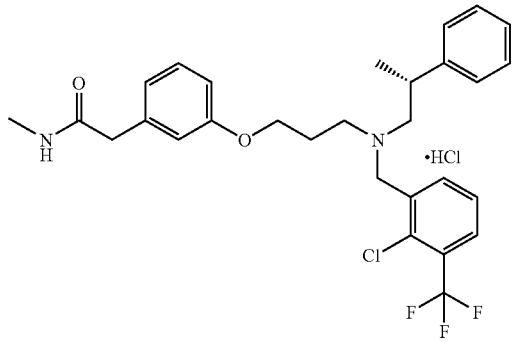

Following the procedure of Example 11 steps (a)–(e) except (R)-2-phenyl propylamine was used in step 11(a) instead of (S)-2-phenyl propylamine and methylamine was used in step 11(e) instead of ammonia, the title compound was synthesized as a white solid, 36 mg (65%). MS m/e 534.0 (M+).

EXAMPLE 65

2-(3-{3-[(2-Chloro-3-trifluoromethyl-benzyl)-((R)-2-phenyl-propyl)-amino]-propoxy}-phenyl)-N,N-dimethyl-acetamide hydrochloride salt

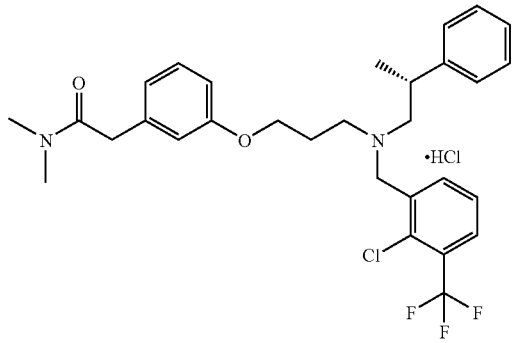

Following the procedure of Example 11 steps (a)–(e) except (R)-2-phenyl propylamine was used in step 11(a) instead of (S)-2-phenyl propylamine and dimethylamine was used in step 11(e) instead of ammonia, the title compound was synthesized as a white solid, 25 mg (50%). MS m/e 547.0 (M+).

The above description fully discloses how to make and use the present invention. However, this invention is not limited to the particular embodiments described hereinabove, but includes all modification thereof within the scope of the appended claims and their equivalents. Those skilled in the art will recognize through routine experimentation that various changes and modifications can be made without departing from the scope of this invention. The various references to journals, patents and other patent applications that are cited herein are incorporated by reference herein as though fully set forth.

What is claimed is:

1. A compound of Formula I:

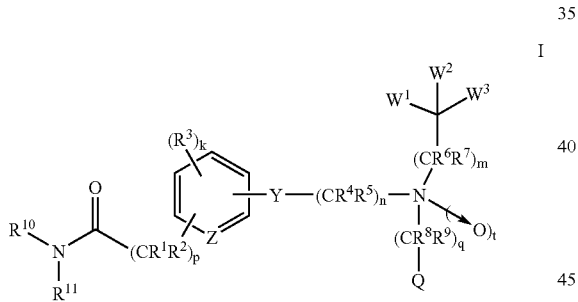

wherein:
 Z is CH, $CR^3$ or N, wherein when Z is CH or $CR^3$, k is 0–4 and t is 0 or 1, and when Z is N, k is 0–3 and t is 0;
 Y is selected from —O—, —S—, —N($R^{12}$)—, and —C($R^4$)($R^5$)—;
 $W^1$ is selected from $C_1$–$C_6$ alkyl, $C_0$–$C_6$ alkyl $C_3$–$C_8$ cycloalkyl, aryl and Het, wherein said $C_1$–$C_8$ alkyl, $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-CONR$^{13}R^{14}$, —$C_0$–$C_6$ alkyl-COR$^{15}$, —$C_0$–$C_6$ alkyl-NR$^{13}R^{14}$, —$C_0$–$C_6$ alkyl-SR$^{12}$, —$C_0$–$C_6$ alkyl-OR$^{12}$, —$C_0$–$C_6$ alkyl-SO$_3$H, —$C_0$–$C_6$ alkyl-SO$_2$NR$^{13}R^{14}$, —$C_0$–$C_6$ alkyl-SO$_2R^{12}$, —$C_0$–$C_6$ alkyl-SOR$^{15}$, —$C_0$–$C_6$ alkyl-OCOR$^{15}$, —$C_0$–$C_6$ alkyl-OC(O)NR$^{13}R^{14}$, —$C_0$–$C_6$ alkyl-OC(O)OR$^{15}$, —$C_0$–$C_6$ alkyl-NR$^{13}$C(O)OR$^{15}$, —$C_0$–$C_6$ alkyl-NR$^{13}$C(O)NR$^{13}R^{14}$, and —$C_0$–$C_6$ alkyl-NR$^{13}$COR$^{15}$, where said $C_1$–$C_6$ alkyl, is optionally unsubstituted or substituted by one or more halo substituents;
 $W^2$ is selected from H, halo, $C_1$–$C_6$ alkyl, $C_2$–$C_6$ alkenyl, $C_2$–$C_6$ alkynyl, —$C_0$–$C_6$ alkyl-NR$^{13}R^{14}$, —$C_0$–$C_6$ alkyl-SR$^{12}$, —$C_0$–$C_6$ alkyl-OR$^{12}$, —$C_0$–$C_6$ alkyl-$CO_2R^{12}$, —$C_0$–$C_6$ alkyl-C(O)$SR^{12}$, —$C_0$–$C_6$ alkyl-CONR$^{13}R^{14}$, —$C_0$–$C_6$ alkyl-COR$^{15}$, —$C_0$–$C_6$ alkyl-OCONR$^{13}R^{14}$, —$C_0$–$C_6$ alkyl-NR$^{13}$CONR$^{13}R^{14}$, —$C_0$–$C_6$ alkyl-NR$^{13}$COR$^{15}$, —$C_0$–$C_6$ alkyl-Het, —$C_0$–$C_6$ alkyl-Ar and —$C_0$–$C_6$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_6$ alkyl-Het, —$C_0$–$C_6$ alkyl-Ar and —$C_0$–$C_6$ alkyl-$C_3$–$C_7$ cycloalkyl are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-CONR$^{13}R^{14}$, —$C_0$–$C_6$ alkyl-COR$^{15}$, —$C_0$–$C_6$ alkyl-NR$^{13}R^{14}$, —$C_0$–$C_6$ alkyl-SR$^{12}$, —$C_0$–$C_6$ alkyl-OR$^{12}$, —$C_0$–$C_6$ alkyl-SO$_3$H, —$C_0$–$C_6$ alkyl-SO$_2$NR$^{13}R^{14}$, —$C_0$–$C_6$ alkyl-SO$_2R^{12}$, —$C_0$–$C_6$ alkyl-SOR$^{15}$, —$C_0$–$C_6$ alkyl-OCOR$^{15}$, —$C_0$–$C_6$ alkyl-OC(O)NR$^{13}R^{14}$, —$C_0$–$C_6$ alkyl-OC(O)OR$^{15}$, —$C_0$–$C_6$ alkyl-NR$^{13}$C(O)OR$^{15}$, —$C_0$–$C_6$ alkyl-NR$^{13}$C(O)NR$^{13}R^{14}$, and —$C_0$–$C_6$ alkyl-NR$^{13}$COR$^{15}$, where said $C_1$–$C_6$ alkyl, is optionally unsubstituted or substituted by one or more halo substituents;
 $W^3$ is selected from the group consisting of: H, halo, $C_1$–$C_6$ alkyl, —$C_0$–$C_6$ alkyl-NR$^{13}R^{14}$, —$C_0$–$C_6$ alkyl-SR$^{12}$, —$C_0$–$C_6$ alkyl-OR$^{12}$, —$C_0$–$C_6$ alkyl-$CO_2R^{12}$, —$C_0$–$C_6$ alkyl-C(O)$SR^{12}$, —$C_0$–$C_6$ alkyl-CONR$^{13}R^{14}$, —$C_0$–$C_6$ alkyl-COR$^{15}$, —$C_0$–$C_6$ alkyl-OCOR$^{15}$, —$C_0$–$C_6$ alkyl-OCONR$^{13}$R$^{14}$, —$C_0$–$C_6$ alkyl-NR$^{13}$CONR$^{13}$R$^{14}$, —$C_0$–$C_6$ alkyl-NR$^{13}$COR$^{15}$, —$C_0$–$C_6$ alkyl-Het, —$C_1$–$C_6$ alkyl-Ar and —$C_1$–$C_6$ alkyl-$C_3$–$C_7$ cycloalkyl, wherein said $C_1$–$C_6$ alkyl is optionally unsubstituted or substituted by one or more halo substituents;

Q is selected from $C_3$–$C_8$ cycloalkyl, Ar and Het; wherein said $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-CO$_2$R$^{12}$, —$C_0$–$C_6$ alkyl-C(O)SR$^{12}$, —$C_0$–$C_6$ alkyl-CONR$^{13}$R$^{14}$, —$C_0$–$C_6$ alkyl-COR$^{15}$, —$C_0$–$C_6$ alkyl-NR$^{13}$R$^{14}$, —$C_0$–$C_6$ alkyl-SR$^{12}$, —$C_0$–$C_6$ alkyl-OR$^{12}$, —$C_0$–$C_6$ alkyl-SO$_3$H, —$C_0$–$C_6$ alkyl-SO$_2$NR$^{13}$R$^{14}$, —$C_0$–$C_6$ alkyl-SO$_2$R$^{12}$, —$C_0$–$C_6$ alkyl-SOR$^{15}$, —$C_0$–$C_6$ alkyl-OCOR$^{15}$, —$C_0$–$C_6$ alkyl-OC(O)NR$^{13}$R$^{14}$, —$C_0$–$C_6$ alkyl-OC(O)OR$^{15}$, —$C_0$–$C_6$ alkyl-NR$^{13}$C(O)OR$^{15}$, —$C_0$–$C_6$ alkyl-NR$^{13}$C(O)NR$^{13}$R$^{14}$, and —$C_0$–$C_6$ alkyl-NR$^{13}$COR$^{15}$, where said $C_1$–$C_6$ alkyl is optionally unsubstituted or substituted by one or more halo substituents;

p is 0–8;

n is 2–8;

m is 0 or 1;

q is 0 or 1;

t is 0 or 1;

each R$^1$ and R$^2$ are independently selected from H, halo, $C_1$–$C_6$ alkyl, $C_3$–$C_6$ alkenyl, $C_3$–$C_6$ alkynyl, —$C_0$–$C_6$ alkyl-NR$^{13}$R$^{14}$, —$C_0$–$C_6$ alkyl-OR$^{12}$, —$C_0$–$C_6$ alkyl-SR$^{12}$, —$C_1$–$C_6$ alkyl-Het, —$C_1$–$C_6$ alkyl-Ar and —$C_1$–$C_6$ alkyl-$C_3$–$C_7$ cycloalkyl, or R$^1$ and R$^2$ together with the carbon to which they are attached form a 3–5 membered carbocyclic or heterocyclic ring, wherein said heterocyclic ring contains one, or more heteroatoms selected from N, O, and S, where any of said $C_1$–$C_6$ alkyl is optionally unsubstituted or substituted by one or more halo substituents;

each R$^3$ is the same or different and is independently selected from halo, cyano, nitro, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het, —$C_0$–$C_6$ alkyl-$C_3$–$C_7$ cycloalkyl, —$C_0$–$C_6$ alkyl-CO$_2$R$^{12}$, —$C_0$–$C_6$ alkyl-C(O)SR$^{12}$, —$C_0$–$C_6$ alkyl-CONR$^{13}$R$^{14}$, —$C_0$–$C_6$ alkyl-COR$^{15}$, —$C_0$–$C_6$ alkyl-NR$^{13}$R$^{14}$, —$C_0$–$C_6$ alkyl-SR$^{12}$, —$C_0$–$C_6$ alkyl-OR$^{12}$, —$C_0$–$C_6$ alkyl-SO$_3$H, —$C_0$–$C_6$ alkyl-SO$_2$NR$^{13}$R$^{14}$, —$C_0$–$C_6$ alkyl-SO$_2$R$^{12}$, —$C_0$–$C_6$ alkyl-SOR$^{15}$, —$C_0$–$C_6$ alkyl-OCOR$^{15}$, —$C_0$–$C_6$ alkyl-OC(O)NR$^{13}$R$^{14}$, —$C_0$–$C_6$ alkyl-OC(O)OR$^{15}$, —$C_0$–$C_6$ alkyl-NR$^{13}$C(O)OR$^{15}$, —$C_0$–$C_6$ alkyl-NR$^{13}$C(O)NR$^{13}$R$^{14}$, and —$C_0$–$C_6$ alkyl-NR$^{13}$COR$^{15}$, wherein said $C_1$–$C_6$ alkyl is optionally unsubstituted or substituted by one or more halo substituents;

each R$^4$ and R$^5$ is independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

R$^6$ and R$^7$ are each independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

R$^8$ and R$^9$ are each independently selected from H, halo, $C_1$–$C_6$ alkyl, —$C_0$–$C_6$ alkyl-Het, —$C_0$–$C_6$ alkyl-Ar and —$C_0$–$C_6$ alkyl-$C_3$–$C_7$ cycloalkyl;

R$^{10}$ and R$^{11}$ are each independently selected from H, $C_1$–$C_{12}$ alkyl, $C_3$–$C_{12}$ alkenyl, $C_3$–$C_{12}$ alkynyl, —$C_0$–$C_8$ alkyl-Ar, —$C_0$–$C_8$ alkyl-Het, —$C_0$–$C_8$ alkyl-$C_3$–$C_7$ cycloalkyl, —$C_0$–$C_8$ alkyl-O-Ar, —$C_0$–$C_8$ alkyl-O-Het, —$C_0$–$C_8$ alkyl-O—$C_3$–$C_7$ cycloalkyl, —$C_0$–$C_8$ alkyl-S(O)$_x$—$C_0$–$C_6$ alkyl, —$C_0$–$C_8$ alkyl-S(O)$_x$-Ar, —$C_0$–$C_8$ alkyl-S(O)$_x$-Het, —$C_0$–$C_8$ alkyl-S(O)$_x$—$C_3$–$C_7$ cycloalkyl, —$C_0$–$C_8$ alkyl-NH-Ar, —$C_0$–$C_8$ alkyl-NH-Het, —$C_0$–$C_8$ alkyl-NH—$C_3$–$C_7$ cycloalkyl, —$C_0$–$C_8$ alkyl-N($C_1$–$C_4$ alkyl)-Ar, —$C_0$–$C_8$ alkyl-N($C_1$–$C_4$ alkyl)-Het, —$C_0$–$C_8$ alkyl-N($C_1$–$C_4$ alkyl)-$C_3$–$C_7$ cycloalkyl, —$C_0$–$C_8$ alkyl-Ar, —$C_0$–$C_8$ alkyl-Het and —$C_0$–$C_8$ alkyl-$C_3$–$C_7$ cycloalkyl, where x is 0, 1 or 2, or R$^{10}$ and R$^{11}$, together with the nitrogen to which they are attached, form a 4–7 membered heterocyclic ring which optionally contains one or more additional heteroatoms selected from N, O, and S, wherein said $C_1$–$C_{12}$ alkyl, $C_3$–$C_{12}$ alkenyl, or $C_3$–$C_{12}$ alkynyl is optionally substituted by one or more of the substituents independently selected from the group halo, —OH, —SH, —NH$_2$, —NH(unsubstituted $C_1$–$C_6$ alkyl), —N(unsubstituted $C_1$–$C_6$ alkyl)(unsubstituted $C_1$–$C_6$ alkyl), unsubstituted —O$C_1$–$C_6$ alkyl, —CO$_2$H, —CO$_2$(unsubstituted $C_1$–$C_6$ alkyl), —CONH$_2$, —CONH(unsubstituted $C_1$–$C_6$ alkyl), —CON(unsubstituted $C_1$–$C_6$ alkyl)(unsubstituted $C_1$–$C_6$ alkyl), —SO$_3$H, —SO$_2$NH$_2$, —SO$_2$NH(unsubstituted $C_1$–$C_6$ alkyl) and —SO$_2$N(unsubstituted $C_1$–$C_6$ alkyl)(unsubstituted $C_1$–$C_6$ alkyl);

R$^{12}$ is selected from H, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl;

each R$^{13}$ and each R$^{14}$ are independently selected from H, $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl, or R$^{13}$ and R$^{14}$ together with the nitrogen to which they are attached form a 4–7 membered heterocyclic ring which optionally contains one or more additional heteroatoms selected from N, O, and S; and R$^{15}$ is selected from $C_1$–$C_6$ alkyl, $C_3$–$C_6$ alkenyl, $C_3$–$C_6$ alkynyl, —$C_0$–$C_6$ alkyl-Ar, —$C_0$–$C_6$ alkyl-Het and —$C_0$–$C_6$ alkyl-$C_3$–$C_7$ cycloalkyl;

provided that R$^{10}$ and R$^{11}$ are not both H when Z is CH or N, Y is —O—, n is 3, m is 1 and each R$^4$, R$^5$, R$^6$, R$^7$ are H, W$^3$ is H, p is 0 or p is 1 or 2 and R$^1$ and R$^2$ are each H, k is 0 or k is 1 and R$^3$ is halo or $C_1$–$C_4$ alkoxy, q is 0 or q is 1 or 2 and R$^8$ and R$^9$ are each H, Q is unsubstituted $C_3$–$C_7$ cycloalkyl, phenyl or Het, or phenyl substituted by one or more substituents selected from halo, —CH$_3$, —CH$_2$CH$_3$, —CF$_3$, —O$C_1$–$C_4$ alkyl, —OCH$_2$CH$_2$OH, —OCF$_3$, —OCF$_2$H, —SCH$_3$, —SCF$_3$, —SO$_2$CH$_3$, —CO$_2$H, —CO$_2$CH$_3$, —OH, —OCH$_2$CO$_2$H, —CH$_2$CONH$_2$, —NO$_2$, —CN, —N(CH$_3$)$_2$, and —NHC(O)CH$_3$, or Het substituted by one or more substituents selected from: —$C_1$–$C_3$ alkyl, —O$C_1$–$C_4$ alkyl, —CH$_2$OH, —CO$_2$H, —CO$_2$CH$_2$CH$_3$, —CO$_2$-tert-$C_4$H$_9$ alkyl, —CO$_2$CH$_2$-phenyl, —CONH$_2$, —C(O)phenyl, —C(O)CH$_3$, —CH$_2$CH$_2$-phenyl, and oxo, t is 0, and W$^1$ and W$^2$ are each independently selected from unsubstituted cyclohexyl and unsubstituted phenyl; or provided that the compound is not:

3-[3-[[2-[3,4-bis(phenylmethoxy)phenyl]-2-hydroxyethyl](phenylmethyl)amino]propyl]-benzamide, (S)-2-hydroxy-5-[2-[(2-hydroxy-2-phenylethyl)(phenylmethyl)amino]ethoxy]-benzamide, 5-[2-[[2-[3,5-bis(phenylmethoxy)phenyl]-2-hydroxyethyl](phenylmethyl)amino]ethoxy]-2-hydroxy-benzamide, 2-hydroxy-4-[3-[(2-hydroxy-2-phenylethyl)(phenylmethyl)amino]propoxy]-benzamide, 2-hydroxy-4-[2-[(2-hydroxy-2-phenylethyl)(phenylmethyl)amino]ethoxy]-benzamide, (R)-2-hydroxy-5-[2-[(2-hydroxy-2-phenylethyl)(phenylmethyl)amino]ethoxy]-benzamide, 2-hydroxy-5-[3-[(2-hydroxy-2-phenylethyl)(phenylmethyl)amino]propyl]-benzamide, 2-hydroxy-5-[2-[(2-hydroxy-2-phenylethyl)(phenylmethyl)amino]ethoxy]-benzamide, 5-[2-[[2-(4-fluorophenyl)-2-hydroxyethyl](phenylmethyl)amino]ethoxy]-2-hydroxy-benzamide, 5-[2-[[2-[3-(aminosulfonyl)-4-methoxyphenyl]-2-hydroxyethyl](phenylmethyl)amino]ethoxy]-2-hydroxy-benzamide, (R)-4-[2-[[2-hydroxy-2-[3-(trifluoromethyl)phenyl]ethyl](phenylmethyl)amino]ethoxy]-benzeneacetamide, (R)-4-[2-[(2-hydroxy-2-phenylethyl)(phenylmethyl)amino]ethoxy]-benzeneacetamide, 4-[2-[(2-hydroxy-2-phenylethyl)(phenylmethyl)amino]ethoxy]-benzeneacetamide, 5-[2-[[2-(4-fluorophenyl)-2-hydroxyethyl](phenylmethyl)amino]ethoxy]-2-hydroxy-benzamine, or 4-[2-[[2-[3,4-bis(phenylmethoxy)phenyl]-2-hydroxyethyl](phenylmethyl)amino]ethoxy]-benzamide, or a pharmaceutically acceptable salt or solvate thereof.

2. The compound according to claim 1, wherein p is 0, 1 or 2.

3. The compound according to claim 1, wherein t is 0.

4. The compound according to claim 1, wherein $R^1$, $R^2$, $R^8$ and $R^9$ are each H.

5. The compound according to claim 1, wherein Z is CH.

6. The compound according to claim 1, wherein k is 0 or 1.

7. The compound according to claim 1, wherein $R^3$ is selected from halo, $C_1$–$C_4$ alkyl and $C_1$–$C_4$ alkoxy.

8. The compound according to claim 1, wherein n is 2–4.

9. The compound according to claim 1, wherein n is 3.

10. The compound according to claim 1, wherein q is 1.

11. The compound according to claim 1, wherein $R^4$ and $R^5$ are independently selected from H and $C_1$–$C_4$ alkyl.

12. The compound according to claim 1, wherein $R^{10}$ and $R^{11}$ are independently selected from H and $C_1$–$C_4$ alkyl, or $R^{10}$ and $R^{11}$, together with the nitrogen to which they are attached, form a substituted or unsubstituted 4–7 membered heterocyclic ring which optionally contains one or more additional heteroatoms selected from N and O, wherein the substituted ring is substituted with $C_1$–$C_4$ alkyl.

13. The compound according to claim 1, wherein $R^{10}$ and $R^{11}$ are each independently selected from H, methyl and ethyl, or $R^{10}$ and $R^{11}$, together with the nitrogen to which they are attached, form a azetidinly, pyrrolidinly, piperidnyl, azepanyl, N-methyl-piperazinyl, or morpholinyl group.

14. The compound according to claim 1, wherein Q is aryl.

15. The compound according to claim 1, wherein Q is phenyl optionally substituted with two substituents selected from halo and $C_1$–$C_4$ haloalkyl.

16. The compound according to claim 1, wherein m is 0 or m is 1 and $R^6$ and $R^7$ are both H.

17. The compound according to claim 1, wherein $W^3$ is H.

18. The compound according to claim 1 wherein $W^1$ and $W^2$ are each unsubstituted phenyl or $W^1$ is unsubstituted phenyl and $W^2$ is methyl.

19. A compound having Formula II:

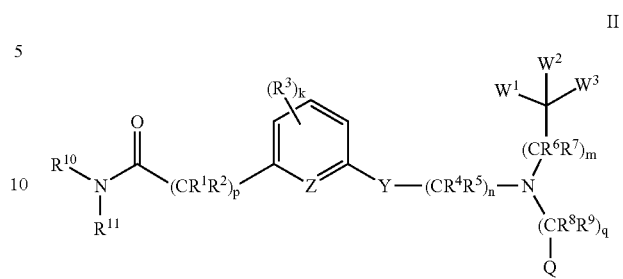

wherein:

Z is CH or N, wherein k is 0, 1 or 2;

Y is —O— or —C($R^4$)($R^5$)—;

$W^1$ is selected from $C_1$–$C_6$ alkyl, $C_3$–$C_8$ cycloalkyl, aryl or Het, wherein said $C_1$–$C_6$ alkyl, $C_3$–$C_8$ cycloalkyl, Ar and Het are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-C(O)$SR^{12}$, —$C_0$–$C_4$ alkyl-CON$R^{13}R^{14}$, —$C_0$–$C_4$ alkyl-COR$^{15}$, —$C_0$–$C_4$ alkyl-N$R^{13}R^{14}$, —$C_0$–$C_4$ alkyl-S$R^{12}$, —$C_0$–$C_4$ alkyl-O$R^{12}$, —$C_0$–$C_4$ alkyl-$SO_3H$, —$C_0$–$C_4$ alkyl-$SO_2NR^{13}R^{14}$, —$C_0$–$C_4$ alkyl-$SO_2R^{12}$, —$C_0$–$C_4$ alkyl-SOR$^{15}$, —$C_0$–$C_4$ alkyl-OCOR$^{15}$, —$C_0$–$C_4$ alkyl-OC(O)N$R^{13}R^{14}$, —$C_0$–$C_4$ alkyl-OC(O)O$R^{15}$, —$C_0$–$C_4$ alkyl-N$R^{13}$C(O)O$R^{15}$, —$C_0$–$C_4$ alkyl-N$R^{13}$C(O)N$R^{13}R^{14}$, and —$C_0$–$C_4$ alkyl-N$R^{13}$COR$^{15}$, where said $C_1$–$C_6$ alkyl is optionally unsubstituted or substituted by one or more halo substituents;

$W^2$ is selected from H, halo, $C_1$–$C_6$ alkyl, $C_2$–$C_6$ alkenyl, $C_2$–$C_6$ alkynyl, —$C_0$–$C_4$ alkyl-N$R^{13}R^{14}$, —$C_0$–$C_4$ alkyl-S$R^{12}$, —$C_0$–$C_4$ alkyl-O$R^{12}$, —$C_0$–$C_4$ alkyl-$CO_2R^{12}$, —$C_0$–$C_4$ alkyl-C(O)S$R^{12}$, —$C_0$–$C_4$ alkyl-CON$R^{13}R^{14}$, —$C_0$–$C_4$ alkyl-COR$^{15}$, —$C_0$–$C_4$ alkyl-OCOR$^{15}$, —$C_0$–$C_4$ alkyl-OCON$R^{13}R^{14}$, —$C_0$–$C_4$ alkyl-N$R^{13}$CON$R^{13}R^{14}$, —$C_0$–$C_4$ alkyl-N$R^{13}$COR$^{15}$, —$C_0$–$C_4$ alkyl-Het, —$C_0$–$C_4$ alkyl-Ar and —$C_0$–$C_4$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_4$ alkyl-Het, —$C_0$–$C_4$ alkyl-Ar and —$C_0$–$C_4$ alkyl-$C_3$–$C_7$ cycloalkyl are optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_4$ alkyl-$CO_2R^{12}$, —$C_0$–$C_4$ alkyl-C(O)S$R^{12}$, —$C_0$–$C_4$ alkyl-CON$R^{13}R^{14}$, —$C_0$–$C_4$ alkyl-COR$^{15}$, —$C_0$–$C_4$ alkyl-N$R^{13}R^{14}$, —$C_0$–$C_4$ alkyl-S$R^{12}$, —$C_0$–$C_4$ alkyl-O$R^{12}$, —$C_0$–$C_4$ alkyl-$SO_3H$, —$C_0$–$C_4$ alkyl-$SO_2NR^{13}R^{14}$, —$C_0$–$C_4$ alkyl-$SO_2R^{12}$, —$C_0$–$C_4$ alkyl-SOR$^{15}$, —$C_0$–$C_4$ alkyl-OCOR$^{15}$, —$C_0$–$C_4$ alkyl-OC(O)N$R^{13}R^{14}$, —$C_0$–$C_4$ alkyl-OC(O)O$R^{15}$, —$C_0$–$C_4$ alkyl-N$R^{13}$C(O)O$R^{15}$, —$C_0$–$C_4$ alkyl-N$R^{13}$C(O)N$R^{13}R^{14}$, and —$C_0$–$C_4$ alkyl-N$R^{13}$COR$^{15}$, where said $C_1$–$C_6$ alkyl, is optionally unsubstituted or substituted by one or more halo substituents;

$W^3$ is selected from the group consisting of: H, halo, $C_1$–$C_6$ alkyl, —$C_0$–$C_4$ alkyl-N$R^{13}R^{14}$, —$C_0$–$C_4$ alkyl-S$R^{12}$, —$C_0$–$C_4$ alkyl-O$R^{12}$, —$C_0$–$C_4$ alkyl-$CO_2R^{12}$, —$C_0$–$C_4$ alkyl-C(O)S$R^{12}$, —$C_0$–$C_4$ alkyl-CON$R^{13}R^{14}$, —$C_0$–$C_4$ alkyl-COR$^{15}$, —$C_0$–$C_4$ alkyl-OCOR$^{15}$, —$C_0$–$C_4$ alkyl-OCON$R^{13}R^{14}$, —$C_0$–$C_4$ alkyl- NR$^{13}$CONR$^{13}$R$^{14}$, —C$_0$–C$_4$ alkyl-NR$^{13}$COR$^{15}$, —C$_0$–C$_4$ alkyl-Het, —C$_1$–C$_4$ alkyl-Ar and —C$_1$–C$_4$ alkyl-C$_3$–C$_7$ cycloalkyl, wherein said C$_1$–C$_6$ alkyl is optionally unsubstituted or substituted by one or more halo substituents;

Q is phenyl or Het; wherein said phenyl or Het are optionally unsubstituted or substituted with one or more groups independently selected from halo, cyano, nitro, C$_1$–C$_6$ alkyl, C$_3$–C$_6$ alkenyl, C$_3$–C$_6$ alkynyl, —C$_0$–C$_4$ alkyl-CO$_2$R$^{12}$, —C$_0$–C$_4$ alkyl-C(O)SR$^{12}$, —C$_0$–C$_4$ alkyl-CONR$^{13}$R$^{14}$, —C$_0$–C$_4$ alkyl-COR$^{15}$, —C$_0$–C$_4$ alkyl-NR$^{13}$R$^{14}$, —C$_0$–C$_4$ alkyl-SR$^{12}$, —C$_0$–C$_4$ alkyl-OR$^{12}$, —C$_0$–C$_4$ alkyl-SO$_3$H, —C$_0$–C$_4$ alkyl-SO$_2$NR$^{13}$R$^{14}$, —C$_0$–C$_4$ alkyl-SO$_2$R$^{12}$, —C$_0$–C$_4$ alkyl-SOR$^{15}$, —C$_0$–C$_4$ alkyl-OCOR$^{15}$, —C$_0$–C$_4$ alkyl-OC(O)NR$^{13}$R$^{14}$, —C$_0$–C$_4$ alkyl-OC(O)OR$^{15}$, —C$_0$–C$_4$ alkyl-NR$^{13}$C(O)OR$^{15}$, —C$_0$–C$_4$ alkyl-NR$^{13}$C(O)NR$^{13}$R$^{14}$, and —C$_0$–C$_4$ alkyl-NR$^{13}$COR$^{15}$, where said C$_1$–C$_6$ alkyl is optionally unsubstituted or substituted by one or more halo substituents, p is 0–4;
n is 3;
m is 0 or 1;
q is 0 or 1;
t is 0;

each R$^1$ and R$^2$ are independently selected from H, fluoro, C$_1$–C$_6$ alkyl, —C$_0$–C$_4$ alkyl-OR$^{12}$, —C$_0$–C$_4$ alkyl-SR$^{12}$, —C$_1$–C$_4$ alkyl-Het, —C$_1$–C$_4$ alkyl-Ar and —C$_1$–C$_4$ alkyl-C$_3$–C$_7$ cycloalkyl, where any of said C$_1$–C$_6$ alkyl is optionally unsubstituted or substituted by one or more halo substituents;

each R$^3$ is the same or different and is independently selected from halo, cyano, C$_1$–C$_6$ alkyl, —C$_0$–C$_4$ alkyl-NR$^{13}$R$^{14}$, —C$_0$–C$_4$ alkyl-OR$^{12}$, —C$_0$–C$_4$ alkyl-SO$_2$NR$^{13}$R$^{14}$, and —C$_0$–C$_4$ alkyl-CO$_2$H, wherein said C$_1$–C$_6$ alkyl is optionally unsubstituted or substituted by one or more halo substituents;

each R$^4$ and R$^5$ is independently selected from H, fluoro and C$_1$–C$_6$ alkyl;

R$^6$ and R$^7$ are each independently selected from H, fluoro and C$_1$–C$_6$ alkyl;

R$^8$ and R$^9$ are each independently selected from H, fluoro and C$_1$–C$_6$ alkyl;

R$^{10}$ and R$^{11}$ are each independently selected from H, C$_1$–C$_{10}$ alkyl, C$_3$–C$_8$ alkenyl, C$_3$–C$_8$ alkynyl, —C$_0$–C$_6$ alkyl-Ar, —C$_0$–C$_6$ alkyl-Het, —C$_0$–C$_6$ alkyl-C$_3$–C$_7$ cycloalkyl, —C$_0$–C$_6$ alkyl-O-Ar, —C$_0$–C$_6$ alkyl-O-Het, —C$_0$–C$_6$ alkyl-O—C$_3$–C$_7$ cycloalkyl, —C$_0$–C$_6$ alkyl-S(O)$_x$—C$_1$–C$_6$ alkyl, —C$_0$–C$_6$ alkyl-S(O)$_x$-Ar, —C$_0$–C$_6$ alkyl-S(O)$_x$-Het, —C$_0$–C$_6$ alkyl-S(O)$_x$—C$_3$–C$_7$ cycloalkyl, —C$_0$–C$_6$ alkyl-NH-Ar, —C$_0$–C$_6$ alkyl-NH-Het, —C$_0$–C$_6$ alkyl-NH—C$_3$–C$_7$ cycloalkyl, —C$_0$–C$_6$ alkyl-N(C$_1$–C$_4$ alkyl)-Ar, —C$_0$–C$_6$ alkyl-N(C$_1$–C$_4$ alkyl)-Het, —C$_0$–C$_6$ alkyl-N(C$_1$–C$_4$ alkyl)-C$_3$–C$_7$ cycloalkyl, —C$_0$–C$_6$ alkyl-Ar, —C$_0$–C$_6$ alkyl-Het and —C$_0$–C$_6$ alkyl-C$_3$–C$_7$ cycloalkyl, where x is 0, 1 or 2, or R$^{11}$ and R$^{12}$, together with the nitrogen to which they are attached, form a 4–7 membered heterocyclic ring which optionally contains one or more additional heteroatoms selected from N, O, and S, wherein said C$_1$–C$_{10}$ alkyl, C$_3$–C$_{10}$ alkenyl, C$_3$–C$_{10}$ alkynyl are optionally substituted by one or more of the substituents independently selected from the group halo, —OH, —SH, —NH$_2$, —NH(unsubstituted C$_1$–C$_4$ alkyl), —N(unsubstituted C$_1$–C$_4$ alkyl)(unsubstituted C$_1$–C$_4$ alkyl), unsubstituted —OC$_1$–C$_4$ alkyl, —CO$_2$H, —CO$_2$(unsubstituted C$_1$–C$_4$ alkyl), —CONH$_2$, —CONH(unsubstituted C$^1$–C$_4$ alkyl), —CON(unsubstituted C$_1$–C$_4$ alkyl)(unsubstituted C$_1$–C$_4$ alkyl), —SO$_3$H, —SO$_2$NH$_2$, —SO$_2$NH(unsubstituted C$_1$–C$_4$ alkyl) and —SO$_2$N(unsubstituted C$_1$–C$_4$ alkyl)(unsubstituted C$_1$–C$_4$ alkyl);

R$^{12}$ is selected from H, C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl;

each R$^{13}$ and R$^{14}$ are each independently selected from H, C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl, or R$^{13}$ and R$^{14}$ together with the nitrogen to which they are attached form a 4–7 membered heterocyclic ring which optionally contains one or more additional heteroatoms selected from N, O, and S; and R$^{15}$ is selected from C$_1$–C$_6$ alkyl, —C$_0$–C$_4$ alkyl-Ar, —C$_0$–C$_4$ alkyl-Het and —C$_0$–C$_4$ alkyl-C$_3$–C$_7$ cycloalkyl;

provided that R$^{10}$ and R$^{11}$ are not both H when Z is CH or N, Y is —O—, n is 3, m is 1 and each R$^4$, R$^5$, R$^6$, R$^7$ are H, W$^3$ is H, p is 0 or p is 1 or 2 and R$^1$ and R$^2$ are each H, k is 0 or k is 1 and R$^3$ is halo or C$_1$–C$_4$ alkoxy, q is 0 or q is 1 or 2 and R$^8$ and R$^9$ are each H, Q is unsubstituted phenyl or Het, or phenyl substituted by one or more substituents selected from halo, —CH$_3$, —CH$_2$CH$_3$, —CF$_3$, —OC$_1$–C$_4$ alkyl, —OCH$_2$CH$_2$OH, —OCF$_3$, —OCF$_2$H, —SCH$_3$, —SCF$_3$, —SO$_2$CH$_3$, —CO$_2$H, —CO$_2$CH$_3$, —OH, —OCH$_2$CO$_2$H, —CH$_2$CONH$_2$, —NO$_2$, —CN, —N(CH$_3$)$_2$, and —NHC(O)CH$_3$, or Het substituted by one or more substituents selected from: —C$_1$–C$_3$ alkyl, —OC$_1$–C$_4$ alkyl, —CH$_2$OH, —CO$_2$H, —CO$_2$CH$_2$CH$_3$, —CO$_2$-tert-C$_4$H$_9$ alkyl, —CO$_2$CH$_2$-phenyl, —CONH$_2$, —C(O)phenyl, —C(O)CH$_3$, —CH$_2$CH$_2$-phenyl, and oxo, t is 0, and W$^1$ and W$^2$ are each independently selected from unsubstituted cyclohexyl and unsubstituted phenyl; or provided that the compound is not 2-hydroxy-4-[3-[(2-hydroxy-2-phenylethyl)(phenylmethyl)amino]propoxy]-benzamide, or a pharmaceutically acceptable salt or solvate thereof.

20. The compound according to claim 1, wherein R$^1$, R$^2$, R$^3$, R$^6$, R$^7$, R$^8$, R$^9$ and W$^3$ are each H; R$^4$ and R$^5$ are each independently selected from H and C$_1$–C$_4$ alkyl, R$^{10}$ and R$^{11}$ are each independently selected from H, C$_1$–C$_{10}$ alkyl, —C$_1$–C$_4$ alkyl-O-Ar, —S(O)$_2$C$_1$–C$_4$ alkyl, —S(O)$_2$-Ar, —C$_1$–C$_4$ alkyl-Het, where the Het group is selected from imidazolyl, thienyl (thiophenyl), morpholinyl, thiomorpholinyl, furyl, tetrahydrofuranyl, pyridyl, isoxazolyl, oxadiazolyl, triazolyl and thiazolyl; or R$^{10}$ and R$^{11}$, together with the nitrogen to which they are attached, form a substituted or unsubstituted 4–7 membered heterocyclic ring which optionally contains one additional heteroatom selected from N and O, wherein the substituted ring is substituted with C$_1$–C$_4$ alkyl, wherein when said C$_0$–C$_4$ alkyl is C$_1$–C$_4$ alkyl, said C$_1$–C$_4$ alkyl is unsubstituted or substituted by —CO$_2$H or —CO$_2$(unsubstituted C$_1$–C$_6$ alkyl); Z is CH; Y is —O— or —C(R$^4$)(R$^5$)—; Q is a substituted phenyl group, containing two substituents selected from halo and C$_1$–C$_4$ haloalkyl; p is 0, 1 or 2; n is 3; m is 0 or 1; q is 1; k is 0; t is 0; and W$^1$ and W$^2$ are aryl or W$^1$ is aryl and W$^2$ is aryl or C$_1$–C$_4$ alkyl; or a pharmaceutically acceptable salt or solvate thereof.

21. The compound according to claim 1, wherein R$^1$, R$^2$, R$^3$, R$^6$, R$^7$, R$^8$, R$^9$ and W$^3$ are each H; R$^4$ and R$^5$ are each independently selected from H and methyl; R$^{10}$ and R$^{11}$ are each independently selected from H, methyl, ethyl, imidazol-2-yl-methyl-, 5-bromo-thiophen-2-yl-methyl-, thiophen-2-yl-methyl-, 2-methoxy-ethyl-, 2-dimethylamino-ethyl-, 2-morpholin-4-yl-ethyl-, 2-methoxy-1-methyl-ethyl-, 2-methoxy-ethyl-, furan-2-yl-methyl-, 3-methyl-isoxazol-5-yl-methyl-, 2-thiomorpholin-4-yl-ethyl-, 2-pyrrolidin-1-yl-ethyl-, pyridin-3-yl-methyl-, 2-pyridin-2-yl-ethyl-, 3-phenoxy-ethyl-, 3-isopropoxy-propyl-, 3-methoxy-propyl-, 5-methyl-[1,3,4] oxadiazol-2-yl-methyl-, 4-methyl-thiazol-2-yl-methyl-, 1-thiophen-2-yl-ethyl-, thiophen-3-yl-methyl-5-methyl-4H-[1,2,4]triazol-3-yl-methyl-, pyridin-2-yl-methyl-, tetrahydrofuran-2-yl-methyl-, 1-ethyl-pyrrolidin-2-yl-methyl-, octyl, decyl, 2-(2-hydroxy-ethoxy)-ethyl-, 1-carboxy-thiophen-2-yl-methyl-, phenyl, methyl-sulfonyl-, phenyl-sulfonyl-, or $R^{10}$ and $R^{11}$, together with the nitrogen to which they are attached, form an azetidinly, pyrrolidinyl, piperidnyl, azepanyl, 4-methyl-piperazin-1-yl, or morpholin-4-yl group; Z is CH; Y is —O—; Q is 2-chloro-3-(trifluoromethyl)phenyl; p is 1; n is 3; q is 1; k is 0; t is 0; m is 1; and $W^1$ and $W^2$ are each unsubstituted phenyl or $W^1$ is unsubstituted phenyl and $W^2$ is methyl; or a pharmaceutically acceptable salt or solvate thereof.

22. A compound selected from:
2-(3-{3-[(2-chloro-3-(trifluoromethyl)-benzyl)-(2,2-diphenylethyl)-amino]-propoxy}phenyl)-1-morpholin-4-yl-ethanone;
2-(3-{3-[(2-chloro-3-(trifluoromethyl)-benzyl)-(2,2-diphenylethyl)-amino]-propoxy}phenyl)-N-methyl-acetamide;
2-(3-{3-[(2-chloro-3-(trifluoromethyl)-benzyl)-(2,2-diphenylethyl)-amino]-propoxy}phenyl)-N,N-dimethyl-acetamide;
2-(3-{3-[(2-chloro-3-(trifluoromethyl)-benzyl)-(2,2-diphenylethyl)-amino]-propoxy}phenyl)-1-piperidyn-1-yl-ethanone;
2-(3-{3-[(2-chloro-3-(trifluoromethyl)-benzyl)-(2,2-diphenylethyl)-amino]-propoxy}phenyl)-1-(4-methyl-piperazin-1-yl)-ethanone;
2-(3-{3-[(2-chloro-3-(trifluoromethyl)-benzyl)-(2,2-diphenylethyl)-amino]-propoxy}phenyl)-1-pyrrolidin-1-yl-ethanone;
2-(3-{3-[(2-chloro-3-(trifluoromethyl)-benzyl)-(2,2-diphenylethyl)-amino]-propoxy}phenyl)-N-ethyl-acetamide;
2-(3-{3-[(2-chloro-3-(trifluoromethyl)-benzyl)-(2,2-diphenylethyl)-amino]-propoxy}phenyl)-N,N-diethyl-acetamide;
2-(3-{3-[(2-chloro-3-(trifluoromethyl)-benzyl)-(2,2-diphenylethyl)-amino]-propoxy}phenyl)-1-azetidin-1-yl-ethanone;
2-(3-{3-[(2-chloro-3-(trifluoromethyl)-benzyl)-(2,2-diphenylethyl)-amino]-propoxy}phenyl)-1-azepan-1-yl-ethanone;
(S)-2-(3-{3-[[2-chloro-3-(trifluoromethyl)benzyl](2-phenyl-propyl)amino]propoxy}-phenyl)-acetamide;
2-(3-{3-[(2-chloro-3-trifluoromethyl-benzyl)-diphenyl-ethyl-amino]-propoxy}-phenyl)-N-(1H-imidazol-2-yl-methyl)-acetamide;
N-(5-bromo-thiophen-2-ylmethyl)-2-(3-{3-[(2-chloro-3-trifluoromethyl-benzyl)-diphenylethyl-amino]-propoxy}-phenyl)-acetamide;
2-(3-{3-[(2-chloro-3-trifluoromethyl-benzyl)-diphenyl-ethyl-amino]-propoxy}-phenyl)-N-thiophen-2-ylmethyl-acetamide;
2-(3-{3-[(2-chloro-3-trifluoromethyl-benzyl)-diphenyl-ethyl-amino]-propoxy}-phenyl)-N-(2-methoxy-ethyl)-acetamide;
2-(3-{3-[(2-chloro-3-trifluoromethyl-benzyl)-diphenyl-ethyl-amino]-propoxy}-phenyl)-N-(2-dimethylamino-ethyl)-acetamide;
2-(3-{3-[(2-chloro-3-trifluoromethyl-benzyl)-diphenyl-ethyl-amino]-propoxy}-phenyl)-N-(2-morpholin-4-yl-ethyl)-acetamide;
2-(3-{3-[(2-chloro-3-trifluoromethyl-benzyl)-diphenyl-ethyl-amino]-propoxy}-phenyl)-N-(2-methoxy-1-methyl-ethyl)-acetamide;
2-(3-{3-[(2-chloro-3-trifluoromethyl-benzyl)-diphenyl-ethyl-amino]-propoxy}-phenyl)-N-(2-methoxy-ethyl)-N-methyl-acetamide;
2-(3-{3-[(2-chloro-3-trifluoromethyl-benzyl)-diphenyl-ethyl-amino]-propoxy}-phenyl)-N,N-bis-(2-methoxy-ethyl)-acetamide;
2-(3-{3-[(2-chloro-3-trifluoromethyl-benzyl)-diphenyl-ethyl-amino]-propoxy}-phenyl)-N-furan-2-ylmethyl-acetamide;
2-(3-{3-[(2-chloro-3-trifluoromethyl-benzyl)-diphenyl-ethyl-amino]-propoxy}-phenyl)-N-(3-methyl-isoxazol-5-ylmethyl)-acetamide;
2-(3-{3-[(2-chloro-3-trifluoromethyl-benzyl)-diphenyl-ethyl-amino]-propoxy}-phenyl)-N-(2-thiomorpholin-4-yl-ethyl)-acetamide;
2-(3-{3-[(2-chloro-3-trifluoromethyl-benzyl)-diphenyl-ethyl-amino]-propoxy}-phenyl)-N-(2-pyrrolidin-1-yl-ethyl)-acetamide;
2-(3-{3-[(2-chloro-3-trifluoromethyl-benzyl)-diphenyl-ethyl-amino]-propoxy}-phenyl)-N-pyridin-3-ylmethyl-acetamide;
2-(3-{3-[(2-chloro-3-trifluoromethyl-benzyl)-diphenyl-ethyl-amino]-propoxy}-phenyl)-N-(2-pyridin-2-yl-ethyl)-acetamide;
2-(3-{3-[(2-chloro-3-trifluoromethyl-benzyl)-diphenyl-ethyl-amino]-propoxy}-phenyl)-N-(3-phenoxy-ethyl)-acetamide;
2-(3-{3-[(2-chloro-3-trifluoromethyl-benzyl)-diphenyl-ethyl-amino]-propoxy}-phenyl)-N-(3-isopropoxy-propyl)-acetamide;
2-(3-{3-[(2-chloro-3-trifluoromethyl-benzyl)-diphenyl-ethyl-amino]-propoxy}-phenyl)-N-(3-methoxy-propyl)-acetamide;
2-(3-{3-[(2-chloro-3-trifluoromethyl-benzyl)-diphenyl-ethyl-amino]-propoxy}-phenyl)-N-(5-methyl-[1,3,4] oxadiazol-2-ylmethyl)-acetamide;
2-(3-{3-[(2-chloro-3-trifluoromethyl-benzyl)-diphenyl-ethyl-amino]-propoxy}-phenyl)-N-(4-methyl-thiazol-2-ylmethyl)-acetamide;
2-(3-{3-[(2-chloro-3-trifluoromethyl-benzyl)-diphenyl-ethyl-amino]-propoxy}-phenyl)-N-(1-thiophen-2-yl-ethyl)-acetamide;
2-(3-{3-[(2-chloro-3-trifluoromethyl-benzyl)-diphenyl-ethyl-amino]-propoxy}-phenyl)-N-thiophen-3-ylmethyl-acetamide;
2-(3-{3-[(2-chloro-3-trifluoromethyl-benzyl)-diphenyl-ethyl-amino]-propoxy}-phenyl)-N-(5-methyl-4H-[1,2,4]triazol-3-ylmethyl)-acetamide;
2-(3-{3-[(2-chloro-3-trifluoromethyl-benzyl)-diphenyl-ethyl-amino]-propoxy}-phenyl)-N-pyridin-2-ylmethyl-acetamide;
2-(3-{3-[(2-chloro-3-trifluoromethyl-benzyl)-diphenyl-ethyl-amino]-propoxy}-phenyl)-N-(tetrahydro-furan-2-ylmethyl)-acetamide;
2-(3-{3-[(2-chloro-3-trifluoromethyl-benzyl)-diphenyl-ethyl-amino]-propoxy}-phenyl)-N-(1-ethyl-pyrrolidin-2-ylmethyl)-acetamide;

2-(3-{3-[(2-chloro-3-trifluoromethyl-benzyl)-diphenyl-ethyl-amino]-propoxy}-phenyl)-N-octyl-acetamide;
2-(3-{3-[(2-chloro-3-trifluoromethyl-benzyl)-diphenyl-ethyl-amino]-propoxy}-phenyl)-N-decyl-acetamide;
2-(3-{3-[(2-chloro-3-trifluoromethyl-benzyl)-diphenyl-ethyl-amino]-propoxy}-phenyl)-N-[2-(2-hydroxy-ethoxy)-ethyl]-acetamide;
[2-(3-{3-[(2-chloro-3-trifluoromethyl-benzyl)-diphenyl-ethyl-amino]-propoxy}-phenyl)-ethanoylamino]-2-thiophen-2-yl-acetic acid;
3-[2-(3-{3-[(2-chloro-3-trifluoromethyl-benzyl)-diphenylethyl-amino]-propoxy}-phenyl)-ethanoylamino]-propionic acid;
3-[2-(3-{3-[(2-chloro-3-trifluoromethyl-benzyl)-diphenylethyl-amino]-propoxy}-phenyl)-ethanoylamino]-acetic acid;
(R)-2-(3-{3-[(2-chloro-3-(trifluoromethyl)-benzyl)-(2,2-diphenylethyl)-amino]-2-methyl-propoxy}phenyl)-1-morpholin-4-yl-ethanone;
2-(3-{(R)-3-[(2-chloro-3-trifluoromethyl-benzyl)-diphenylethyl-amino]-butoxy}-phenyl)-1-morpholin-4-yl-ethanone;
4-{3-[(2-chloro-3-trifluoromethyl-benzyl)-diphenylethyl-amino]-propoxy}-N,N-dimethyl-benzamide;
1-(4-{3-[(2-chloro-3-trifluoromethyl-benzyl)-diphenyl-ethyl-amino]-propoxy}-phenyl)-1-morpholin-4-yl-methanone;
1-(4-{3-[(2-chloro-3-trifluoromethyl-benzyl)-diphenyl-ethyl-amino]-propoxy}-phenyl)-1-(4-methyl-piperazin-1-yl)-methanone;
3-{3-[(2-chloro-3-trifluoromethyl-benzyl)-diphenylethyl-amino]-propoxy}-N,N-dimethyl-benzamide;
3-{3-[(2-chloro-3-trifluoromethyl-benzyl)-diphenylethyl-amino]-propoxy}-N-phenyl-benzamide;
1-(3-{3-[(2-chloro-3-trifluoromethyl-benzyl)-diphenyl-ethyl-amino]-propoxy}-phenyl)-1-morpholin-4-yl-methanone;
1-(3-{3-[(2-chloro-3-trifluoromethyl-benzyl)-diphenyl-ethyl-amino]-propoxy}-phenyl)-1-(4-methyl-piperazin-1-yl)-methanone;
N-[1-(3-{3-[(2-chloro-3-trifluoromethyl-benzyl)-diphenylethyl-amino]-propoxy}-phenyl)-methanoyl]-methanesulfonamide;
N-[1-(3-{3-[(2-chloro-3-trifluoromethyl-benzyl)-diphenylethyl-amino]-propoxy}-phenyl)-methanoyl]-benzenesulfonamide;
N-[2-(3-{3-[(2-chloro-3-trifluoromethyl-benzyl)-diphenylethyl-amino]-propoxy}-phenyl)-ethanoyl]-methanesulfonamide;
N-[2-(3-{3-[(2-chloro-3-trifluoromethyl-benzyl)-diphenylethyl-amino]-propoxy}-phenyl)-ethanoyl]-benzenesulfonamide
N-[-(3-{3-[(2-chloro-3-trifluoromethyl-benzyl)-diphenylethyl-amino]-propoxy}-phenyl-ethanoyl]-N-methyl-benzenesulfonamide;
N-[2-(3-{3-[(chlorotrifluoromethyl-benzyl)-diphenyl-ethyl-amino]-propoxy}-phenyl)-ethanoyl]-N-methyl-methanesulfonamide;
2-(3-{3-[(2-chloro-3-trifluoromethyl-benzyl)-((S)-2-phenyl-propyl)-amino]-propoxy}-phenyl)-1-morpholin-4-yl-ethanone;
2-(3-{3-[(2-chloro-3-trifluoromethyl-benzyl)-((S)-2-phenyl-propyl)-amino]-propoxy}-phenyl)-N-ethyl-acetamide;
2-(3-{3-[(2-chloro-3-trifluoromethyl-benzyl)-((R)-2-phenyl-propyl)-amino]-propoxy}-phenyl)-N,N-dimethyl-acetamide;
2-(3-{3-[(2-chloro-3-trifluoromethyl-benzyl)-((R)-2-phenyl-propyl)-amino]-propoxy}-phenyl)acetamide;
2-(3-{3-[(2-cChloro-3-trifluoromethyl-benzyl)-((R)-2-phenyl-propyl)-amino]-propoxy}-phenyl)-N-methyl-acetamide;
2-(3-{3-[(2-chloro-3-trifluoromethyl-benzyl)-((R)-2-phenyl-propyl)-amino]-propoxy}-phenyl)-N,N-dimethyl-acetamide, and a stereoisomer, a stereoisomeric mixture or racemate thereof and a pharmaceutically acceptable salt or solvate thereof.

23. The compound according to claim 22 selected from:
2-(3-{3-[(2-chloro-3-(trifluoromethyl)-benzyl)-(2,2-diphenylethyl)-amino]-propoxy}phenyl)-N-methyl-acetamide,
2-(3-{3-[(2-chloro-3-(trifluoromethyl)-benzyl)-(2,2-diphenylethyl)-amino]-propoxy}phenyl)-N,N-dimethyl-acetamide,
2-(3-{3-[(2-chloro-3-(trifluoromethyl)-benzyl)-(2,2-diphenylethyl)-amino]-propoxy}phenyl)-N-ethyl-acetamide,
2-(3-{3-[(2-chloro-3-trifluoromethyl-benzyl)-diphenyl-ethyl-amino]-propoxy}-phenyl)-N,N-bis-(2-methoxy-ethyl)-acetamide;
2-(3-{3-[(2-chloro-3-trifluoromethyl-benzyl)-diphenyl-ethyl-amino]-propoxy}-phenyl)-N-thiophen-3-ylm-ethyl-acetamide;
2-(3-{3-[(2-chloro-3-trifluoromethyl-benzyl)-((R)-2-phenyl-propyl)-amino]-propoxy}-phenyl)acetamide;
2-(3-{3-[(2-chloro-3-trifluoromethyl-benzyl)-((R)-2-phenyl-propyl)-amino]-propoxy}-phenyl)-N-methyl-acetamide;

and a stereoisomer, a stereoisomeric mixture or racemate thereof and a pharmaceutically acceptable salt or solvate thereof.

24. The compound according to claim 1, wherein at least one of Y, $W^1$, $W^2$, $W^3$, t, $R^1$, $R^2$, $R^4$, $R^5$, $R^6$, $R^7$, $R^8$, $R^9$, $R^{10}$ or $R^{11}$ is defined as follows:

wherein:

Y is —S—, —N($R^{12}$)—, or —C($R^4$)($R^5$)—; or $W^1$ is $C_1$–$C_6$ alkyl or Het, optionally unsubstituted or substituted with one or more groups independently selected from halo, cyano, nitro, $C_1$–$C_6$ alkyl, $C_3$–$C_6$ alkenyl, $C_3$–$C_6$ alkynyl, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$SO_3H$, —$C_0$–$C_6$ alkyl-$SO_2NR^{13}R^{14}$, —$C_0$–$C_6$ alkyl-$SO_2R^{12}$, —$C_0$–$C_6$ alkyl-$SOR^{15}$, —$C_0$–$C_6$ alkyl-$OCOR^{15}$, —$C_0$–$C_6$ alkyl-OC(O)$NR^{13}R^{14}$, —$C_0$–$C_6$ alkyl-OC(O)$OR^{15}$, —$C_0$–$C_6$ alkyl-$NR^{13}$C(O)$OR^{15}$, —$C_0$–$C_6$ alkyl-$NR^{13}$C(O)$NR^{13}R^{14}$, and —$C_0$–$C_6$ alkyl-$NR^{13}COR^{15}$, where said $C_1$–$C_6$ alkyl, is optionally unsubstituted or substituted by one or more halo substituents; or $W^2$ is H, halo, $C_1$–$C_6$ alkyl, $C_2$–$C_6$ alkenyl, $C_2$–$C_6$ alkynyl, —$C_0$–$C_6$ alkyl-$NR^{13}R^{14}$, —$C_0$–$C_6$ alkyl-$SR^{12}$, —$C_0$–$C_6$ alkyl-$OR^{12}$, —$C_0$–$C_6$ alkyl-$CO_2R^{12}$, —$C_0$–$C_6$ alkyl-C(O)$SR^{12}$, —$C_0$–$C_6$ alkyl-$CONR^{13}R^{14}$, —$C_0$–$C_6$ alkyl-$COR^{15}$, —$C_0$–$C_6$ alkyl-$OCOR^{15}$, —$C_0$–$C_6$ alkyl-$OCONR^{13}R^{14}$, —$C_0$–$C_6$ alkyl-$NR^{13}CONR^{13}R^{14}$, —$C_0$–$C_6$ alkyl-$NR^{13}COR^{15}$, —$C_0$–$C_6$ alkyl-Het, —$C_1$–$C_6$ alkyl-Ar or —$C_1$–$C_6$ alkyl-$C_3$–$C_7$ cycloalkyl, wherein said $C_1$–$C_6$ alkyl is optionally unsubstituted or substituted by one or more halo substituents, and wherein the $C_3$–$C_7$ cycloalkyl, Ar and Het moieties of said —$C_0$–$C_6$ alkyl-Het, —$C_1$–$C_6$ alkyl-Ar and $-C_1-C_6$ alkyl-$C_3-C_7$ cycloalkyl are optionally unsubstituted or substituted with one or more groups independently selected from halo, cyano, nitro, $C_1-C_6$ alkyl, $C_3-C_6$ alkenyl, $C_3-C_6$ alkynyl, $-C_0-C_6$ alkyl-$CO_2R^{12}$, $-C_0-C_6$ alkyl-$C(O)SR^{12}$, $-C_0-C_6$ alkyl-$CONR^{13}R^{14}$, $-C_0-C_6$ alkyl-$COR^{15}$, $-C_0-C_6$ alkyl-$NR^{13}R^{14}$, $-C_0-C_6$ alkyl-$SR^{12}$, $-C_0-C_6$ alkyl-$OR^{12}$, $-C_0-C_6$ alkyl-$SO_3H$, $-C_0-C_6$ alkyl-$SO_2NR^{13}R^{14}$, $-C_0-C_6$ alkyl-$SO_2R^{12}$, $-C_0-C_6$ alkyl-$SOR^{15}$, $-C_0-C_6$ alkyl-$OCOR^{15}$, $-C_0-C_6$ alkyl-$OC(O)NR^{13}R^{14}$, $-C_0-C_6$ alkyl-$OC(O)OR^{15}$, $-C_0-C_6$ alkyl-$NR^{13}C(O)OR^{15}$, $-C_0-C_6$ alkyl-$NR^{13}C(O)NR^{13}R^{14}$, and $-C_0-C_6$ alkyl-$NR^{13}COR^{15}$, where said $C_1-C_6$ alkyl, is optionally unsubstituted or substituted by one or more halo substituents; or $W^3$ is halo, $C_1-C_6$ alkyl, $-C_0-C_6$ alkyl-$NR^{13}R^{14}$, $-C_0-C_6$ alkyl-$SR^{12}$, $-C_0-C_6$ alkyl-$OR^{12}$, $-C_0-C_6$ alkyl-$CO_2R^{12}$, $-C_0-C_6$ alkyl-$C(O)SR^{12}$, $-C_0-C_6$ alkyl-$CONR^{13}R^{14}$, $-C_0-C_6$ alkyl-$COR^{15}$, $-C_0-C_6$ alkyl-$OCOR^{15}$, $-C_0-C_6$ alkyl-$OCONR^{13}R^{14}$, $-C_0-C_6$ alkyl-$NR^{13}CONR^{13}R^{14}$, $-C_0-C_6$ alkyl-$NR^{13}COR^{15}$, $-C_0-C_6$ alkyl-Het, $-C_1-C_6$ alkyl-Ar or $-C_1-C_6$ alkyl-$C_3-C_7$ cycloalkyl, wherein said $C_1-C_6$ alkyl is optionally unsubstituted or substituted by one or more halo substituents; or t is 1; or at least one $R^1$ or $R^2$ is halo, $C_3-C_6$ alkenyl, $C_3-C_6$ alkynyl, $-C_0-C_6$ alkyl-$NR^{13}R^{14}$, $-C_1-C_6$ alkyl-$OR^{12}$, $-C_1-C_6$ alkyl-$SR^{12}$, $-C_1-C_6$ alkyl-Het, $-C_1-C_6$ alkyl-Ar and $-C_1-C_6$ alkyl-$C_3-C_7$ cycloalkyl, or $R^1$ and $R^2$ together with the carbon to which they are attached form a 3–5 membered carbocyclic or heterocyclic ring, wherein said heterocyclic ring contains one, or more heteroatoms selected from N, O, and S, where any of said $C_1-C_6$ alkyl is optionally unsubstituted or substituted by one or more halo substituents; or at least one $R^4$ or $R^5$ is halo, $C_1-C_6$ alkyl, $-C_0-C_6$ alkyl-Het, $-C_0-C_6$ alkyl-Ar or $-C_0-C_6$ alkyl-$C_3-C_7$ cycloalkyl; or at least one $R^6$ or $R^7$ is halo, $C_1-C_6$ alkyl, $-C_0-C_6$ alkyl-Het, $-C_0-C_6$ alkyl-Ar or $-C_0-C_6$ alkyl-$C_3-C_7$ cycloalkyl; or at least one of $R^8$ or $R^9$ is halo, $-C_0-C_6$ alkyl-Het, $-C_0-C_6$ alkyl-Ar or $-C_0-C_6$ alkyl-$C_3-C_7$ cycloalkyl; or at least one of $R^{10}$ and $R^{11}$ is $C_1-C_{12}$ alkyl, $C_3-C_{12}$ alkenyl, $C_3-C_{12}$ alkynyl, $-C_0-C_8$ alkyl-Ar, $-C_0-C_8$ alkyl-Het, $-C_0-C_8$ alkyl-$C_3-C_7$ cycloalkyl, $-C_0-C_8$ alkyl-O-Ar, $-C_0-C_8$ alkyl-O-Het, $-C_0-C_8$ alkyl-O-$C_3-C_7$ cycloalkyl, $-C_0-C_8$ alkyl-$S(O)_x$—$C_1-C_6$ alkyl, $-C_0-C_8$ alkyl-$S(O)_x$-Ar, $-C_0-C_8$ alkyl-$S(O)_x$-Het, $-C_0-C_8$ alkyl-$S(O)_x$—$C_3-C_7$ cycloalkyl, $-C_0-C_8$ alkyl-NH-Ar, $-C_0-C_8$ alkyl-NH-Het, $-C_0-C_8$ alkyl-NH—$C_3-C_7$ cycloalkyl, $-C_0-C_8$ alkyl-$N(C_1-C_4$ alkyl)-Ar, $-C_0-C_8$ alkyl-$N(C_1-C_4$ alkyl)-Het, $-C_0-C_8$ alkyl-$N(C_1-C_4$ alkyl)-$C_3-C_7$ cycloalkyl, $-C_0-C_8$ alkyl-Ar, $-C_0-C_8$ alkyl-Het or $-C_0-C_8$ alkyl-$C_3-C_7$ cycloalkyl, where x is 0, 1 or 2, or $R^{10}$ and $R^{11}$, together with the nitrogen to which they are attached, form a 4–7 membered heterocyclic ring which optionally contains one or more additional heteroatoms selected from N, O, and S, wherein said $C_1-C_6$ alkyl is optionally substituted by one or more of the substituents independently selected from the group halo, —OH, —SH, —$NH_2$, —NH(unsubstituted $C_1-C_6$ alkyl), —N(unsubstituted $C_1-C_6$ alkyl)(unsubstituted $C_1-C_6$ alkyl), unsubstituted —$OC_1-C_6$ alkyl, —$CO_2H$, —$CO_2$(unsubstituted $C_1-C_6$ alkyl), —$CONH_2$, —CONH(unsubstituted $C_1-C_6$ alkyl), —CON(unsubstituted $C_1-C_6$ alkyl)(unsubstituted $C_1-C_6$ alkyl), —$SO_3H$, —$SO_2NH_2$, —$SO_2NH$(unsubstituted $C_1-C_6$ alkyl) and —$SO_2N$(unsubstituted $C_1-C_6$ alkyl)(unsubstituted $C_1-C_6$ alkyl).

25. The compound according to claim 1, wherein at least one of $R^4$, $R^5$, $R^{10}$, $R^{11}$, or $W^2$ is defined as follows, wherein at least one of $R^4$, $R^5$, $R^{10}$ or $R^{11}$ is not H, or $W^2$ is $C_1-C_4$ alkyl or Het.

26. The compound according to claim 1, provided that $R^{10}$ and $R^{11}$ are not both H when: Z is CH, $CR^3$ or N, wherein when Z is CH or $CR^3$, k is 0–4 and when Z is N, k is 0–3; Y is —O—; $W^1$ and $W^2$ are each independently $C_3-C_8$ cycloalkyl or aryl; wherein said $C_3-C_8$ cycloalkyl and Ar are optionally unsubstituted or substituted as defined herein; Q is $C_3-C_8$ cycloalkyl, Ar or 4–8 membered Het; wherein said $C_3-C_8$ cycloalkyl, Ar or Het are optionally unsubstituted or substituted as defined herein; $W^3$ is H; p is 0–6; n is 2–8; m is 0 or 1; q is 0 or 1; t is 0; each $R^1$ and $R^2$ are independently H, $C_1-C_6$ alkyl, —$OC_1-C_6$ alkyl or —$SC_1-C_6$ alkyl; each $R^3$ is the same or different and is independently halo, cyano, nitro, $C_1-C_6$ alkyl, $C_3-C_6$ alkenyl, —$OC_1-C_6$ alkyl, —$C_0-C_6$ alkyl-$CO_2R^{12}$, —$COR^{15}$, —$SR^{12}$, —$SOR^{15}$, —$SO_2R^{12}$, —$OCOC_1-C_6$ alkyl, —$OC(O)NR^{13}R^{14}$, —$CONR^{13}R^{14}$, —$C_0-C_6$ alkyl-$NR^{13}R^{14}$ or a 5–6 membered Het; each $R^4$, $R^5$, $R^6$, $R^7$ and $R^8$ are H; and $R^9$ is H or $C_1-C_6$ alkyl;

where $R^{12}$ is H, $C_1-C_6$ alkyl or $C_3-C_6$ alkenyl and $R^{15}$ is $C_1-C_6$ alkyl or $C_3-C_6$ alkenyl; and where each $R^{13}$ and each $R^{14}$ are independently selected from H, $C_1-C_6$ alkyl, $C_3-C_6$ alkenyl, and $C_3-C_6$ alkynyl.

27. A pharmaceutical composition comprising a compound according to claim 1 and a pharmaceutically acceptable carrier or diluent.

* * * * *